(12) United States Patent
Yokozeki et al.

(10) Patent No.: US 8,389,240 B2
(45) Date of Patent: Mar. 5, 2013

(54) METHOD FOR PRODUCING α-L-ASPARTYL-L-PHENYLALANINE-β-ESTER AND METHOD FOR PRODUCING α-L-ASPARTYL-L-PHENYLALANINE-α-METHYL ESTER

(75) Inventors: Kenzo Yokozeki, Kawasaki (JP); Ayako Ohno, Kawasaki (JP); Seiichi Hara, Kawasaki (JP); Isao Abe, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 13/528,126

(22) Filed: Jun. 20, 2012

(65) Prior Publication Data

US 2012/0295304 A1 Nov. 22, 2012

Related U.S. Application Data

(60) Division of application No. 13/198,075, filed on Aug. 4, 2011, now Pat. No. 8,247,193, which is a division of application No. 12/749,966, filed on Mar. 30, 2010, now Pat. No. 8,034,584, which is a division of application No. 11/970,203, filed on Jan. 7, 2008, now Pat. No. 7,745,172, which is a division of application No. 10/876,673, filed on Jun. 28, 2004, now Pat. No. 7,361,458, which is a continuation of application No. PCT/JP2004/000620, filed on Jan. 23, 2004.

(60) Provisional application No. 60/491,546, filed on Aug. 1, 2003.

(30) Foreign Application Priority Data

| Jan. 24, 2003 | (JP) | 2003-016764 |
| Jul. 25, 2003 | (JP) | 2003-201819 |

(51) Int. Cl.
*C12P 21/06* (2006.01)

(52) U.S. Cl. ........................................ 435/69.1
(58) Field of Classification Search ........................ None
See application file for complete search history.

(56) References Cited

U.S. PATENT DOCUMENTS

| 4,892,820 A | 1/1990 | Hill et al. |
| 7,115,389 B2 | 10/2006 | Hara et al. |
| 7,531,340 B2 | 5/2009 | Hara et al. |
| 2005/0019864 A1 | 1/2005 | Hara et al. |
| 2006/0177893 A1 | 8/2006 | Yokozeki et al. |
| 2007/0190602 A1 | 8/2007 | Abe et al. |

FOREIGN PATENT DOCUMENTS

| EP | 0 127 977 | 12/1984 |
| EP | 0 269 390 | 6/1988 |
| JP | 59-198994 | 10/1984 |
| JP | 2-15196 | 1/1990 |
| JP | 4-311389 | 11/1992 |
| WO | 00/58478 | 10/2000 |
| WO | 2004/011653 | 2/2004 |

OTHER PUBLICATIONS

U.S. Appl. No. 13/528,162, filed Jun. 20, 2012, Yokozeki, et al.
A. Schmid, et al., "Industrial Biocatalysis Today and Tomorrow," Nature, vol. 409, Jan. 11, 2001, pp. 258-268.
Lee, et al., Effect of Methanol on the Synthesis of Aspartame Precursor Catalysed by *Pseudomonas aeruginosa* Elastase, Biotechnology Letter, 1992, 14:779-784.

*Primary Examiner* — Albert Navarro
(74) *Attorney, Agent, or Firm* — Oblon, Spivak, McClelland, Maier & Neustadt, L.L.P.

(57) ABSTRACT

A method of producing an α-L-aspartyl-L-phenylalanine-β-ester by forming the α-L-aspartyl-L-phenylalanine-β-ester from L-aspartic acid-α,β-diester and L-phenylalanine using an enzyme or enzyme-containing substance that has an ability to selectively link L-phenylalanine to an α-ester site of the L-aspartic acid-α,β-diester through a peptide bond.

18 Claims, 1 Drawing Sheet

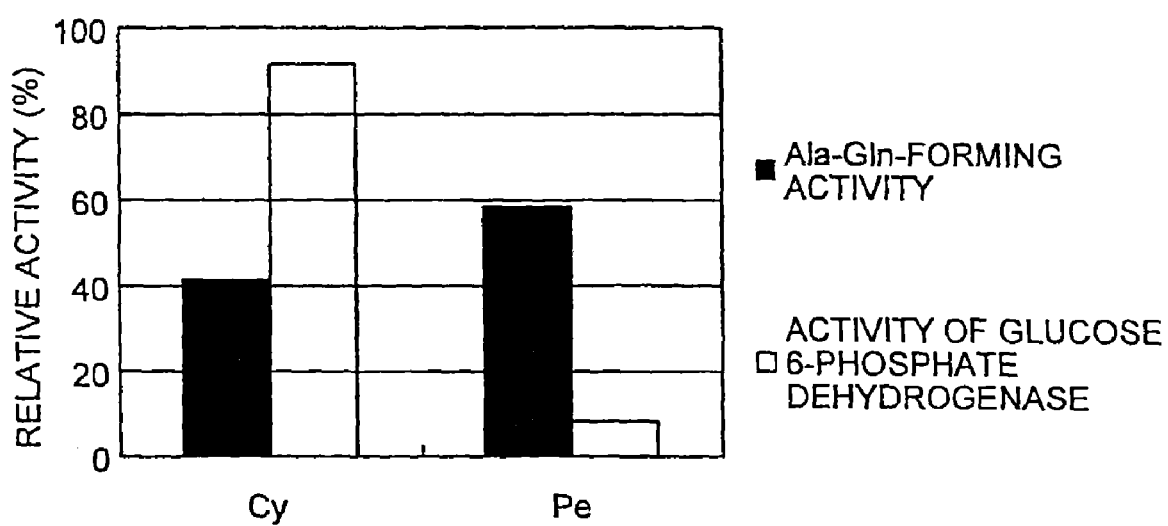

```
                           SEQUENCE LISTING

<160> NUMBER OF SEQ ID NOS: 27

<210> SEQ ID NO 1
<211> LENGTH: 9
<212> TYPE: PRT
<213> ORGANISM: Empedobacter brevis

<400> SEQUENCE: 1

Leu Phe Thr Ala Ile Tyr Gln Pro Lys
1               5

<210> SEQ ID NO 2
<211> LENGTH: 9
<212> TYPE: PRT
<213> ORGANISM: Empedobacter brevis

<400> SEQUENCE: 2

Thr Asn Val Thr Tyr Thr Met Pro Asp
1               5

<210> SEQ ID NO 3
<211> LENGTH: 20
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t

<400> SEQUENCE: 3
ttyacngcna thtaycarcc                                                 20

<210> SEQ ID NO 4
<211> LENGTH: 23
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
```

-continued

```
<221> NAME/KEY: misc_feature
<222> LOCATION: (18)..(18)
<223> OTHER INFORMATION: n is a, c, g, or t

<400> SEQUENCE: 4
tcnggcatng trtangtnac rtt                                             23

<210> SEQ ID NO 5
<211> LENGTH: 2024
<212> TYPE: DNA
<213> ORGANISM: Empedobacter brevis
<220> FEATURE:
<221> NAME/KEY: CDS
<222> LOCATION: (61)..(1908)

<400> SEQUENCE: 5
atttcttaat aaaaactgaa atcttaatac atttatacta tcgtaaaatt tattgaacac     60 gtg aaa aaa tta aca tta aaa gta act cta ctt aca ctt ttg ttg gga     108
Val Lys Lys Leu Thr Leu Lys Val Thr Leu Leu Thr Leu Leu Leu Gly
 1               5                  10                  15 agt aca gtt gga ttt gcg caa gat gca aaa gca gat tct gct tat gtg    156
Ser Thr Val Gly Phe Ala Gln Asp Ala Lys Ala Asp Ser Ala Tyr Val
             20                  25                  30 cgc gac aat tac gaa aaa ata gaa caa gta att ccg atg cgc gat ggt    204
Arg Asp Asn Tyr Glu Lys Ile Glu Gln Val Ile Pro Met Arg Asp Gly
         35                  40                  45 aca aag tta ttt aca gct att tat cag cca aaa gat aaa aca aaa caa    252
Thr Lys Leu Phe Thr Ala Ile Tyr Gln Pro Lys Asp Lys Thr Lys Gln
     50                  55                  60 tat ccc gtt ttg tta aat cgt acg cct tat aca gtt gcg cct tat ggt    300
Tyr Pro Val Leu Leu Asn Arg Thr Pro Tyr Thr Val Ala Pro Tyr Gly
 65                  70                  75                  80 gta aat gaa tac aag aaa tcg tta gga aat ttt cct aca gaa atg cgc    348
Val Asn Glu Tyr Lys Lys Ser Leu Gly Asn Phe Pro Thr Glu Met Arg
                 85                  90                  95 gaa ggt ttt att ttt gtt tac caa gat gtg aga gga aaa tgg atg agc    396
Glu Gly Phe Ile Phe Val Tyr Gln Asp Val Arg Gly Lys Trp Met Ser
            100                 105                 110 gaa ggc gaa ttt gaa gat gtt cga cct ata aat cct tca aaa agt aaa    444
Glu Gly Glu Phe Glu Asp Val Arg Pro Ile Asn Pro Ser Lys Ser Lys
        115                 120                 125 aag gca att gac gaa agc aca gat aca ttt gat acg cta gaa tgg ctt    492
Lys Ala Ile Asp Glu Ser Thr Asp Thr Phe Asp Thr Leu Glu Trp Leu
    130                 135                 140 gct aaa aac ttg aag aat tac acg aaa aaa gct gga att tat gga att    540
Ala Lys Asn Leu Lys Asn Tyr Thr Lys Lys Ala Gly Ile Tyr Gly Ile
145                 150                 155                 160 tcg tat cct ggt ttt tat tcg aca atg agt ttg gtt aat tcg cat cca    588
Ser Tyr Pro Gly Phe Tyr Ser Thr Met Ser Leu Val Asn Ser His Pro
                165                 170                 175 act cta aaa gcc gtt tcg cca caa gcg ccc gtt acc aat tgg ttt tta    636
Thr Leu Lys Ala Val Ser Pro Gln Ala Pro Val Thr Asn Trp Phe Leu
            180                 185                 190 ggt gac gat ttt cat cat aat gga gtt tta ttc ttg aat gat tct ttc    684
Gly Asp Asp Phe His His Asn Gly Val Leu Phe Leu Asn Asp Ser Phe
        195                 200                 205 tca ttt atg act ttt ttt ggt gta aaa cgt ccg caa cca att acg cca    732
Ser Phe Met Thr Phe Phe Gly Val Lys Arg Pro Gln Pro Ile Thr Pro
    210                 215                 220 gat aaa ggt ccg aaa cgt ttt gaa tat cca ata aaa gat aat tat aga    780
Asp Lys Gly Pro Lys Arg Phe Glu Tyr Pro Ile Lys Asp Asn Tyr Arg
225                 230                 235                 240
```

```
                                            -continued ttt tat gca agt ggc tct gta aaa gag ttg aaa gat aaa tat ttg caa      828
Phe Tyr Ala Ser Gly Ser Val Lys Glu Leu Lys Asp Lys Tyr Leu Gln
            245                 250                 255 gat aat atc aag ttt tac aat gat tta ttt gcg cat cca gat tac gat      876
Asp Asn Ile Lys Phe Tyr Asn Asp Leu Phe Ala His Pro Asp Tyr Asp
        260                 265                 270 caa ttt tgg caa gat cgt aat gtt tta cca cat tta act aac gtg caa      924
Gln Phe Trp Gln Asp Arg Asn Val Leu Pro His Leu Thr Asn Val Gln
    275                 280                 285 cct gct gta atg acg gtt gga ggt ttt ttt gat gca gaa gat gtc tac      972
Pro Ala Val Met Thr Val Gly Gly Phe Phe Asp Ala Glu Asp Val Tyr
290                 295                 300 ggc gct ttc gaa acg tat aaa gca att gag aaa caa aat ccg aaa gca     1020
Gly Ala Phe Glu Thr Tyr Lys Ala Ile Glu Lys Gln Asn Pro Lys Ala
305                 310                 315                 320 aca aat att atg gtt gcc gga cct tgg ttt cat ggt ggt tgg gtt cgt     1068
Thr Asn Ile Met Val Ala Gly Pro Trp Phe His Gly Gly Trp Val Arg
            325                 330                 335 agc aac gga agt act ttt gga gat atg caa ttt gca tcg aat aca agt     1116
Ser Asn Gly Ser Thr Phe Gly Asp Met Gln Phe Ala Ser Asn Thr Ser
        340                 345                 350 gag cat tat cag caa gaa ata gaa ttg cct ttt ttt aat tat tac tta     1164
Glu His Tyr Gln Gln Glu Ile Glu Leu Pro Phe Phe Asn Tyr Tyr Leu
    355                 360                 365 aaa gat aaa ggt aat ttt aaa cca acc gaa gct aca att ttt att acg     1212
Lys Asp Lys Gly Asn Phe Lys Pro Thr Glu Ala Thr Ile Phe Ile Thr
370                 375                 380 gga tct aac gaa tgg aaa caa ttt gat gct tgg cca cca aaa aat gta     1260
Gly Ser Asn Glu Trp Lys Gln Phe Asp Ala Trp Pro Pro Lys Asn Val
385                 390                 395                 400 aca aca caa aaa att tat ttg caa caa aat ggt aaa ata gct ttt aat     1308
Thr Thr Gln Lys Ile Tyr Leu Gln Gln Asn Gly Lys Ile Ala Phe Asn
            405                 410                 415 aaa acc aat aca aca act act ttt gac gaa tat gtt gca gat cca aat     1356
Lys Thr Asn Thr Thr Thr Thr Phe Asp Glu Tyr Val Ala Asp Pro Asn
        420                 425                 430 tct cca gtt cct tat tca gga gga gtt tta gaa act cgt tca aga gaa     1404
Ser Pro Val Pro Tyr Ser Gly Gly Val Leu Glu Thr Arg Ser Arg Glu
    435                 440                 445 tat atg gtc gat gat caa cgc ttt gct tct act cgt cct gat gtt atg     1452
Tyr Met Val Asp Asp Gln Arg Phe Ala Ser Thr Arg Pro Asp Val Met
450                 455                 460 gtg tat caa tct gat att ttg aca gaa gat att acg ctt gct ggt cct     1500
Val Tyr Gln Ser Asp Ile Leu Thr Glu Asp Ile Thr Leu Ala Gly Pro
465                 470                 475                 480 gtt atc aat cat tta gtg gtt tct act acg gga aca gac gct gat tat     1548
Val Ile Asn His Leu Val Val Ser Thr Thr Gly Thr Asp Ala Asp Tyr
            485                 490                 495 gtt gta aaa ttg att gat gtt tat cct gaa aac acg cca aaa ttt aat     1596
Val Val Lys Leu Ile Asp Val Tyr Pro Glu Asn Thr Pro Lys Phe Asn
        500                 505                 510 aac aaa tta atg gct gga tat caa aat ttg att cgt gca gaa att atg     1644
Asn Lys Leu Met Ala Gly Tyr Gln Asn Leu Ile Arg Ala Glu Ile Met
    515                 520                 525 cgc gga aaa tat aga aat agt ttc tct aac ccc gaa gct atg gtt ccg     1692
Arg Gly Lys Tyr Arg Asn Ser Phe Ser Asn Pro Glu Ala Met Val Pro
530                 535                 540 aat aaa gaa aca aat gta acg tac acg atg cca gat gtt gga cat aca     1740
Asn Lys Glu Thr Asn Val Thr Tyr Thr Met Pro Asp Val Gly His Thr
545                 550                 555                 560
```

```
ttt aag aaa gga cat cgc att atg att caa gtt cag aac agt tgg ttt      1788
Phe Lys Lys Gly His Arg Ile Met Ile Gln Val Gln Asn Ser Trp Phe
            565                 570                 575 cct tta gca gat cgc aat ccg caa caa ttt atg aat gtt tac gaa gca      1836
Pro Leu Ala Asp Arg Asn Pro Gln Gln Phe Met Asn Val Tyr Glu Ala
        580                 585                 590 act tct aaa gat tat tta aaa caa acg caa cga att tat cat act tct      1884
Thr Ser Lys Asp Tyr Leu Lys Gln Thr Gln Arg Ile Tyr His Thr Ser
    595                 600                 605 tat atc gaa att ccg gta ttg aaa taacaaaaaa atccagctaa ttagctggat      1938
Tyr Ile Glu Ile Pro Val Leu Lys
610                 615 tttttttata atgttacttt tcctattttt cctttatttc caactaaaat tacatatttt      1998
ttatcgggcg aaaccgtaca agtatg                                          2024

<210> SEQ ID NO 6
<211> LENGTH: 616
<212> TYPE: PRT
<213> ORGANISM: Empedobacter brevis

<400> SEQUENCE: 6

Val Lys Lys Leu Thr Leu Lys Val Thr Leu Thr Leu Leu Leu Leu Gly
1               5                   10                  15

Ser Thr Val Gly Phe Ala Gln Asp Ala Lys Ala Asp Ser Ala Tyr Val
            20                  25                  30

Arg Asp Asn Tyr Glu Lys Ile Glu Gln Val Ile Pro Met Arg Asp Gly
        35                  40                  45

Thr Lys Leu Phe Thr Ala Ile Tyr Gln Pro Leu Asp Lys Thr Lys Gln
    50                  55                  60

Tyr Pro Val Leu Leu Asn Arg Thr Pro Tyr Thr Val Ala Pro Tyr Gly
65                  70                  75                  80

Val Asn Glu Tyr Lys Lys Ser Leu Gly Asn Phe Pro Thr Glu Met Arg
                85                  90                  95

Glu Gly Phe Ile Phe Val Tyr Gln Asp Val Arg Gly Lys Trp Met Ser
            100                 105                 110

Glu Gly Glu Phe Glu Asp Val Arg Pro Ile Asn Pro Ser Lys Ser Lys
        115                 120                 125

Lys Ala Ile Asp Glu Ser Thr Asp Thr Phe Asp Thr Leu Glu Trp Leu
    130                 135                 140

Ala Lys Asn Leu Lys Asn Tyr Thr Lys Lys Ala Gly Ile Tyr Gly Ile
145                 150                 155                 160

Ser Tyr Pro Gly Phe Tyr Ser Thr Met Ser Leu Val Asn Ser His Pro
                165                 170                 175

Thr Leu Lys Ala Val Ser Pro Gln Ala Pro Val Thr Asn Trp Phe Leu
            180                 185                 190

Gly Asp Asp Phe His His Asn Gly Val Leu Phe Leu Asn Asp Ser Phe
        195                 200                 205

Ser Phe Met Thr Phe Phe Gly Val Lys Arg Pro Gln Pro Ile Thr Pro
    210                 215                 220

Asp Lys Gly Pro Lys Arg Phe Glu Tyr Pro Ile Lys Asp Asn Tyr Arg
225                 230                 235                 240

Phe Tyr Ala Ser Gly Ser Val Lys Glu Leu Lys Asp Lys Tyr Leu Gln
                245                 250                 255

Asp Asn Ile Lys Phe Tyr Asn Asp Leu Phe Ala His Pro Asp Tyr Asp
            260                 265                 270
```

```
Gln Phe Trp Gln Asp Arg Asn Val Leu Pro His Leu Thr Asn Val Gln
        275                 280                 285
Pro Ala Val Met Thr Val Gly Gly Phe Asp Ala Glu Asp Val Tyr
290                 295                 300
Gly Ala Phe Glu Thr Tyr Lys Ala Ile Glu Lys Gln Asn Pro Lys Ala
305                 310                 315                 320
Thr Asn Ile Met Val Ala Gly Pro Trp Phe His Gly Trp Val Arg
                325                 330                 335
Ser Asn Gly Ser Thr Phe Gly Asp Met Gln Phe Ala Ser Asn Thr Ser
                340                 345                 350
Glu His Tyr Gln Gln Glu Ile Glu Leu Pro Phe Phe Asn Tyr Tyr Leu
                355                 360                 365
Lys Asp Lys Gly Asn Phe Lys Pro Thr Glu Ala Thr Ile Phe Ile Thr
370                 375                 380
Gly Ser Asn Glu Trp Lys Gln Phe Asp Ala Trp Pro Pro Lys Asn Val
385                 390                 395                 400
Thr Thr Gln Lys Ile Tyr Leu Gln Gln Asn Gly Lys Ile Ala Phe Asn
                405                 410                 415
Lys Thr Asn Thr Thr Thr Thr Phe Asp Glu Tyr Val Ala Asp Pro Asn
                420                 425                 430
Ser Pro Val Pro Tyr Ser Gly Gly Val Leu Glu Thr Arg Ser Arg Glu
                435                 440                 445
Tyr Met Val Asp Asp Gln Arg Phe Ala Ser Thr Arg Pro Asp Val Met
450                 455                 460
Val Tyr Gln Ser Asp Ile Leu Thr Glu Asp Ile Thr Leu Ala Gly Pro
465                 470                 475                 480
Val Ile Asn His Leu Val Val Ser Thr Gly Thr Asp Ala Asp Tyr
                485                 490                 495
Val Val Lys Leu Ile Asp Val Tyr Pro Glu Asn Thr Pro Lys Phe Asn
                500                 505                 510
Asn Lys Leu Met Ala Gly Tyr Gln Asn Leu Ile Arg Ala Glu Ile Met
                515                 520                 525
Arg Gly Lys Tyr Arg Asn Ser Phe Ser Asn Pro Glu Ala Met Val Pro
530                 535                 540
Asn Lys Glu Thr Asn Val Thr Tyr Thr Met Pro Asp Val Gly His Thr
545                 550                 555                 560
Phe Lys Lys Gly His Arg Ile Met Ile Gln Val Gln Asn Ser Trp Phe
                565                 570                 575
Pro Leu Ala Asp Arg Asn Pro Gln Gln Phe Met Asn Val Tyr Glu Ala
                580                 585                 590
Thr Ser Lys Asp Tyr Leu Lys Gln Thr Gln Arg Ile Tyr His Thr Ser
                595                 600                 605
Tyr Ile Glu Ile Pro Val Leu Lys
610                 615

<210> SEQ ID NO 7
<211> LENGTH: 40
<212> TYPE: DNA
<213> ORGANISM: Artificial Sequence
<220> FEATURE:
<223> OTHER INFORMATION: Synthetic DNA

<400> SEQUENCE: 7
gtatcacgag gccctagctg tggtgtcatg gtcggtgatc                         40

<210> SEQ ID NO 8
```

-continued

```
<211> LENGTH: 40
<212> TYPE: DNA
<213> ORGANISM: Artificial Sequence
<220> FEATURE:
<223> OTHER INFORMATION: Synthetic DNA

<400> SEQUENCE: 8 ttcgggatt ccatatgata ccctttttac gtgaacttgc                              40

<210> SEQ ID NO 9
<211> LENGTH: 38
<212> TYPE: DNA
<213> ORGANISM: Artificial Sequence
<220> FEATURE:
<223> OTHER INFORMATION: Synthetic DNA

<400> SEQUENCE: 9
gggaattcca tatgaaaaaa ttaacattaa aagtaact                               38

<210> SEQ ID NO 10
<211> LENGTH: 36
<212> TYPE: DNA
<213> ORGANISM: Artificial Sequence
<220> FEATURE:
<223> OTHER INFORMATION: Synthetic DNA

<400> SEQUENCE: 10
gggggctgca gtacttgtac ggtttcgccc gataaa                                 36

<210> SEQ ID NO 11
<211> LENGTH: 1935
<212> TYPE: DNA
<213> ORGANISM: Sphingobacterium sp.
<220> FEATURE:
<221> NAME/KEY: CDS
<222> LOCATION: (61)..(1917)

<400> SEQUENCE: 11
gaaaccaagt gtaaaattat aatttacacc aaagaatgta ctgaacaaat aattatctga       60 atg aaa aat aca att tcg tgc cta act tta gcg ctt tta agc gca agc       108
Met Lys Asn Thr Ile Ser Cys Leu Thr Leu Ala Leu Leu Ser Ala Ser
 1               5                  10                  15 cag tta cat gct caa aca gct gcc gac tcg gct tat gtt aga gat cat       156
Gln Leu His Ala Gln Thr Ala Ala Asp Ser Ala Tyr Val Arg Asp His
             20                  25                  30 tat gaa aag acc gaa gta gca att ccc atg cga gat ggg aaa aaa tta       204
Tyr Glu Lys Thr Glu Val Ala Ile Pro Met Arg Asp Gly Lys Lys Leu
         35                  40                  45 ttt act gcg atc tac agt cca aaa gac aaa tcc aag aaa tat cca gtt       252
Phe Thr Ala Ile Tyr Ser Pro Lys Asp Lys Ser Lys Lys Tyr Pro Val
     50                  55                  60 ttg ctc aat aga acg ccc tac acg gtt tca cct tat ggg cag aac gaa       300
Leu Leu Asn Arg Thr Pro Tyr Thr Val Ser Pro Tyr Gly Gln Asn Glu
 65                  70                  75                  80 tat aaa aaa agc ttg gga aac ttt ccc caa atg atg cgt gaa ggc tat       348
Tyr Lys Lys Ser Leu Gly Asn Phe Pro Gln Met Met Arg Glu Gly Tyr
                 85                  90                  95 att ttc gtt tac cag gat gtc cgt ggc aag tgg atg agc gaa ggt gat       396
Ile Phe Val Tyr Gln Asp Val Arg Gly Lys Trp Met Ser Glu Gly Asp
            100                 105                 110 ttt gaa gat ata cgt ccg acc acg tac agc aaa gat aaa aaa gca atc       444
Phe Glu Asp Ile Arg Pro Thr Thr Tyr Ser Lys Asp Lys Lys Ala Ile
        115                 120                 125 gat gaa agt acg gat acc tat gat gcg ctt gaa tgg tta cag aaa aat       492
```

```
                                                  -continued

Asp Glu Ser Thr Asp Thr Tyr Asp Ala Leu Glu Trp Leu Gln Lys Asn
    130                 135                 140 ctc aaa aac tat aat ggc aaa gcc ggg ctc tat ggg att tcc tat cca    540
Leu Lys Asn Tyr Asn Gly Lys Ala Gly Leu Tyr Gly Ile Ser Tyr Pro
145                 150                 155                 160 ggc ttc tat tct acc gtc gga ttg gtc aaa aca cac ccg agc ttg aag    588
Gly Phe Tyr Ser Thr Val Gly Leu Val Lys Thr His Pro Ser Leu Lys
                165                 170                 175 gca gtc tcc cca cag gct ccc gta aca gac tgg tat atc ggc gac gac    636
Ala Val Ser Pro Gln Ala Pro Val Thr Asp Trp Tyr Ile Gly Asp Asp
            180                 185                 190 ttc cac cat aat ggc gta ttg ttt ctt cag gat gca ttt aca ttc atg    684
Phe His His Asn Gly Val Leu Phe Leu Gln Asp Ala Phe Thr Phe Met
        195                 200                 205 tca acc ttt ggt gtc cct cgt cca aaa ccc att aca ccg gat caa ttt    732
Ser Thr Phe Gly Val Pro Arg Pro Lys Pro Ile Thr Pro Asp Gln Phe
    210                 215                 220 aag ggc aaa att cag atc aaa gaa gcc gat aaa tat aac ttt ttt gca    780
Lys Gly Lys Ile Gln Ile Lys Glu Ala Asp Lys Tyr Asn Phe Phe Ala
225                 230                 235                 240 gaa gca gga aca gcg cgg gaa ctc aaa gaa aag tat ttt ggt gac tcc    828
Glu Ala Gly Thr Ala Arg Glu Leu Lys Glu Lys Tyr Phe Gly Asp Ser
                245                 250                 255 gta caa ttt tgg aat gac ctg ttt aag cat ccc gac tat gat gat ttt    876
Val Gln Phe Trp Asn Asp Leu Phe Lys His Pro Asp Tyr Asp Asp Phe
            260                 265                 270 tgg aaa tcg cgt gtg atc acg aat tct tta cag gag gta aaa cca gct    924
Trp Lys Ser Arg Val Ile Thr Asn Ser Leu Gln Glu Val Lys Pro Ala
        275                 280                 285 gtg atg gtg gtt ggt ggt ttc ttt gac gcg gaa gat gct tat gga aca    972
Val Met Val Val Gly Gly Phe Phe Asp Ala Glu Asp Ala Tyr Gly Thr
    290                 295                 300 ttt aag acc tac caa tcg att gag gat aaa agc aaa aaa aac aac tcg   1020
Phe Lys Thr Tyr Gln Ser Ile Glu Asp Lys Ser Lys Lys Asn Asn Ser
305                 310                 315                 320 att tta gtc gcg gga cct tgg tat cat ggc ggt tgg gtt cgt gca gaa   1068
Ile Leu Val Ala Gly Pro Trp Tyr His Gly Gly Trp Val Arg Ala Glu
                325                 330                 335 gga aac tat tta ggt gat atc caa ttt gag aaa aaa acc agt att act   1116
Gly Asn Tyr Leu Gly Asp Ile Gln Phe Glu Lys Lys Thr Ser Ile Thr
            340                 345                 350 tat cag gaa caa ttt gaa caa cca ttt ttc aaa tat tac cta aaa gat   1164
Tyr Gln Glu Gln Phe Glu Gln Pro Phe Phe Lys Tyr Tyr Leu Lys Asp
        355                 360                 365 gaa gga aac ttc gcc cct tcc gaa gct aac att ttt gtt tca ggc agc   1212
Glu Gly Asn Phe Ala Pro Ser Glu Ala Asn Ile Phe Val Ser Gly Ser
    370                 375                 380 aac gaa tgg aaa cat ttc gaa cag tgg cca cca aaa aat gta gag aca   1260
Asn Glu Trp Lys His Phe Glu Gln Trp Pro Pro Lys Asn Val Glu Thr
385                 390                 395                 400 aaa aaa cta tac ttc caa cct cag ggg aaa ctt gga ttt gac aaa gtt   1308
Lys Lys Leu Tyr Phe Gln Pro Gln Gly Lys Leu Gly Phe Asp Lys Val
                405                 410                 415 caa cgt aca gat tcc tgg gat gaa tat gta aca gac cct aat aaa cct   1356
Gln Arg Thr Asp Ser Trp Asp Glu Tyr Val Thr Asp Pro Asn Lys Pro
            420                 425                 430 gtt ccg cat caa ggt ggg gta att caa aac cga aca cgg gag tat atg   1404
Val Pro His Gln Gly Gly Val Ile Gln Asn Arg Thr Arg Glu Tyr Met
        435                 440                 445 gta gat gat caa cgt ttc gcg gct agt cgc cct gat gtc atg gtt tat   1452
Val Asp Asp Gln Arg Phe Ala Ala Ser Arg Pro Asp Val Met Val Tyr
```

```
Val Asp Asp Gln Arg Phe Ala Ala Ser Arg Pro Asp Val Met Val Tyr
    450                 455                 460 caa acg gaa ccg ttg acg gag gac ctg acg ata gta ggc cca atc aaa    1500
Gln Thr Glu Pro Leu Thr Glu Asp Leu Thr Ile Val Gly Pro Ile Lys
465                 470                 475                 480 aac ttt ctc aaa gtt tct tca aca gga aca gac gcg gac tat gtt gtc    1548
Asn Phe Leu Lys Val Ser Ser Thr Gly Thr Asp Ala Asp Tyr Val Val
                485                 490                 495 aaa ctg att gac gtt tat ccg aat gat gca gca agt tat caa gga aaa    1596
Lys Leu Ile Asp Val Tyr Pro Asn Asp Ala Ala Ser Tyr Gln Gly Lys
                500                 505                 510 aca atg gct gga tat caa atg atg gta cgt ggt gag atc atg gcg ggg    1644
Thr Met Ala Gly Tyr Gln Met Met Val Arg Gly Glu Ile Met Ala Gly
                515                 520                 525 aaa tac cga aat ggt ttc gat aaa gcg cag gcc ttg act cca ggt atg    1692
Lys Tyr Arg Asn Gly Phe Asp Lys Ala Gln Ala Leu Thr Pro Gly Met
    530                 535                 540 gtc gaa aag gtg aat ttt gaa atg cca gac gtt gcg cat acc ttc aaa    1740
Val Glu Lys Val Asn Phe Glu Met Pro Asp Val Ala His Thr Phe Lys
545                 550                 555                 560 aaa gga cat cgc att atg gtt cag gta caa aac tca tgg ttt ccg ctg    1788
Lys Gly His Arg Ile Met Val Gln Val Gln Asn Ser Trp Phe Pro Leu
                565                 570                 575 gca gaa cga aat cca cag gtg ttt tta gca cct tat aca gct acc aaa    1836
Ala Glu Arg Asn Pro Gln Val Phe Leu Ala Pro Tyr Thr Ala Thr Lys
                580                 585                 590 gct gat ttc cgc aaa gct acc caa cgt att ttt cac gat gtg aac aat    1884
Ala Asp Phe Arg Lys Ala Thr Gln Arg Ile Phe His Asp Val Asn Asn
                595                 600                 605 gcc aca tac atc gaa ttt tct gtc ctc aaa gat tagcaggtaa attcgaaa    1935
Ala Thr Tyr Ile Glu Phe Ser Val Leu Lys Asp
    610                 615

<210> SEQ ID NO 12
<211> LENGTH: 619
<212> TYPE: PRT
<213> ORGANISM: Sphingobacterium sp.

<400> SEQUENCE: 12

Met Lys Asn Thr Ile Ser Cys Leu Thr Leu Ala Leu Leu Ser Ala Ser
1               5                   10                  15

Gln Leu His Ala Gln Thr Ala Ala Asp Ser Ala Tyr Val Arg Asp His
                20                  25                  30

Tyr Glu Lys Thr Glu Val Ala Ile Pro Met Arg Asp Gly Lys Lys Leu
            35                  40                  45

Phe Thr Ala Ile Tyr Ser Pro Lys Asp Lys Ser Lys Lys Tyr Pro Val
        50                  55                  60

Leu Leu Asn Arg Thr Pro Tyr Thr Val Ser Pro Tyr Gly Gln Asn Glu
65                  70                  75                  80

Tyr Lys Lys Ser Leu Gly Asn Phe Pro Gln Met Met Arg Glu Gly Tyr
                85                  90                  95

Ile Phe Val Tyr Gln Asp Val Arg Gly Lys Trp Met Ser Glu Gly Asp
            100                 105                 110

Phe Glu Asp Ile Arg Pro Thr Thr Tyr Ser Lys Asp Lys Lys Ala Ile
        115                 120                 125

Asp Glu Ser Thr Asp Thr Tyr Asp Ala Leu Glu Trp Leu Gln Lys Asn
    130                 135                 140

Leu Lys Asn Tyr Asn Gly Lys Ala Gly Leu Tyr Gly Ile Ser Tyr Pro
145                 150                 155                 160
```

-continued

Gly Phe Tyr Ser Thr Val Gly Leu Val Lys Thr His Pro Ser Leu Lys
            165                 170                 175

Ala Val Ser Pro Gln Ala Pro Val Thr Asp Trp Tyr Ile Gly Asp Asp
            180                 185                 190

Phe His His Asn Gly Val Leu Phe Leu Gln Asp Ala Phe Thr Phe Met
            195                 200                 205

Ser Thr Phe Gly Val Pro Arg Pro Lys Pro Ile Thr Pro Asp Gln Phe
210                 215                 220

Lys Gly Lys Ile Gln Ile Lys Glu Ala Asp Lys Tyr Asn Phe Phe Ala
225                 230                 235                 240

Glu Ala Gly Thr Ala Arg Glu Leu Lys Glu Lys Tyr Phe Gly Asp Ser
            245                 250                 255

Val Gln Phe Trp Asn Asp Leu Phe Lys His Pro Asp Tyr Asp Asp Phe
            260                 265                 270

Trp Lys Ser Arg Val Ile Thr Asn Ser Leu Gln Glu Val Lys Pro Ala
            275                 280                 285

Val Met Val Val Gly Gly Phe Phe Asp Ala Glu Asp Ala Tyr Gly Thr
            290                 295                 300

Phe Lys Thr Tyr Gln Ser Ile Glu Asp Lys Ser Lys Lys Asn Asn Ser
305                 310                 315                 320

Ile Leu Val Ala Gly Pro Trp Tyr His Gly Gly Trp Val Arg Ala Glu
            325                 330                 335

Gly Asn Tyr Leu Gly Asp Ile Gln Phe Glu Lys Lys Thr Ser Ile Thr
            340                 345                 350

Tyr Gln Glu Gln Phe Glu Gln Pro Phe Phe Lys Tyr Tyr Leu Lys Asp
            355                 360                 365

Glu Gly Asn Phe Ala Pro Ser Glu Ala Asn Ile Phe Val Ser Gly Ser
            370                 375                 380

Asn Glu Trp Lys His Phe Glu Gln Trp Pro Pro Lys Asn Val Glu Thr
385                 390                 395                 400

Lys Lys Leu Tyr Phe Gln Pro Gln Gly Lys Leu Gly Phe Asp Lys Val
            405                 410                 415

Gln Arg Thr Asp Ser Trp Asp Glu Tyr Val Thr Asp Pro Asn Lys Pro
            420                 425                 430

Val Pro His Gln Gly Gly Val Ile Gln Asn Arg Thr Arg Glu Tyr Met
            435                 440                 445

Val Asp Asp Gln Arg Phe Ala Ala Ser Arg Pro Asp Val Met Val Tyr
450                 455                 460

Gln Thr Glu Pro Leu Thr Glu Asp Leu Thr Ile Val Gly Pro Ile Lys
465                 470                 475                 480

Asn Phe Leu Lys Val Ser Ser Thr Gly Thr Asp Ala Asp Tyr Val Val
            485                 490                 495

Lys Leu Ile Asp Val Tyr Pro Asn Asp Ala Ala Ser Tyr Gln Gly Lys
            500                 505                 510

Thr Met Ala Gly Tyr Gln Met Met Val Arg Gly Glu Ile Met Ala Gly
            515                 520                 525

Lys Tyr Arg Asn Gly Phe Asp Lys Ala Gln Ala Leu Thr Pro Gly Met
            530                 535                 540

Val Glu Lys Val Asn Phe Glu Met Pro Asp Val Ala His Thr Phe Lys
545                 550                 555                 560

Lys Gly His Arg Ile Met Val Gln Val Gln Asn Ser Trp Phe Pro Leu
            565                 570                 575

Ala Glu Arg Asn Pro Gln Val Phe Leu Ala Pro Tyr Thr Ala Thr Lys

-continued

```
              580             585             590
Ala Asp Phe Arg Lys Ala Thr Gln Arg Ile Phe His Asp Val Asn Asn
        595             600             605

Ala Thr Tyr Ile Glu Phe Ser Val Leu Lys Asp
        610             615

<210> SEQ ID NO 13
<211> LENGTH: 30
<212> TYPE: DNA
<213> ORGANISM: Artificial Sequence
<220> FEATURE:
<223> OTHER INFORMATION: Synthetic DNA

<400> SEQUENCE: 13
gggaattcca tatgaaaaat acaatttcgt                                    30

<210> SEQ ID NO 14
<211> LENGTH: 29
<212> TYPE: DNA
<213> ORGANISM: Artificial Sequence
<220> FEATURE:
<223> OTHER INFORMATION: Synthetic DNA

<400> SEQUENCE: 14
gctctagact aatctttgag gacagaaaa                                     29

<210> SEQ ID NO 15
<211> LENGTH: 17
<212> TYPE: DNA
<213> ORGANISM: Artificial Sequence
<220> FEATURE:
<223> OTHER INFORMATION: Synthetic DNA

<400> SEQUENCE: 15
gaygayttyc aycayaa                                                  17

<210> SEQ ID NO 16
<211> LENGTH: 20
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (9)..(9)
<223> OTHER INFORMATION: n = any base

<400> SEQUENCE: 16
tgrtcrtcna ccatrtaytc                                               20

<210> SEQ ID NO 17
<211> LENGTH: 1974
<212> TYPE: DNA
<213> ORGANISM: Pedobacter heparinus
<220> FEATURE:
<221> NAME/KEY: CDS
<222> LOCATION: (61)..(1935)

<400> SEQUENCE: 17
aaacctatcc cgtattcagc aatcaattcc atatatttat ccttaaaaaa accttcctct   60 atg act cct ttc aaa tcg ttc tcc ttc att ttt ctc ttt att ttt acc  108
Met Thr Pro Phe Lys Ser Phe Ser Phe Ile Phe Leu Phe Ile Phe Thr
1               5                   10                  15 agt ctt tct gct tct gca caa cag tcc gac tct gct tat ata cgt cag  156
Ser Leu Ser Ala Ser Ala Gln Gln Ser Asp Ser Ala Tyr Ile Arg Gln
            20                  25                  30
```

|     |     |
| --- | --- |
| aac tat acc aaa ata gaa agg ctg atc cct atg cgg gat ggc att aag<br>Asn Tyr Thr Lys Ile Glu Arg Leu Ile Pro Met Arg Asp Gly Ile Lys<br>           35                    40                    45 | 204 |
| cta ttt aca gcc att tac atc ccc aaa gac aaa agc aag aag tat cct<br>Leu Phe Thr Ala Ile Tyr Ile Pro Lys Asp Lys Ser Lys Lys Tyr Pro<br>50                    55                    60 | 252 |
| ttt atg ctc aac cgt act cct tat acc gtt tcg cct tat ggc gaa aac<br>Phe Met Leu Asn Arg Thr Pro Tyr Thr Val Ser Pro Tyr Gly Glu Asn<br>65                    70                    75                    80 | 300 |
| aat tat aaa aca agc ctt ggc ccc tct ccg ctc ttt ata aaa gaa ggc<br>Asn Tyr Lys Thr Ser Leu Gly Pro Ser Pro Leu Phe Ile Lys Glu Gly<br>                    85                    90                        95 | 348 |
| ttt atc ttt gtt tat cag gat gta agg ggc aaa tgg atg agt gag gga<br>Phe Ile Phe Val Tyr Gln Asp Val Arg Gly Lys Trp Met Ser Glu Gly<br>                  100                 105                110 | 396 |
| aaa ttt gaa gac gta agg ccg caa ata gcc agc aag aaa cgc aaa acg<br>Lys Phe Glu Asp Val Arg Pro Gln Ile Ala Ser Lys Lys Arg Lys Thr<br>                115                 120                125 | 444 |
| gat att gat gaa agc tcc gat act tat gat acg atc gac tgg ctg atc<br>Asp Ile Asp Glu Ser Ser Asp Thr Tyr Asp Thr Ile Asp Trp Leu Ile<br>130                    135                 140 | 492 |
| agg aac att cct gga aac aac cgt aaa acc ggt att tac ggt atc tca<br>Arg Asn Ile Pro Gly Asn Asn Arg Lys Thr Gly Ile Tyr Gly Ile Ser<br>145                    150                 155                160 | 540 |
| tac cca ggc ttt tat gct act gct gcc cta cca gat gcg cat cca tct<br>Tyr Pro Gly Phe Tyr Ala Thr Ala Ala Leu Pro Asp Ala His Pro Ser<br>                  165                 170                175 | 588 |
| tta aag gca gta tcg ccc cag gct ccg gtt acc gac tgg ttt ata ggc<br>Leu Lys Ala Val Ser Pro Gln Ala Pro Val Thr Asp Trp Phe Ile Gly<br>                  180                 185                190 | 636 |
| gat gat ttt cat cac aat ggc acc ttg ttc ctt gca gat atc ttt agc<br>Asp Asp Phe His His Asn Gly Thr Leu Phe Leu Ala Asp Ile Phe Ser<br>                  195                 200                205 | 684 |
| ttc tat tat acc ttc ggg gta ccg cga cct caa cca att acg ccc gac<br>Phe Tyr Tyr Thr Phe Gly Val Pro Arg Pro Gln Pro Ile Thr Pro Asp<br>                210                 215                220 | 732 |
| aaa cgt cca aaa ccc ttt gat ttc ccg gtt aaa gac aac tac cgt ttt<br>Lys Arg Pro Lys Pro Phe Asp Phe Pro Val Lys Asp Asn Tyr Arg Phe<br>225                    230                 235                240 | 780 |
| ttt ctt gaa ctg ggc ccc tta aaa aac atc acc aaa aaa tat tat ggc<br>Phe Leu Glu Leu Gly Pro Leu Lys Asn Ile Thr Lys Lys Tyr Tyr Gly<br>                  245                 250                255 | 828 |
| gat acc ata cga ttc tgg aat gat atc aat gcg cat acc aat tat gat<br>Asp Thr Ile Arg Phe Trp Asn Asp Ile Asn Ala His Thr Asn Tyr Asp<br>                260                 265                270 | 876 |
| gcc ttc tgg aaa gcc cgt aac att acg ccg cat tta att ggt gta aaa<br>Ala Phe Trp Lys Ala Arg Asn Ile Thr Pro His Leu Ile Gly Val Lys<br>         275                 280                285 | 924 |
| cct gca gtt ttg gta gtt ggc ggc ttc ttt gat gca gaa gac ctt tac<br>Pro Ala Val Leu Val Val Gly Gly Phe Phe Asp Ala Glu Asp Leu Tyr<br>         290                 295                300 | 972 |
| ggt acg ctt aaa acc tat cag gcc atc gaa aaa caa aat cca tcc tca<br>Gly Thr Leu Lys Thr Tyr Gln Ala Ile Glu Lys Gln Asn Pro Ser Ser<br>305                    310                 315                320 | 1020 |
| aaa aac aac ctc gtt atg ggc ccc tgg tac cat ggt ggc tgg gca aga<br>Lys Asn Asn Leu Val Met Gly Pro Trp Tyr His Gly Gly Trp Ala Arg<br>                  325                 330                335 | 1068 |
| agt acg gga agc agt ttc ggg gat att aat ttc gga cag cca acc agt<br>Ser Thr Gly Ser Ser Phe Gly Asp Ile Asn Phe Gly Gln Pro Thr Ser<br>                  340                 345                350 | 1116 |

```
act tca tac cag caa aat gtt gag ttc cct ttc ttt atg caa tac ctc    1164
Thr Ser Tyr Gln Gln Asn Val Glu Phe Pro Phe Phe Met Gln Tyr Leu
            355                 360                 365 aaa gag gca ccg gat gca aaa att gca gag gca acc att ttt atc act    1212
Lys Glu Ala Pro Asp Ala Lys Ile Ala Glu Ala Thr Ile Phe Ile Thr
370                 375                 380 ggc agc aat gaa tgg aag aaa ttt agc tcc tgg cca cct cag gat aca    1260
Gly Ser Asn Glu Trp Lys Lys Phe Ser Ser Trp Pro Pro Gln Asp Thr
385                 390                 395                 400 gaa gaa aga aca tta tac ctg cag ccc aat ggc aaa ctg agc ttt gag    1308
Glu Glu Arg Thr Leu Tyr Leu Gln Pro Asn Gly Lys Leu Ser Phe Glu
            405                 410                 415 aag gta cag cgg acc gac agc tgg gat gaa tat gta agt gat ccc aat    1356
Lys Val Gln Arg Thr Asp Ser Trp Asp Glu Tyr Val Ser Asp Pro Asn
        420                 425                 430 tca cct gtc cct tat cag gat ggc ata caa acc agc aga acc cgg gaa    1404
Ser Pro Val Pro Tyr Gln Asp Gly Ile Gln Thr Ser Arg Thr Arg Glu
    435                 440                 445 tat atg atc gat gac cag cgt ttt gcc tcg cgc aga ccg gat gta agg    1452
Tyr Met Ile Asp Asp Gln Arg Phe Ala Ser Arg Arg Pro Asp Val Arg
450                 455                 460 gta ttc caa aca gag ccc ctc agt tcc gac ctt aca ctt acc ggc ccg    1500
Val Phe Gln Thr Glu Pro Leu Ser Ser Asp Leu Thr Leu Thr Gly Pro
465                 470                 475                 480 gta ttg gcc aaa ctg gtg gta tca acc aca ggt acg gat gca gat tat    1548
Val Leu Ala Lys Leu Val Val Ser Thr Thr Gly Thr Asp Ala Asp Tyr
            485                 490                 495 gtg gta aaa ctg ata gat gta tat ccg gaa gat aca cca aat cct gta    1596
Val Val Lys Leu Ile Asp Val Tyr Pro Glu Asp Thr Pro Asn Pro Val
        500                 505                 510 cct aac cct aaa aac ctg atc atg ggt ggt tac cag atg ctg gta cgc    1644
Pro Asn Pro Lys Asn Leu Ile Met Gly Gly Tyr Gln Met Leu Val Arg
    515                 520                 525 ggc gag atc atg cgt gga aaa tac cgt aat agc ttt gaa aaa ccc gag    1692
Gly Glu Ile Met Arg Gly Lys Tyr Arg Asn Ser Phe Glu Lys Pro Glu
530                 535                 540 cct ttt gtt cct gga aca att aca aaa gta aac tat gcc ctt ccg gat    1740
Pro Phe Val Pro Gly Thr Ile Thr Lys Val Asn Tyr Ala Leu Pro Asp
545                 550                 555                 560 gta gcc cat acc ttt aaa aaa ggc cac cgc atc atg atc cag gtc cag    1788
Val Ala His Thr Phe Lys Lys Gly His Arg Ile Met Ile Gln Val Gln
            565                 570                 575 aat tca tgg ttt ccc ctg gcc gac cgg aat cca cag cag ttt atg gac    1836
Asn Ser Trp Phe Pro Leu Ala Asp Arg Asn Pro Gln Gln Phe Met Asp
        580                 585                 590 att tac cag gcc gaa cct ggc gat ttc aga aaa gct acg cat agg atc    1884
Ile Tyr Gln Ala Glu Pro Gly Asp Phe Arg Lys Ala Thr His Arg Ile
    595                 600                 605 ttc cac gat gta cac aat gca tct gca att acg gta aac gta ctg aaa    1932
Phe His Asp Val His Asn Ala Ser Ala Ile Thr Val Asn Val Leu Lys
610                 615                 620 cct taaaacggat gaaaccagta tattgtgcca tccttactt                     1974
Pro
625

<210> SEQ ID NO 18
<211> LENGTH: 625
<212> TYPE: PRT
<213> ORGANISM: Pedobacter heparinus

<400> SEQUENCE: 18
```

-continued

```
Met Thr Pro Phe Lys Ser Phe Ser Phe Ile Phe Leu Phe Ile Phe Thr
1               5                   10                  15

Ser Leu Ser Ala Ser Ala Gln Gln Ser Asp Ser Ala Tyr Ile Arg Gln
            20                  25                  30

Asn Tyr Thr Lys Ile Glu Arg Leu Ile Pro Met Arg Asp Gly Ile Lys
            35                  40                  45

Leu Phe Thr Ala Ile Tyr Ile Pro Lys Asp Lys Ser Lys Lys Tyr Pro
50                  55                  60

Phe Met Leu Asn Arg Thr Pro Tyr Thr Val Ser Pro Tyr Gly Glu Asn
65                  70                  75                  80

Asn Tyr Lys Thr Ser Leu Gly Pro Ser Pro Leu Phe Ile Lys Glu Gly
            85                  90                  95

Phe Ile Phe Val Tyr Gln Asp Val Arg Gly Lys Trp Met Ser Glu Gly
                100                 105                 110

Lys Phe Glu Asp Val Arg Pro Gln Ile Ala Ser Lys Lys Arg Lys Thr
            115                 120                 125

Asp Ile Asp Glu Ser Ser Asp Thr Tyr Asp Thr Ile Asp Trp Leu Ile
            130                 135                 140

Arg Asn Ile Pro Gly Asn Asn Arg Lys Thr Gly Ile Tyr Gly Ile Ser
145                 150                 155                 160

Tyr Pro Gly Phe Tyr Ala Thr Ala Ala Leu Pro Asp Ala His Pro Ser
                165                 170                 175

Leu Lys Ala Val Ser Pro Gln Ala Pro Val Thr Asp Trp Phe Ile Gly
            180                 185                 190

Asp Asp Phe His His Asn Gly Thr Leu Phe Leu Ala Asp Ile Phe Ser
            195                 200                 205

Phe Tyr Tyr Thr Phe Gly Val Pro Arg Pro Gln Pro Ile Thr Pro Asp
210                 215                 220

Lys Arg Pro Lys Pro Phe Asp Phe Pro Val Lys Asp Asn Tyr Arg Phe
225                 230                 235                 240

Phe Leu Glu Leu Gly Pro Leu Lys Asn Ile Thr Lys Lys Tyr Tyr Gly
            245                 250                 255

Asp Thr Ile Arg Phe Trp Asn Asp Ile Asn Ala His Thr Asn Tyr Asp
            260                 265                 270

Ala Phe Trp Lys Ala Arg Asn Ile Thr Pro His Leu Ile Gly Val Lys
            275                 280                 285

Pro Ala Val Leu Val Val Gly Gly Phe Phe Asp Ala Glu Asp Leu Tyr
290                 295                 300

Gly Thr Leu Lys Thr Tyr Gln Ala Ile Glu Lys Gln Asn Pro Ser Ser
305                 310                 315                 320

Lys Asn Asn Leu Val Met Gly Pro Trp Tyr His Gly Gly Trp Ala Arg
            325                 330                 335

Ser Thr Gly Ser Ser Phe Gly Asp Ile Asn Phe Gly Gln Pro Thr Ser
            340                 345                 350

Thr Ser Tyr Gln Gln Asn Val Glu Phe Pro Phe Phe Met Gln Tyr Leu
            355                 360                 365

Lys Glu Ala Pro Asp Ala Lys Ile Ala Glu Ala Thr Ile Phe Ile Thr
370                 375                 380

Gly Ser Asn Glu Trp Lys Lys Phe Ser Ser Trp Pro Pro Gln Asp Thr
385                 390                 395                 400

Glu Glu Arg Thr Leu Tyr Leu Gln Pro Asn Gly Lys Leu Ser Phe Glu
            405                 410                 415

Lys Val Gln Arg Thr Asp Ser Trp Asp Glu Tyr Val Ser Asp Pro Asn
```

```
                    420                 425                 430
Ser Pro Val Pro Tyr Gln Asp Gly Ile Gln Thr Ser Arg Thr Arg Glu
            435                 440                 445

Tyr Met Ile Asp Asp Gln Arg Phe Ala Ser Arg Arg Pro Asp Val Arg
    450                 455                 460

Val Phe Gln Thr Glu Pro Leu Ser Ser Asp Leu Thr Leu Thr Gly Pro
465                 470                 475                 480

Val Leu Ala Lys Leu Val Val Ser Thr Thr Gly Thr Asp Ala Asp Tyr
            485                 490                 495

Val Val Lys Leu Ile Asp Val Tyr Pro Glu Asp Thr Pro Asn Pro Val
            500                 505                 510

Pro Asn Pro Lys Asn Leu Ile Met Gly Gly Tyr Gln Met Leu Val Arg
            515                 520                 525

Gly Glu Ile Met Arg Gly Lys Tyr Arg Asn Ser Phe Glu Lys Pro Glu
            530                 535                 540

Pro Phe Val Pro Gly Thr Ile Thr Lys Val Asn Tyr Ala Leu Pro Asp
545                 550                 555                 560

Val Ala His Thr Phe Lys Lys Gly His Arg Ile Met Ile Gln Val Gln
                565                 570                 575

Asn Ser Trp Phe Pro Leu Ala Asp Arg Asn Pro Gln Gln Phe Met Asp
            580                 585                 590

Ile Tyr Gln Ala Glu Pro Gly Asp Phe Arg Lys Ala Thr His Arg Ile
            595                 600                 605

Phe His Asp Val His Asn Ala Ser Ala Ile Thr Val Asn Val Leu Lys
            610                 615                 620

Pro
625

<210> SEQ ID NO 19
<211> LENGTH: 38
<212> TYPE: DNA
<213> ORGANISM: Artificial Sequence
<220> FEATURE:
<223> OTHER INFORMATION: Synthetic DNA

<400> SEQUENCE: 19
gggaattcca tatgactcct ttcaaatcgt tctccttc                              38

<210> SEQ ID NO 20
<211> LENGTH: 30
<212> TYPE: DNA
<213> ORGANISM: Artificial Sequence
<220> FEATURE:
<223> OTHER INFORMATION: Synthetic DNA

<400> SEQUENCE: 20
cccaagcttt taaggtttca gtacgtttac                                       30

<210> SEQ ID NO 21
<211> LENGTH: 17
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (9)..(9)
<223> OTHER INFORMATION: n = any base

<400> SEQUENCE: 21
athttygtnt aycarga                                                     17
```

<210> SEQ ID NO 22
<211> LENGTH: 2018
<212> TYPE: DNA
<213> ORGANISM: Taxeobacter gelupurpurascens
<220> FEATURE:
<221> NAME/KEY: CDS
<222> LOCATION: (61)..(1995)

<400> SEQUENCE: 22

```
ctgaatgtct gctgacgaat tggaactaca ttaggctcgt tcttcaccta cccttccact         60 atg ccc tac tct ttc ccg aaa gtt gcc gcc ctg agt ggc cta ctg gtg        108
Met Pro Tyr Ser Phe Pro Lys Val Ala Ala Leu Ser Gly Leu Leu Val
 1               5                  10                  15 gcc ggt tta tcc ggt gcc cac gcc caa act cct gtt acc tat ccg ctg        156
Ala Gly Leu Ser Gly Ala His Ala Gln Thr Pro Val Thr Tyr Pro Leu
             20                  25                  30 gct tct gag gct gaa aaa gcg cag ctg gcg gtg gta cta gcc gat acg        204
Ala Ser Glu Ala Glu Lys Ala Gln Leu Ala Val Val Leu Ala Asp Thr
         35                  40                  45 gct tac atc aag gag cgc tat acc aaa aca gaa tat cag att ccg atg        252
Ala Tyr Ile Lys Glu Arg Tyr Thr Lys Thr Glu Tyr Gln Ile Pro Met
     50                  55                  60 cgc gat ggg gtg aag ttg tac acc att gtg tac gcg ccc aac gat gcc        300
Arg Asp Gly Val Lys Leu Tyr Thr Ile Val Tyr Ala Pro Asn Asp Ala
 65                  70                  75                  80 aac aag gta aag tac cct att ctg ctc aac cgt acc cct tac gct att        348
Asn Lys Val Lys Tyr Pro Ile Leu Leu Asn Arg Thr Pro Tyr Ala Ile
                 85                  90                  95 ggc ccc tac ggc ccc ggc aaa tac aag ctc aac ctg ggc ccc agc agc        396
Gly Pro Tyr Gly Pro Gly Lys Tyr Lys Leu Asn Leu Gly Pro Ser Ser
            100                 105                 110 acg atg atg cat gag gga tac atc ttc gcc tac cag gat gtg cgt ggg        444
Thr Met Met His Glu Gly Tyr Ile Phe Ala Tyr Gln Asp Val Arg Gly
        115                 120                 125 cga tat atg tcg gaa gga gag ttt gtg gat gtg cgc ccc gaa aag gac        492
Arg Tyr Met Ser Glu Gly Glu Phe Val Asp Val Arg Pro Glu Lys Asp
    130                 135                 140 atg cac aaa ggc aag aac gac atc gat gaa ggc acc gac acc tac gat        540
Met His Lys Gly Lys Asn Asp Ile Asp Glu Gly Thr Asp Thr Tyr Asp
145                 150                 155                 160 acc att gag tgg ctt ctg aag cac ggg ccc aag aat aac ggc cgc gta        588
Thr Ile Glu Trp Leu Leu Lys His Gly Pro Lys Asn Asn Gly Arg Val
                165                 170                 175 ggc cag tgg ggc atc tcc tac ccc ggc tac tat acc gct act ggc cta        636
Gly Gln Trp Gly Ile Ser Tyr Pro Gly Tyr Tyr Thr Ala Thr Gly Leu
            180                 185                 190 ctg agc cgc cac aag gcc cta aag gca tcc tca ccg cag gcc cct att        684
Leu Ser Arg His Lys Ala Leu Lys Ala Ser Ser Pro Gln Ala Pro Ile
        195                 200                 205 gcc gac tgg ttc tgg gac gat ttt cac cac aac ggc gcg ttc ttc ctg        732
Ala Asp Trp Phe Trp Asp Asp Phe His His Asn Gly Ala Phe Phe Leu
    210                 215                 220 ccg cac gct ttc aac ttc ctg gcc tcc ttt ggg ctg gcc cgc ccc cag        780
Pro His Ala Phe Asn Phe Leu Ala Ser Phe Gly Leu Ala Arg Pro Gln
225                 230                 235                 240 ccc acg cct acc ggc aac ccc ggc ttc aag cac ggc acc ccc gat ggc        828
Pro Thr Pro Thr Gly Asn Pro Gly Phe Lys His Gly Thr Pro Asp Gly
                245                 250                 255 tac gat ttt ttc ctg aag atg ggt ccg ctg aaa aac gct gat gcc aac        876
Tyr Asp Phe Phe Leu Lys Met Gly Pro Leu Lys Asn Ala Asp Ala Asn
```

```
                  260                 265                 270
tac tac aaa ggc aaa gtg gcc ttc tgg aac gaa atg gcc agc cac ccc    924
Tyr Tyr Lys Gly Lys Val Ala Phe Trp Asn Glu Met Ala Ser His Pro
            275                 280                 285 aac tac gac gaa ttc tgg cag gcc cgt aac cta cgc ccc cac ctc aag    972
Asn Tyr Asp Glu Phe Trp Gln Ala Arg Asn Leu Arg Pro His Leu Lys
        290                 295                 300 aac ctc aac aaa ggc acc gcg gtg ctc acg gtt ggt ggc ttc aat gat   1020
Asn Leu Asn Lys Gly Thr Ala Val Leu Thr Val Gly Gly Phe Asn Asp
305                 310                 315                 320 gcc gag gac ctg ttt ggc gcc ctg aaa acc tac gaa agc atc gag aag   1068
Ala Glu Asp Leu Phe Gly Ala Leu Lys Thr Tyr Glu Ser Ile Glu Lys
                325                 330                 335 caa aac ccc ggc atg cgc aac ggc ctc gtg atg ggg ccg tgg gta cac   1116
Gln Asn Pro Gly Met Arg Asn Gly Leu Val Met Gly Pro Trp Val His
            340                 345                 350 ggt ggc tgg gcc cgc ggc act ggc gaa atg gta ggc aat gtg gcc tac   1164
Gly Gly Trp Ala Arg Gly Thr Gly Glu Met Val Gly Asn Val Ala Tyr
        355                 360                 365 ggc gag tcg ccg tcg ttg tat tac cag aag cag att gaa gcg ccg ttc   1212
Gly Glu Ser Pro Ser Leu Tyr Tyr Gln Lys Gln Ile Glu Ala Pro Phe
    370                 375                 380 ttc aaa tca tat ctg aag gat ggc aaa cct gcc gct acc ccc gag gct   1260
Phe Lys Ser Tyr Leu Lys Asp Gly Lys Pro Ala Ala Thr Pro Glu Ala
385                 390                 395                 400 acc atc ttt gaa agc ggc acc aac cgc tgg cgc agc ttc gaa acc tgg   1308
Thr Ile Phe Glu Ser Gly Thr Asn Arg Trp Arg Ser Phe Glu Thr Trp
                405                 410                 415 ccg ccc aaa gaa gcc aaa gag cgc act ttg tac ttt cag tcg gcc ggg   1356
Pro Pro Lys Glu Ala Lys Glu Arg Thr Leu Tyr Phe Gln Ser Ala Gly
            420                 425                 430 aaa atc ggc ttc gag aag cct gcc agt ggc cta gag tac gac cag ttc   1404
Lys Ile Gly Phe Glu Lys Pro Ala Ser Gly Leu Glu Tyr Asp Gln Phe
        435                 440                 445 ctc agc gac ccg gct cac cca gtg cct ttc acc gaa gct acg gct acg   1452
Leu Ser Asp Pro Ala His Pro Val Pro Phe Thr Glu Ala Thr Ala Thr
    450                 455                 460 ggc atg acc cgc gag tac atg acc gac gac cag cgc ttc gcc agc cgc   1500
Gly Met Thr Arg Glu Tyr Met Thr Asp Asp Gln Arg Phe Ala Ser Arg
465                 470                 475                 480 cgc ccc gac gtg ctg acc tac cag acc gaa gcg ctt acc gag gac atg   1548
Arg Pro Asp Val Leu Thr Tyr Gln Thr Glu Ala Leu Thr Glu Asp Met
                485                 490                 495 acg ctg gct ggc cct atc gag gcg ctg ttg cag gta gcc acc acc ggc   1596
Thr Leu Ala Gly Pro Ile Glu Ala Leu Leu Gln Val Ala Thr Thr Gly
            500                 505                 510 acc gat gcc gac tgg gta gtg aag att att gat gtg tac ccc gac gat   1644
Thr Asp Ala Asp Trp Val Val Lys Ile Ile Asp Val Tyr Pro Asp Asp
        515                 520                 525 acg ccc aac aac ccc agc acg aac ccc gcc gtg aaa ctg ggc ggc tac   1692
Thr Pro Asn Asn Pro Ser Thr Asn Pro Ala Val Lys Leu Gly Gly Tyr
    530                 535                 540 cag cag atg gtt cgc tcc gag gtg atg cgc ggt cgt ttc cgc aac agc   1740
Gln Gln Met Val Arg Ser Glu Val Met Arg Gly Arg Phe Arg Asn Ser
545                 550                 555                 560 ttc tcc aag ccc gaa gcc ttt gta ccg gaa cag gta acg gcc gtg ccc   1788
Phe Ser Lys Pro Glu Ala Phe Val Pro Glu Gln Val Thr Ala Val Pro
                565                 570                 575 ttc acg gtg cag gac ctg tgc cac acc ttc cgg aaa gga cac cgc ctg   1836
Phe Thr Val Gln Asp Leu Cys His Thr Phe Arg Lys Gly His Arg Leu
```

```
                        580                 585                 590
atg gtg cag gtg caa agc agc tgg ttc ccg att gtt gac cgc aac ccg    1884
Met Val Gln Val Gln Ser Ser Trp Phe Pro Ile Val Asp Arg Asn Pro
    595                 600                 605 cag acc ttc gta ccc aat att ttc gag gcc gat gag aag gat ttc cag    1932
Gln Thr Phe Val Pro Asn Ile Phe Glu Ala Asp Glu Lys Asp Phe Gln
610                 615                 620 gcc gcc acg cat cgg ctg tac cat tcg ccg gcg cat agc tcg cag ctc    1980
Ala Ala Thr His Arg Leu Tyr His Ser Pro Ala His Ser Ser Gln Leu
625                 630                 635                 640 acg ttg cgc gtt ctg taggccactc taaacaggct cgg                      2018
Thr Leu Arg Val Leu
                645

<210> SEQ ID NO 23
<211> LENGTH: 645
<212> TYPE: PRT
<213> ORGANISM: Taxeobacter gelupurpurascens

<400> SEQUENCE: 23

Met Pro Tyr Ser Phe Pro Lys Val Ala Ala Leu Ser Gly Leu Leu Val
1               5                   10                  15

Ala Gly Leu Ser Gly Ala His Ala Gln Thr Pro Val Thr Tyr Pro Leu
            20                  25                  30

Ala Ser Glu Ala Glu Lys Ala Gln Leu Ala Val Val Leu Ala Asp Thr
        35                  40                  45

Ala Tyr Ile Lys Glu Arg Tyr Thr Lys Thr Glu Tyr Gln Ile Pro Met
    50                  55                  60

Arg Asp Gly Val Lys Leu Tyr Thr Ile Val Tyr Ala Pro Asn Asp Ala
65                  70                  75                  80

Asn Lys Val Lys Tyr Pro Ile Leu Leu Asn Arg Thr Pro Tyr Ala Ile
                85                  90                  95

Gly Pro Tyr Gly Pro Gly Lys Tyr Lys Leu Asn Leu Gly Pro Ser Ser
            100                 105                 110

Thr Met Met His Glu Gly Tyr Ile Phe Ala Tyr Gln Asp Val Arg Gly
        115                 120                 125

Arg Tyr Met Ser Glu Gly Glu Phe Val Asp Val Arg Pro Glu Lys Asp
    130                 135                 140

Met His Lys Gly Lys Asn Asp Ile Asp Glu Gly Thr Asp Thr Tyr Asp
145                 150                 155                 160

Thr Ile Glu Trp Leu Leu Lys His Gly Pro Lys Asn Asn Gly Arg Val
                165                 170                 175

Gly Gln Trp Gly Ile Ser Tyr Pro Gly Tyr Tyr Thr Ala Thr Gly Leu
            180                 185                 190

Leu Ser Arg His Lys Ala Leu Lys Ala Ser Ser Pro Gln Ala Pro Ile
        195                 200                 205

Ala Asp Trp Phe Trp Asp Phe His His Asn Gly Ala Phe Phe Leu
    210                 215                 220

Pro His Ala Phe Asn Phe Leu Ala Ser Phe Gly Leu Ala Arg Pro Gln
225                 230                 235                 240

Pro Thr Pro Thr Gly Asn Pro Gly Phe Lys His Gly Thr Pro Asp Gly
                245                 250                 255

Tyr Asp Phe Phe Leu Lys Met Gly Pro Leu Lys Asn Ala Asp Ala Asn
            260                 265                 270

Tyr Tyr Lys Gly Lys Val Ala Phe Trp Asn Glu Met Ala Ser His Pro
        275                 280                 285
```

```
Asn Tyr Asp Glu Phe Trp Gln Ala Arg Asn Leu Arg Pro His Leu Lys
290                 295                 300
Asn Leu Asn Lys Gly Thr Ala Val Leu Thr Val Gly Gly Phe Asn Asp
305                 310                 315                 320
Ala Glu Asp Leu Phe Gly Ala Leu Lys Thr Tyr Glu Ser Ile Glu Lys
                325                 330                 335
Gln Asn Pro Gly Met Arg Asn Gly Leu Val Met Gly Pro Trp Val His
            340                 345                 350
Gly Gly Trp Ala Arg Gly Thr Gly Glu Met Val Gly Asn Val Ala Tyr
        355                 360                 365
Gly Glu Ser Pro Ser Leu Tyr Tyr Gln Lys Gln Ile Glu Ala Pro Phe
370                 375                 380
Phe Lys Ser Tyr Leu Lys Asp Gly Lys Pro Ala Ala Thr Pro Glu Ala
385                 390                 395                 400
Thr Ile Phe Glu Ser Gly Thr Asn Arg Trp Arg Ser Phe Glu Thr Trp
                405                 410                 415
Pro Pro Lys Glu Ala Lys Glu Arg Thr Leu Tyr Phe Gln Ser Ala Gly
            420                 425                 430
Lys Ile Gly Phe Glu Lys Pro Ala Ser Gly Leu Glu Tyr Asp Gln Phe
        435                 440                 445
Leu Ser Asp Pro Ala His Pro Val Pro Phe Thr Glu Ala Thr Ala Thr
450                 455                 460
Gly Met Thr Arg Glu Tyr Met Thr Asp Asp Gln Arg Phe Ala Ser Arg
465                 470                 475                 480
Arg Pro Asp Val Leu Thr Tyr Gln Thr Glu Ala Leu Thr Glu Asp Met
                485                 490                 495
Thr Leu Ala Gly Pro Ile Glu Ala Leu Leu Gln Val Ala Thr Thr Gly
            500                 505                 510
Thr Asp Ala Asp Trp Val Val Lys Ile Ile Asp Val Tyr Pro Asp Asp
        515                 520                 525
Thr Pro Asn Asn Pro Ser Thr Asn Pro Ala Val Lys Leu Gly Gly Tyr
530                 535                 540
Gln Gln Met Val Arg Ser Glu Val Met Arg Gly Arg Phe Arg Asn Ser
545                 550                 555                 560
Phe Ser Lys Pro Glu Ala Phe Val Pro Glu Gln Val Thr Ala Val Pro
                565                 570                 575
Phe Thr Val Gln Asp Leu Cys His Thr Phe Arg Lys Gly His Arg Leu
            580                 585                 590
Met Val Gln Val Gln Ser Ser Trp Phe Pro Ile Val Asp Arg Asn Pro
        595                 600                 605
Gln Thr Phe Val Pro Asn Ile Phe Glu Ala Asp Glu Lys Asp Phe Gln
610                 615                 620
Ala Ala Thr His Arg Leu Tyr His Ser Pro Ala His Ser Ser Gln Leu
625                 630                 635                 640
Thr Leu Arg Val Leu
                645

<210> SEQ ID NO 24
<211> LENGTH: 1931
<212> TYPE: DNA
<213> ORGANISM: Cyclobacterium marinum
<220> FEATURE:
<221> NAME/KEY: CDS
<222> LOCATION: (29)..(1888)

<400> SEQUENCE: 24
```

```
cccaaagcat taacaaaata atttagtc atg aaa cac tgt tac aaa ctt ctg        52
                                Met Lys His Cys Tyr Lys Leu Leu
                                 1               5 gtc ttt tac aca tta ttt ttg atg acc aca aac tgg gct tta tca caa      100
Val Phe Tyr Thr Leu Phe Leu Met Thr Thr Asn Trp Ala Leu Ser Gln
 10              15                  20 gcc att aat gga tat gat aag gca gcc tat gac att cct atg cga gat      148
Ala Ile Asn Gly Tyr Asp Lys Ala Ala Tyr Asp Ile Pro Met Arg Asp
 25              30                  35                  40 gga gtt cac ctt cac acc atc gtc tat agc ccc aaa gat tta tcg cag      196
Gly Val His Leu His Thr Ile Val Tyr Ser Pro Lys Asp Leu Ser Gln
                 45                  50                  55 ccc tat cct ata ttg atg caa agg aca cct tac agc gcc ggc cct tat      244
Pro Tyr Pro Ile Leu Met Gln Arg Thr Pro Tyr Ser Ala Gly Pro Tyr
                 60                  65                  70 ggt cct gga aat atg aaa aat aag ctt ggc cct tct cag ttt tta atg      292
Gly Pro Gly Asn Met Lys Asn Lys Leu Gly Pro Ser Gln Phe Leu Met
         75                  80                  85 aac gat ggc tat ata ttt gtt tac cag gat gta aga ggg cgg tgg atg      340
Asn Asp Gly Tyr Ile Phe Val Tyr Gln Asp Val Arg Gly Arg Trp Met
         90                  95                 100 tcg gaa gga tcc tat gac aac atg cgc cct acc cta tcc aaa tca gaa      388
Ser Glu Gly Ser Tyr Asp Asn Met Arg Pro Thr Leu Ser Lys Ser Glu
105                 110                 115                 120 aga aat tcc aac caa ata gac gaa agc aca gac acc tat gat acc ata      436
Arg Asn Ser Asn Gln Ile Asp Glu Ser Thr Asp Thr Tyr Asp Thr Ile
                125                 130                 135 gaa tgg ttg ctc gcc aat atc aaa aat cac aat gaa aaa gta ggc cta      484
Glu Trp Leu Leu Ala Asn Ile Lys Asn His Asn Glu Lys Val Gly Leu
            140                 145                 150 tgg gga atc agc tat ccc gga ttt tat agt gct gca gcc ctt cct ttt      532
Trp Gly Ile Ser Tyr Pro Gly Phe Tyr Ser Ala Ala Ala Leu Pro Phe
            155                 160                 165 gcc cat cca aac ctg aaa gcc gtt tcc cct caa gca ccc ata ggg gat      580
Ala His Pro Asn Leu Lys Ala Val Ser Pro Gln Ala Pro Ile Gly Asp
170                 175                 180 ttt tac ttt gat gat ttt cat cat aac ggt gct tac tta tta agt tat      628
Phe Tyr Phe Asp Asp Phe His His Asn Gly Ala Tyr Leu Leu Ser Tyr
185                 190                 195                 200 tgg ttg gcc act tct gtt ttc ggc tac caa aaa gac ggc cct aca cag      676
Trp Leu Ala Thr Ser Val Phe Gly Tyr Gln Lys Asp Gly Pro Thr Gln
                205                 210                 215 gaa gca tgg tat ggc atg gtg aat ccg gaa aca aat gac ggc tat cag      724
Glu Ala Trp Tyr Gly Met Val Asn Pro Glu Thr Asn Asp Gly Tyr Gln
            220                 225                 230 ttt ttt atg gat atg ggg cca tta aaa aat gcc gat aaa tgg tat ggt      772
Phe Phe Met Asp Met Gly Pro Leu Lys Asn Ala Asp Lys Trp Tyr Gly
            235                 240                 245 gaa gac aat ttt ttc tgg caa caa ctt aaa aac aat cct gat tac aac      820
Glu Asp Asn Phe Phe Trp Gln Gln Leu Lys Asn Asn Pro Asp Tyr Asn
250                 255                 260 gct ttc tgg caa aag aga agt att att cct cac tta aaa gaa gtg aag      868
Ala Phe Trp Gln Lys Arg Ser Ile Ile Pro His Leu Lys Glu Val Lys
265                 270                 275                 280 cct gca gtt tta acc gtt ggg ggc tgg ttt gat gca gaa gat ctc tat      916
Pro Ala Val Leu Thr Val Gly Gly Trp Phe Asp Ala Glu Asp Leu Tyr
                285                 290                 295 gga cca ctt aca att tat aaa acc att gaa aaa aat aat cct gag acc      964
Gly Pro Leu Thr Ile Tyr Lys Thr Ile Glu Lys Asn Asn Pro Glu Thr
                300                 305                 310
```

```
tac aat acc att gtc atg ggc cct tgg tcc cac gga gat tgg tca agg      1012
Tyr Asn Thr Ile Val Met Gly Pro Trp Ser His Gly Asp Trp Ser Arg
        315                 320                 325 gaa cct gga tca cag gtc att tca aat att tat ttt ggt gat tct atc      1060
Glu Pro Gly Ser Gln Val Ile Ser Asn Ile Tyr Phe Gly Asp Ser Ile
330                 335                 340 tcc aca tgg tat caa aaa aat ata gaa cgt gtt ttt ttc aat cat ttt      1108
Ser Thr Trp Tyr Gln Lys Asn Ile Glu Arg Val Phe Phe Asn His Phe
345                 350                 355                 360 cta aaa gaa tcc gaa aat agc aat cct gcc ctt cct gaa gcc tac atg      1156
Leu Lys Glu Ser Glu Asn Ser Asn Pro Ala Leu Pro Glu Ala Tyr Met
                365                 370                 375 ttt gat acc gga aaa cat aaa tgg gaa aaa ttt gac gat tgg cct cct      1204
Phe Asp Thr Gly Lys His Lys Trp Glu Lys Phe Asp Asp Trp Pro Pro
        380                 385                 390 aaa gaa agc caa tgg aaa agc ttt tac ttt caa gag aaa gga gag tta      1252
Lys Glu Ser Gln Trp Lys Ser Phe Tyr Phe Gln Glu Lys Gly Glu Leu
                395                 400                 405 act gag gta aca cct gag gga aat agg ttt act acc tat gtc tca gac      1300
Thr Glu Val Thr Pro Glu Gly Asn Arg Phe Thr Thr Tyr Val Ser Asp
410                 415                 420 ccc tct aat cct gtc ccc tat agt caa gat att aaa cta aac ttc act      1348
Pro Ser Asn Pro Val Pro Tyr Ser Gln Asp Ile Lys Leu Asn Phe Thr
425                 430                 435                 440 ccg aga aaa tac atg gcc gat gac cag cga ttt gca gcc aga aga ccg      1396
Pro Arg Lys Tyr Met Ala Asp Asp Gln Arg Phe Ala Ala Arg Arg Pro
                445                 450                 455 gac gta ctg acc ttt acg agc gaa gta tta agt caa gac atg acg ctt      1444
Asp Val Leu Thr Phe Thr Ser Glu Val Leu Ser Gln Asp Met Thr Leu
        460                 465                 470 gcg ggg gaa gtc atg gca aac tta aaa gtt gcc act tca caa act gat      1492
Ala Gly Glu Val Met Ala Asn Leu Lys Val Ala Thr Ser Gln Thr Asp
                475                 480                 485 gct gat tgg gta gtt aaa atc atc gat ata ttt ccc gga gat cag cca      1540
Ala Asp Trp Val Val Lys Ile Ile Asp Ile Phe Pro Gly Asp Gln Pro
490                 495                 500 aat cat gcc tat gtt tta gat ggg gtg gac atg ggc aat tac cac cta      1588
Asn His Ala Tyr Val Leu Asp Gly Val Asp Met Gly Asn Tyr His Leu
505                 510                 515                 520 atg gtt cgt tca gag gta att aga ggg agg tat aga gaa agt ttt gag      1636
Met Val Arg Ser Glu Val Ile Arg Gly Arg Tyr Arg Glu Ser Phe Glu
                525                 530                 535 ttt cct aaa ccc ttt gtt cct gat caa atc act gct gtt gat ttc agg      1684
Phe Pro Lys Pro Phe Val Pro Asp Gln Ile Thr Ala Val Asp Phe Arg
        540                 545                 550 tta caa gat ctt ttc cat act ttc aaa aag ggg cat aaa att caa ata      1732
Leu Gln Asp Leu Phe His Thr Phe Lys Lys Gly His Lys Ile Gln Ile
                555                 560                 565 caa ata caa agt act tgg ttt ccc cta att gat cga aat ccc caa aaa      1780
Gln Ile Gln Ser Thr Trp Phe Pro Leu Ile Asp Arg Asn Pro Gln Lys
570                 575                 580 tat gta caa aac ata ttt gaa gct gag gaa gcc gat ttt gtc aaa gcc      1828
Tyr Val Gln Asn Ile Phe Glu Ala Glu Glu Ala Asp Phe Val Lys Ala
585                 590                 595                 600 acc cat agg gtt ttt cat aca gaa aag ttt gcc agc aaa att gaa gta      1876
Thr His Arg Val Phe His Thr Glu Lys Phe Ala Ser Lys Ile Glu Val
                605                 610                 615 atg gtt ctt cct tagaattaga atggtttaaa attactattt gtagcagaag ata     1931
Met Val Leu Pro
        620
```

-continued

```
<210> SEQ ID NO 25
<211> LENGTH: 620
<212> TYPE: PRT
<213> ORGANISM: Cyclobacterium marinum

<400> SEQUENCE: 25

Met Lys His Cys Tyr Lys Leu Leu Val Phe Tyr Thr Leu Phe Leu Met
1               5                   10                  15

Thr Thr Asn Trp Ala Leu Ser Gln Ala Ile Asn Gly Tyr Asp Lys Ala
            20                  25                  30

Ala Tyr Asp Ile Pro Met Arg Asp Gly Val His Leu His Thr Ile Val
        35                  40                  45

Tyr Ser Pro Lys Asp Leu Ser Gln Pro Tyr Pro Ile Leu Met Gln Arg
    50                  55                  60

Thr Pro Tyr Ser Ala Gly Pro Tyr Gly Pro Gly Asn Met Lys Asn Lys
65                  70                  75                  80

Leu Gly Pro Ser Gln Phe Leu Met Asn Asp Gly Tyr Ile Phe Val Tyr
                85                  90                  95

Gln Asp Val Arg Gly Arg Trp Met Ser Glu Gly Ser Tyr Asp Asn Met
            100                 105                 110

Arg Pro Thr Leu Ser Lys Ser Glu Arg Asn Ser Asn Gln Ile Asp Glu
        115                 120                 125

Ser Thr Asp Thr Tyr Asp Thr Ile Glu Trp Leu Leu Ala Asn Ile Lys
    130                 135                 140

Asn His Asn Glu Lys Val Gly Leu Trp Gly Ile Ser Tyr Pro Gly Phe
145                 150                 155                 160

Tyr Ser Ala Ala Ala Leu Pro Phe Ala His Pro Asn Leu Lys Ala Val
                165                 170                 175

Ser Pro Gln Ala Pro Ile Gly Asp Phe Tyr Phe Asp Asp Phe His His
            180                 185                 190

Asn Gly Ala Tyr Leu Leu Ser Tyr Trp Leu Ala Thr Ser Val Phe Gly
        195                 200                 205

Tyr Gln Lys Asp Gly Pro Thr Gln Glu Ala Trp Tyr Gly Met Val Asn
    210                 215                 220

Pro Glu Thr Asn Asp Gly Tyr Gln Phe Phe Met Asp Met Gly Pro Leu
225                 230                 235                 240

Lys Asn Ala Asp Lys Trp Tyr Gly Glu Asp Asn Phe Phe Trp Gln Gln
                245                 250                 255

Leu Lys Asn Asn Pro Asp Tyr Asn Ala Phe Trp Gln Lys Arg Ser Ile
            260                 265                 270

Ile Pro His Leu Lys Glu Val Lys Pro Ala Val Leu Thr Val Gly Gly
        275                 280                 285

Trp Phe Asp Ala Glu Asp Leu Tyr Gly Pro Leu Thr Ile Tyr Lys Thr
    290                 295                 300

Ile Glu Lys Asn Asn Pro Glu Thr Tyr Asn Thr Ile Val Met Gly Pro
305                 310                 315                 320

Trp Ser His Gly Asp Trp Ser Arg Glu Pro Gly Ser Gln Val Ile Ser
                325                 330                 335

Asn Ile Tyr Phe Gly Asp Ser Ile Ser Thr Trp Tyr Gln Lys Asn Ile
            340                 345                 350

Glu Arg Val Phe Phe Asn His Phe Leu Lys Glu Ser Glu Asn Ser Asn
        355                 360                 365

Pro Ala Leu Pro Glu Ala Tyr Met Phe Asp Thr Gly Lys His Lys Trp
    370                 375                 380
```

-continued

```
Glu Lys Phe Asp Asp Trp Pro Pro Lys Glu Ser Gln Trp Lys Ser Phe
385                 390                 395                 400

Tyr Phe Gln Glu Lys Gly Glu Leu Thr Glu Val Thr Pro Glu Gly Asn
            405                 410                 415

Arg Phe Thr Thr Tyr Val Ser Asp Pro Ser Asn Pro Val Pro Tyr Ser
        420                 425                 430

Gln Asp Ile Lys Leu Asn Phe Thr Pro Arg Lys Tyr Met Ala Asp Asp
    435                 440                 445

Gln Arg Phe Ala Ala Arg Pro Asp Val Leu Thr Phe Thr Ser Glu
450                 455                 460

Val Leu Ser Gln Asp Met Thr Leu Ala Gly Val Met Ala Asn Leu
465                 470                 475                 480

Lys Val Ala Thr Ser Gln Thr Asp Ala Asp Trp Val Val Lys Ile Ile
                485                 490                 495

Asp Ile Phe Pro Gly Asp Gln Pro Asn His Ala Tyr Val Leu Asp Gly
            500                 505                 510

Val Asp Met Gly Asn Tyr His Leu Met Val Arg Ser Glu Val Ile Arg
        515                 520                 525

Gly Arg Tyr Arg Glu Ser Phe Glu Phe Pro Lys Pro Phe Val Pro Asp
530                 535                 540

Gln Ile Thr Ala Val Asp Phe Arg Leu Gln Asp Leu Phe His Thr Phe
545                 550                 555                 560

Lys Lys Gly His Lys Ile Gln Ile Gln Ile Gln Ser Thr Trp Phe Pro
                565                 570                 575

Leu Ile Asp Arg Asn Pro Gln Lys Tyr Val Gln Asn Ile Phe Glu Ala
            580                 585                 590

Glu Glu Ala Asp Phe Val Lys Ala Thr His Arg Val Phe His Thr Glu
        595                 600                 605

Lys Phe Ala Ser Lys Ile Glu Val Met Val Leu Pro
        610                 615                 620

<210> SEQ ID NO 26
<211> LENGTH: 2036
<212> TYPE: DNA
<213> ORGANISM: Psycloserpens burtonensis
<220> FEATURE:
<221> NAME/KEY: CDS
<222> LOCATION: (61)..(1992)

<400> SEQUENCE: 26
catattcgta aaatagctat aagttttgt aaatttagtc aatcaaaatt ttaaatgtaa      60 atg aag act ctt ttt aaa ttg ttg ctc cta ttt gta ttt gtt cta acg     108
Met Lys Thr Leu Phe Lys Leu Leu Leu Leu Phe Val Phe Val Leu Thr
1               5                   10                  15 tct tgt aat aag gcc aac aaa gac gct act gaa att gtg aaa acc gaa     156
Ser Cys Asn Lys Ala Asn Lys Asp Ala Thr Glu Ile Val Lys Thr Glu
            20                  25                  30 gta gaa gat act tac gtt aaa gat aat tat aac aaa caa gag gtg act     204
Val Glu Asp Thr Tyr Val Lys Asp Asn Tyr Asn Lys Gln Glu Val Thr
        35                  40                  45 att gaa atg cgc gat ggt ata aaa ctt cac acg acc att tat tca cca     252
Ile Glu Met Arg Asp Gly Ile Lys Leu His Thr Thr Ile Tyr Ser Pro
    50                  55                  60 aaa gat gaa agt cag acc tat cct att tta atg atg aga aca cca tat     300
Lys Asp Glu Ser Gln Thr Tyr Pro Ile Leu Met Met Arg Thr Pro Tyr
65                  70                  75                  80 agt tct caa cct tat ggt gac aat gag ttt aag acg aaa att ggt cct     348
Ser Ser Gln Pro Tyr Gly Asp Asn Glu Phe Lys Thr Lys Ile Gly Pro
```

```
                    85                  90                  95
aat gtt cat tta atg aaa gaa ggg aat att gtt gtg tat caa gat gta        396
Asn Val His Leu Met Lys Glu Gly Asn Ile Val Val Tyr Gln Asp Val
            100                 105                 110 cga ggt cgt tgg atg agt gaa ggt gtc tat gat aat atg cgt gct tat        444
Arg Gly Arg Trp Met Ser Glu Gly Val Tyr Asp Asn Met Arg Ala Tyr
                115                 120                 125 atc cca aat aaa aca gag gat tct caa att gat gag gca tca gac act        492
Ile Pro Asn Lys Thr Glu Asp Ser Gln Ile Asp Glu Ala Ser Asp Thr
        130                 135                 140 tat gac acg att gac tgg ctg gta aat aac gta gaa aat aat aac ggg        540
Tyr Asp Thr Ile Asp Trp Leu Val Asn Asn Val Glu Asn Asn Asn Gly
145                 150                 155                 160 aat gtt ggt act tgg gga att tca tat cct ggt ttt tat gct aca tat        588
Asn Val Gly Thr Trp Gly Ile Ser Tyr Pro Gly Phe Tyr Ala Thr Tyr
                165                 170                 175 tct act ata gac gca cac cca gct tta aaa gca gca tcg cct caa gcg        636
Ser Thr Ile Asp Ala His Pro Ala Leu Lys Ala Ala Ser Pro Gln Ala
            180                 185                 190 tgt att gga gat ttc ttt ttt gac gat ttt cat cat aat ggt gct ttt        684
Cys Ile Gly Asp Phe Phe Phe Asp Asp Phe His His Asn Gly Ala Phe
        195                 200                 205 tta tta agt tat ttt aga gca gtg tct tta ttt ggt acg aca aaa gat        732
Leu Leu Ser Tyr Phe Arg Ala Val Ser Leu Phe Gly Thr Thr Lys Asp
210                 215                 220 aaa cct aca gat tct gct tgg tat aag ttt cca gaa atg aaa aca caa        780
Lys Pro Thr Asp Ser Ala Trp Tyr Lys Phe Pro Glu Met Lys Thr Gln
225                 230                 235                 240 gat caa tat caa ttt ttt ctt gat gct gga cct tta agt aat ttg aac        828
Asp Gln Tyr Gln Phe Phe Leu Asp Ala Gly Pro Leu Ser Asn Leu Asn
                245                 250                 255 aag tat ttc caa tat gac aca cca gac gac aca tct gta tcc aag tct        876
Lys Tyr Phe Gln Tyr Asp Thr Pro Asp Asp Thr Ser Val Ser Lys Ser
            260                 265                 270 gat agg ata gat gat gtg ttt tgg aaa gaa att gta gag cat cca aac        924
Asp Arg Ile Asp Asp Val Phe Trp Lys Glu Ile Val Glu His Pro Asn
        275                 280                 285 tac gat acg ata tgg aaa tct aaa ggt tta att caa aac cta aaa gat        972
Tyr Asp Thr Ile Trp Lys Ser Lys Gly Leu Ile Gln Asn Leu Lys Asp
    290                 295                 300 att aag cca agt gta gcg aca atg att gtg gga ggg tta ttt gat gcc       1020
Ile Lys Pro Ser Val Ala Thr Met Ile Val Gly Gly Leu Phe Asp Ala
305                 310                 315                 320 gaa gat tta tat ggg cca ttt gaa act tat aaa acg ata gaa aaa cat       1068
Glu Asp Leu Tyr Gly Pro Phe Glu Thr Tyr Lys Thr Ile Glu Lys His
                325                 330                 335 aat cct gat aat tat aat att atg gtt ttt ggg cct tgg gat cat ggt       1116
Asn Pro Asp Asn Tyr Asn Ile Met Val Phe Gly Pro Trp Asp His Gly
            340                 345                 350 cgt tgg gct agg agt gac gtt aaa aat tat gtt gga aat tat ttc ttc       1164
Arg Trp Ala Arg Ser Asp Val Lys Asn Tyr Val Gly Asn Tyr Phe Phe
        355                 360                 365 gga gat tct ata tct cta aaa ttt caa cgt gat gtt gaa acg aag ttt       1212
Gly Asp Ser Ile Ser Leu Lys Phe Gln Arg Asp Val Glu Thr Lys Phe
    370                 375                 380 ttt aat cat ttt tta aaa gga aaa ggc gac aag aac tca ggg tta cca       1260
Phe Asn His Phe Leu Lys Gly Lys Gly Asp Lys Asn Ser Gly Leu Pro
385                 390                 395                 400 gaa gca tat gta ttt gat tct ggt aaa aag gaa tgg agt agc ttt gac       1308
Glu Ala Tyr Val Phe Asp Ser Gly Lys Lys Glu Trp Ser Ser Phe Asp
```

```
                     405                 410                 415
agc tgg cct cca aag caa gca gaa aaa caa gcc atg tat ctt aat gcc       1356
Ser Trp Pro Pro Lys Gln Ala Glu Lys Gln Ala Met Tyr Leu Asn Ala
            420                 425                 430 aac caa gag cta tca gat tca aaa aaa gga aat act agt gag aca ttt       1404
Asn Gln Glu Leu Ser Asp Ser Lys Lys Gly Asn Thr Ser Glu Thr Phe
                435                 440                 445 gtt agt gat tta aaa cgc cct gta cct tat tcc gaa gat att aaa aca       1452
Val Ser Asp Leu Lys Arg Pro Val Pro Tyr Ser Glu Asp Ile Lys Thr
    450                 455                 460 gtt ttc aca cca cga aaa tac atg aca gac gat cag cgt ttt gca gca       1500
Val Phe Thr Pro Arg Lys Tyr Met Thr Asp Asp Gln Arg Phe Ala Ala
465                 470                 475                 480 cga cgt cct gat gtt ctt ata ttt gag acc gat att ctt gag gaa gat       1548
Arg Arg Pro Asp Val Leu Ile Phe Glu Thr Asp Ile Leu Glu Glu Asp
                485                 490                 495 ata acc tta gct ggt gat att tta gcg cag ctt aat gtg tca act aca       1596
Ile Thr Leu Ala Gly Asp Ile Leu Ala Gln Leu Asn Val Ser Thr Thr
                500                 505                 510 ggg aca gat gca gat tgg att gtc aaa ata gta gat gtt cat cca gca       1644
Gly Thr Asp Ala Asp Trp Ile Val Lys Ile Val Asp Val His Pro Ala
            515                 520                 525 gat gct gag gag caa aaa gaa ggt atg caa gac cat tta tca atg agt       1692
Asp Ala Glu Glu Gln Lys Glu Gly Met Gln Asp His Leu Ser Met Ser
530                 535                 540 aat tat cat ttg atg gtg agg agt gaa gtg atg cgc ggt cgt ttt aga       1740
Asn Tyr His Leu Met Val Arg Ser Glu Val Met Arg Gly Arg Phe Arg
545                 550                 555                 560 aat agt ttt gaa aac cca gag cca ttt gtg cca aac caa cca aca gat       1788
Asn Ser Phe Glu Asn Pro Glu Pro Phe Val Pro Asn Gln Pro Thr Asp
                565                 570                 575 gtc aat atc aag tta caa gat gta cat cat aca ttt aaa aaa ggt cac       1836
Val Asn Ile Lys Leu Gln Asp Val His His Thr Phe Lys Lys Gly His
            580                 585                 590 aaa tta caa gtg caa gtt cag agt acg tgg ttt cca ctt att gat ttg       1884
Lys Leu Gln Val Gln Val Gln Ser Thr Trp Phe Pro Leu Ile Asp Leu
            595                 600                 605 aac ccg caa aca ttt gtg cct aat att tat aaa gca aaa gaa agc gat       1932
Asn Pro Gln Thr Phe Val Pro Asn Ile Tyr Lys Ala Lys Glu Ser Asp
610                 615                 620 ttt aaa acc caa aca cat tcg gtt ttt aac gat tct aaa att gag ttt       1980
Phe Lys Thr Gln Thr His Ser Val Phe Asn Asp Ser Lys Ile Glu Phe
625                 630                 635                 640 acg gtt ttg aaa taagagtaga tgactaaatt tgccaaggta gatttagtct tttt     2036
Thr Val Leu Lys
```

<210> SEQ ID NO 27
<211> LENGTH: 644
<212> TYPE: PRT
<213> ORGANISM: Psycloserpens burtonensis

<400> SEQUENCE: 27

```
Met Lys Thr Leu Phe Lys Leu Leu Leu Phe Val Phe Val Leu Thr
1               5                   10                  15

Ser Cys Asn Lys Ala Asn Lys Asp Ala Thr Glu Ile Val Lys Thr Glu
            20                  25                  30

Val Glu Asp Thr Tyr Val Lys Asp Asn Tyr Asn Lys Gln Glu Val Thr
        35                  40                  45

Ile Glu Met Arg Asp Gly Ile Lys Leu His Thr Thr Ile Tyr Ser Pro
    50                  55                  60
```

-continued

```
Lys Asp Glu Ser Gln Thr Tyr Pro Ile Leu Met Met Arg Thr Pro Tyr
 65                  70                  75                  80

Ser Ser Gln Pro Tyr Gly Asp Asn Glu Phe Lys Thr Lys Ile Gly Pro
                 85                  90                  95

Asn Val His Leu Met Lys Glu Gly Asn Ile Val Val Tyr Gln Asp Val
            100                 105                 110

Arg Gly Arg Trp Met Ser Glu Gly Val Tyr Asp Asn Met Arg Ala Tyr
        115                 120                 125

Ile Pro Asn Lys Thr Glu Asp Ser Gln Ile Asp Glu Ala Ser Asp Thr
    130                 135                 140

Tyr Asp Thr Ile Asp Trp Leu Val Asn Val Glu Asn Asn Asn Gly
145                 150                 155                 160

Asn Val Gly Thr Trp Gly Ile Ser Tyr Pro Gly Phe Tyr Ala Thr Tyr
                165                 170                 175

Ser Thr Ile Asp Ala His Pro Ala Leu Lys Ala Ser Pro Gln Ala
            180                 185                 190

Cys Ile Gly Asp Phe Phe Asp Asp Phe His His Asn Gly Ala Phe
        195                 200                 205

Leu Leu Ser Tyr Phe Arg Ala Val Ser Leu Phe Gly Thr Thr Lys Asp
    210                 215                 220

Lys Pro Thr Asp Ser Ala Trp Tyr Lys Phe Pro Glu Met Lys Thr Gln
225                 230                 235                 240

Asp Gln Tyr Gln Phe Phe Leu Asp Ala Gly Pro Leu Ser Asn Leu Asn
                245                 250                 255

Lys Tyr Phe Gln Tyr Asp Thr Pro Asp Asp Thr Ser Val Ser Lys Ser
            260                 265                 270

Asp Arg Ile Asp Asp Val Phe Trp Lys Glu Ile Val Glu His Pro Asn
        275                 280                 285

Tyr Asp Thr Ile Trp Lys Ser Lys Gly Leu Ile Gln Asn Leu Lys Asp
    290                 295                 300

Ile Lys Pro Ser Val Ala Thr Met Ile Val Gly Gly Leu Phe Asp Ala
305                 310                 315                 320

Glu Asp Leu Tyr Gly Pro Phe Glu Thr Tyr Lys Thr Ile Glu Lys His
                325                 330                 335

Asn Pro Asp Asn Tyr Asn Ile Met Val Phe Gly Pro Trp Asp His Gly
            340                 345                 350

Arg Trp Ala Arg Ser Asp Val Lys Asn Tyr Val Gly Asn Tyr Phe Phe
        355                 360                 365

Gly Asp Ser Ile Ser Leu Lys Phe Gln Arg Asp Val Glu Thr Lys Phe
    370                 375                 380

Phe Asn His Phe Leu Lys Gly Lys Gly Asp Lys Asn Ser Gly Leu Pro
385                 390                 395                 400

Glu Ala Tyr Val Phe Asp Ser Gly Lys Lys Glu Trp Ser Ser Phe Asp
                405                 410                 415

Ser Trp Pro Pro Lys Gln Ala Glu Lys Gln Ala Met Tyr Leu Asn Ala
            420                 425                 430

Asn Gln Glu Leu Ser Asp Ser Lys Lys Gly Asn Thr Ser Glu Thr Phe
        435                 440                 445

Val Ser Asp Leu Lys Arg Pro Val Pro Tyr Ser Glu Asp Ile Lys Thr
    450                 455                 460

Val Phe Thr Pro Arg Lys Tyr Met Thr Asp Asp Gln Arg Phe Ala Ala
465                 470                 475                 480

Arg Arg Pro Asp Val Leu Ile Phe Glu Thr Asp Ile Leu Glu Glu Asp
```

-continued

```
                        485                 490                 495
Ile Thr Leu Ala Gly Asp Ile Leu Ala Gln Leu Asn Val Ser Thr Thr
            500                 505                 510

Gly Thr Asp Ala Asp Trp Ile Val Lys Ile Val Asp Val His Pro Ala
            515                 520                 525

Asp Ala Glu Glu Gln Lys Glu Gly Met Gln Asp His Leu Ser Met Ser
            530                 535                 540

Asn Tyr His Leu Met Val Arg Ser Glu Val Met Arg Gly Arg Phe Arg
545                     550                 555                 560

Asn Ser Phe Glu Asn Pro Glu Pro Phe Val Pro Asn Gln Pro Thr Asp
                    565                 570                 575

Val Asn Ile Lys Leu Gln Asp Val His His Thr Phe Lys Lys Gly His
            580                 585                 590

Lys Leu Gln Val Gln Val Gln Ser Thr Trp Phe Pro Leu Ile Asp Leu
            595                 600                 605

Asn Pro Gln Thr Phe Val Pro Asn Ile Tyr Lys Ala Lys Glu Ser Asp
            610                 615                 620

Phe Lys Thr Gln Thr His Ser Val Phe Asn Asp Ser Lys Ile Glu Phe
625                     630                 635                 640

Thr Val Leu Lys
```

METHOD FOR PRODUCING α-L-ASPARTYL-L-PHENYLALANINE-β-ESTER AND METHOD FOR PRODUCING α-L-ASPARTYL-L-PHENYLALANINE-α-METHYL ESTER

CROSS-REFERENCE TO RELATED APPLICATIONS

The present application is a divisional of U.S. Ser. No. 13/198,075, filed on Aug. 4, 2011, which is a divisional of U.S. Ser. No. 12/749,966, filed on Mar. 30, 2010 (now U.S. Pat. No. 8,034,584), which is a divisional of U.S. Ser. No. 11/970,203 (now U.S. Pat. No. 7,745,172), filed on Jan. 7, 2008, which is a divisional of U.S. Ser. No. 10/876,673 (now U.S. Pat. No. 7,361,458), filed on Jun. 28, 2004, which is a continuation of PCT/JP2004/000620 filed on Jan. 23, 2004, which claims priority to JP 2003-016764, filed on Jan. 24, 2003, JP2003-201819, filed on Jul. 25, 2003, and U.S. 60/491,546, filed on Aug. 1, 2003.

TECHNICAL FIELD

The present invention relates to a method for producing an α-L-aspartyl-L-phenylalanine-β-ester (also named as "α-L-(β-o-substituted aspartyl)-L-phenylalanine (abbreviation: α-ARP)) and to a method for producing an α-L-aspartyl-L-phenylalanine-α-methyl ester (also named α-L-aspartyl-L-phenylalanine methyl ester (abbreviation: α-APM). More particularly, the present invention relates to a method for producing an α-L-aspartyl-L-phenylalanine-β-ester, which is an important intermediate for producing an α-L-aspartyl-L-phenylalanine-α-methyl ester (product name: aspartame) that is in great demand as a sweetener, and to a method for producing an α-L-aspartyl-L-phenylalanine-α-methyl ester utilizing the method for producing the α-L-aspartyl-L-phenylalanine-β-ester.

BACKGROUND ART

Conventionally known methods for producing α-L-aspartyl-L-phenylalanine-α-methyl ester (hereinafter, "α-APM" for short in some cases) include a chemical synthesis method and enzymatic synthesis method. As the chemical synthesis method, there has been known a method for condensing an N-protected L-aspartic acid anhydride with L-phenylalanine methyl ester to synthesize an N-protected APM and eliminating the N-protecting group to obtain APM, and as the enzymatic synthesis method, there has been known a method for condensing an N-protected L-aspartic acid with L-phenylalanine methyl ester to synthesize an N-protected APM and eliminating the N-protecting group to obtain APM. In both of the methods, however, steps of introducing a protecting group and eliminating the protecting group are necessary and the processes are very troublesome. On the other hand, an APM production method in which no N-protecting group is used has been studied (see Japanese Patent Publication No. H02-015196 Gazette). However, this method is not suitable for industrial production due to very low yield of the product. Thus, under such circumstances, development of industrial production methods for aspartame at lower cost has been desired.

DISCLOSURE OF INVENTION

It is an object of the present invention to provide a method for producing an α-L-aspartyl-L-phenylalanine-β-ester, which is an intermediate of an α-L-aspartyl-L-phenylalanine-α-methyl ester, easily, inexpensively and at high yield without going through a complex synthesis method. Further, it is an object of the present invention to provide a method for producing an α-L-aspartyl-L-phenylalanine-α-methyl ester easily, inexpensively, and at high yield.

As a result of conducting extensive research in consideration of the above objects, the inventors of the present invention have found that a newly discovered enzyme or an enzyme-containing substance is capable of selectively producing an α-L-aspartyl-L-phenylalanine-β-ester from an L-aspartic acid-α,β-diester and L-phenylalanine, and have achieved the present invention.

Namely, the present invention is as described below.

[1] A method of producing an α-L-aspartyl-L-phenylalanine-β-ester (i.e., α-L-(β-o-substituted aspartyl)-L-phenylalanine), comprising forming the α-L-aspartyl-L-phenylalanine-β-ester from L-aspartic acid-α,β-diester and L-phenylalanine using an enzyme or enzyme-containing substance that has an ability to selectively link L-phenylalanine to an α-ester site of the L-aspartic acid-α,β-diester through a peptide bond.

[2] The method for producing an α-L-aspartyl-L-phenylalanine-β-ester (i.e., α-L-(β-o-substituted aspartyl)-L-phenylalanine) according to [1] above, wherein the enzyme or enzyme-containing substance is one type or two or more types selected from the group consisting of a culture of a microbe that has an ability to selectively link L-phenylalanine to an α-ester site of the L-aspartic acid-α,β-diester through a peptide bond, a microbial cell separated from the culture and a treated microbial cell product of the microbe.

[3] The method for producing an α-L-aspartyl-L-phenylalanine-β-ester (i.e., α-L-(β-o-substituted aspartyl)-L-phenylalanine) according to [2] above, wherein the microbe is a microbe belonging to a genus selected from the group consisting of *Aeromonas, Azotobacter, Alcaligenes, Brevibacterium, Corynebacterium, Escherichia, Empedobacter, Flavobacterium, Microbacterium, Propionibacterium, Brevibacillus, Paenibacillus, Pseudomonas, Serratia, Stenotrophomonas, Sphingobacterium, Streptomyces, Xanthomonas, Williopsis, Candida, Geotrichum, Pichia, Saccharomyces, Torulaspora, Cellulophaga, Weeksella, Pedobacter, Persicobacter, Flexithrix, Chitinophaga, Cyclobacterium, Runella, Thermonema, Psychroserpens, Gelidibacter, Dyadobacter, Flammeovirga, Spirosoma, Flectobacillus, Tenacibaculum, Rhodotermus, Zobellia, Muricauda, Salegentibacter, Taxeobacter, Cytophaga, Marinilabilia, Lewinella, Saprospira*, and *Haliscomenobacter*.

[4] The method for producing an α-L-aspartyl-L-phenylalanine-β-ester (i.e., α-L-(β-o-substituted aspartyl)-L-phenylalanine) according to [2] above, wherein the microbe is a transformed microbe that is capable of expressing a protein (A) or (B):

(A) a protein having an amino acid sequence consisting of amino acid residues numbers 23 to 616 of an amino acid sequence described in SEQ ID NO: 6 of the Sequence Listing, (B) a protein having an amino acid sequence including substitution, deletion, insertion, addition, and/or inversion of one or a plurality of amino acids in the amino acid sequence consisting of amino acid residues 23 to 616 of the amino acid sequence described in SEQ ID NO: 6 of the Sequence Listing, and having activity to selectively link L-phenylalanine to an α-ester site of the L-aspartic acid-α,β-diester through a peptide bond.

[5] The method for producing an α-L-aspartyl-L-phenylalanine-β-ester (i.e., α-L-(β-o-substituted aspartyl)-L-phenylalanine) according to [2], wherein the microbe is a transformed microbe that is capable of expressing a protein (C) or (D):
  (C) a protein having an amino acid sequence consisting of amino acid residues numbers 21 to 619 of an amino acid sequence described in SEQ ID NO: 12 of the Sequence Listing,
  (D) a protein having an amino acid sequence including substitution, deletion, insertion, addition, and/or inversion of one or a plurality of amino acids in the amino acid sequence consisting of amino acid residues 21 to 619 of the amino acid sequence described in SEQ ID NO: 12 of the Sequence Listing, and having activity to selectively link L-phenylalanine to an α-ester site of the L-aspartic acid-α,β-diester through a peptide bond.

[6] The method for producing an α-L-aspartyl-L-phenylalanine-β-ester (i.e., α-L-(β-o-substituted aspartyl)-L-phenylalanine) according to [2], wherein the microbe is a transformed microbe that is capable of expressing a protein (E) or (F) below:
  (E) a protein having an amino acid sequence consisting of amino acid residues numbers 23 to 625 of an amino acid sequence described in SEQ ID NO: 18 of the Sequence Listing,
  (F) a protein having an amino acid sequence including substitution, deletion, insertion, addition, and/or inversion of one or a plurality of amino acids in the amino acid sequence consisting of amino acid residues 23 to 625 of the amino acid sequence described in SEQ ID NO: 18 of the Sequence Listing, and having activity to selectively link L-phenylalanine to an α-ester site of the L-aspartic acid-α,β-diester through a peptide bond.

[7] The method for producing an α-L-aspartyl-L-phenylalanine-β-ester (i.e., α-L-(β-o-substituted aspartyl)-L-phenylalanine) according to [2] above, wherein the microbe is a transformed microbe that is capable of expressing a protein (G) or (H) below:
  (G) a protein having an amino acid sequence consisting of amino acid residues numbers 23 to 645 of an amino acid sequence described in SEQ ID NO: 23 of the Sequence Listing,
  (H) a protein having an amino acid sequence including substitution, deletion, insertion, addition, and/or inversion of one or a plurality of amino acids in the amino acid sequence consisting of amino acid residues 23 to 645 of the amino acid sequence described in SEQ ID NO: 23 of the Sequence Listing, and having activity to selectively link L-phenylalanine to an α-ester site of the L-aspartic acid-α,β-diester through a peptide bond.

[8] The method for producing an α-L-aspartyl-L-phenylalanine-β-ester (i.e., α-L-(β-o-substituted aspartyl)-L-phenylalanine) according to [2], wherein the microbe is a transformed microbe that is capable of expressing a protein (I) or (J) below:
  (I) a protein having an amino acid sequence consisting of amino acid residues numbers 26 to 620 of an amino acid sequence described in SEQ ID NO: 25 of the Sequence Listing,
  (J) a protein having an amino acid sequence including substitution, deletion, insertion, addition, and/or inversion of one or a plurality of amino acids in the amino acid sequence consisting of amino acid residues 26 to 620 of the amino acid sequence described in SEQ ID NO: 25 of the Sequence Listing, and having activity to selectively link L-phenylalanine to an α-ester site of the L-aspartic acid-α,β-diester through a peptide bond.

[9] The method for producing an α-L-aspartyl-L-phenylalanine-β-ester (i.e., α-L-(β-o-substituted aspartyl)-L-phenylalanine) according to [2] above, wherein the microbe is a transformed microbe that is capable of expressing a protein (K) or (L) below:
  (K) a protein having an amino acid sequence consisting of amino acid residues numbers 18 to 644 of an amino acid sequence described in SEQ ID NO: 27 of the Sequence Listing,
  (L) a protein having an amino acid sequence including substitution, deletion, insertion, addition, and/or inversion of one or a plurality of amino acids in the amino acid sequence consisting of amino acid residues 18 to 644 of the amino acid sequence described in SEQ ID NO: 27 of the Sequence Listing, and having activity to selectively link L-phenylalanine to an α-ester site of the L-aspartic acid-α,β-diester through a peptide bond.

[10] The method for producing an α-L-aspartyl-L-phenylalanine-β-ester (i.e., α-L-(β-o-substituted aspartyl)-L-phenylalanine) according to [2], wherein the microbe is a transformed microbe that is capable of expressing a protein (M) or (N) below:
  (M) a protein having an amino acid sequence described in SEQ ID NO: 6 of the Sequence Listing,
  (N) a protein containing a mature protein region, having an amino acid sequence including substitution, deletion, insertion, addition, and/or inversion of one or a plurality of amino acids in the amino acid sequence described in SEQ ID NO: 6 of the Sequence Listing, and having activity to selectively link L-phenylalanine to an α-ester site of the L-aspartic acid-α,β-diester through a peptide bond.

[11] The method for producing an α-L-aspartyl-L-phenylalanine-β-ester (i.e., α-L-(β-o-substituted aspartyl)-L-phenylalanine) according to [2], wherein the microbe is a transformed microbe that is capable of expressing a protein (O) or (P) below:
  (O) a protein having an amino acid sequence described in SEQ ID NO: 12 of the Sequence Listing,
  (P) a protein containing a mature protein region, having an amino acid sequence including substitution, deletion, insertion, addition, and/or inversion of one or a plurality of amino acids in the amino acid sequence described in SEQ ID NO: 12 of the Sequence Listing, and having activity to selectively link L-phenylalanine to an α-ester site of the L-aspartic acid-α,β-diester through a peptide bond.

[12] The method for producing an α-L-aspartyl-L-phenylalanine-β-ester (i.e., α-L-(β-o-substituted aspartyl)-L-phenylalanine) according to claim 2, wherein the microbe is a transformed microbe that is capable of expressing a protein (Q) or (R) below:
  (Q) a protein containing a mature protein region, having an amino acid sequence described in SEQ ID NO: 18 of the Sequence Listing,
  (R) a protein having an amino acid sequence including substitution, deletion, insertion, addition, and/or inversion of one or a plurality of amino acids in the amino acid sequence described in SEQ ID NO: 18 of the Sequence Listing, and having activity to selectively link L-phenylalanine to an α-ester site of the L-aspartic acid-α,β-diester through a peptide bond.

[13] The method for producing an α-L-aspartyl-L-phenylalanine-β-ester (i.e., α-L-(β-o-substituted aspartyl)-L-phenylalanine) according to [3], wherein the microbe is a transformed microbe that is capable of expressing a protein (S) or (T) below:
(S) a protein having an amino acid sequence described in SEQ ID NO: 23 of the Sequence Listing,
(T) a protein containing a mature protein region, having an amino acid sequence including substitution, deletion, insertion, addition, and/or inversion of one or a plurality of amino acids in the amino acid sequence described in SEQ ID NO: 23 of the Sequence Listing, and having activity to selectively link L-phenylalanine to an α-ester site of the L-aspartic acid-α,β-diester through a peptide bond.

[14] The method for producing an α-L-aspartyl-L-phenylalanine-β-ester (i.e., α-L-(β-o-substituted aspartyl)-L-phenylalanine) according to [2], wherein the microbe is a transformed microbe that is capable of expressing a protein (U) or (V) below:
(U) a protein having an amino acid sequence described in SEQ ID NO: 25 of the Sequence Listing,
(V) a protein containing a mature protein region, having an amino acid sequence including substitution, deletion, insertion, addition, and/or inversion of one or a plurality of amino acids in the amino acid sequence described in SEQ ID NO: 25 of the Sequence Listing, and having activity to selectively link L-phenylalanine to an α-ester site of the L-aspartic acid-α,β-diester through a peptide bond.

[15] The method for producing an α-L-aspartyl-L-phenylalanine-β-ester (i.e., α-L-(β-o-substituted aspartyl)-L-phenylalanine) according to [2] above, wherein the microbe is a transformed microbe that is capable of expressing a protein (W) or (X) below:
(W) a protein having an amino acid sequence described in SEQ ID NO: 27 of the Sequence Listing,
(X) a protein containing a mature protein region, having an amino acid sequence including substitution, deletion, insertion, addition, and/or inversion of one or a plurality of amino acids in the amino acid sequence described in SEQ ID NO: 27 of the Sequence Listing, and having activity to selectively link L-phenylalanine to an α-ester site of the L-aspartic acid-α,β-diester through a peptide bond.

[16] The method for producing an α-L-aspartyl-L-phenylalanine-β-ester (i.e., α-L-(β-o-substituted aspartyl)-L-phenylalanine) according to [1] above, wherein the enzyme is at least one selected from the group consisting (A) to (X) below:
(A) a protein having an amino acid sequence consisting of amino acid residues numbers 23 to 616 of an amino acid sequence described in SEQ ID NO: 6 of the Sequence Listing,
(B) a protein having an amino acid sequence including substitution, deletion, insertion, addition, and/or inversion of one or a plurality of amino acids in the amino acid sequence consisting of amino acid residues numbers 23 to 616 of the amino acid sequence described in SEQ ID NO: 6 of the Sequence Listing, and having activity to selectively linking L-phenylalanine to an α-ester site of the L-aspartic acid-α,β-diester through a peptide bond,
(C) a protein having the amino acid sequence consisting of amino acid residue numbers 21 to 619 of an amino acid sequence described in SEQ ID NO: 12 of the Sequence Listing,
(D) a protein having an amino acid sequence including substitution, deletion, insertion, addition, and/or inversion of one or a plurality of amino acids in the amino acid sequence consisting of amino acid residue numbers 21 to 619 of the amino acid sequence described in SEQ ID NO: 12 of the Sequence Listing, and having activity to selectively linking L-phenylalanine to an α-ester site of the L-aspartic acid-α,β-diester through a peptide bond,
(E) a protein having the amino acid sequence consisting of amino acid residues numbers 23 to 625 of an amino acid sequence described in SEQ ID NO: 18 of the Sequence Listing,
(F) a protein having an amino acid sequence including substitution, deletion, insertion, addition, and/or inversion of one or a plurality of amino acids in the amino acid sequence consisting of amino acid residues numbers 23 to 625 of the amino acid sequence described in SEQ ID NO: 18 of the Sequence Listing, and having activity to selectively linking L-phenylalanine to an α-ester site of the L-aspartic acid-α,β-diester through a peptide bond,
(G) a protein having an amino acid sequence consisting of amino acid residues numbers 23 to 645 of an amino acid sequence described in SEQ ID NO: 23 of the Sequence Listing,
(H) a protein having an amino acid sequence including substitution, deletion, insertion, addition, and/or inversion of one or a plurality of amino acids in the amino acid sequence consisting of amino acid residues numbers 23 to 645 of the amino acid sequence described in SEQ ID NO: 23 of the Sequence Listing, and activity to selectively linking L-phenylalanine to an α-ester site of the L-aspartic acid-α,β-diester through a peptide bond,
(I) a protein having an amino acid sequence consisting of amino acid residues numbers 26 to 620 of an amino acid sequence described in SEQ ID NO: 25 of the Sequence Listing,
(J) a protein having an amino acid sequence including substitution, deletion, insertion, addition, and/or inversion of one or a plurality of amino acids in the amino acid sequence consisting of amino acid residues numbers 26 to 620 of the amino acid sequence described in SEQ ID NO: 25 of the Sequence Listing, and having activity to selectively linking L-phenylalanine to an α-ester site of the L-aspartic acid-α,β-diester through a peptide bond,
(K) a protein having an amino acid sequence consisting of amino acid residues numbers 18 to 644 of an amino acid sequence described in SEQ ID NO: 27 of the Sequence Listing,
(L) a protein having an amino acid sequence including substitution, deletion, insertion, addition, and/or inversion of one or a plurality of amino acids in the amino acid sequence consisting of amino acid residues numbers 18 to 644 of the amino acid sequence described in SEQ ID NO: 27 of the Sequence Listing, and having activity to selectively linking L-phenylalanine to an α-ester site of the L-aspartic acid-α,β-diester through a peptide bond,
(M) a protein having an amino acid sequence described in SEQ ID NO: 6 of the Sequence Listing,
(N) a protein containing a mature protein region, having an amino acid sequence including substitution, deletion, insertion, addition, and/or inversion of one or a plurality of amino acids in the amino acid sequence described in SEQ ID NO: 6 of the Sequence Listing, and activity to selectively linking L-phenylalanine to an α-ester site of the L-aspartic acid-α,β-diester through a peptide bond,
(O) a protein having the amino acid sequence described in SEQ ID NO: 12 of the Sequence Listing,
(P) a protein containing a mature protein region, having an amino acid sequence including substitution, deletion, insertion, addition, and/or inversion of one or a plurality of amino acids in the amino acid sequence described in SEQ ID NO: 12 of the Sequence Listing, and activity to selectively linking L-phenylalanine to an α-ester site of the L-aspartic acid-α,β-diester through a peptide bond, (Q) a protein having an amino acid sequence described in SEQ ID NO: 18 of the Sequence Listing, (R) a protein containing a mature protein region, having an amino acid sequence including substitution, deletion, insertion, addition, and/or inversion of one or a plurality of amino acids in the amino acid sequence described in SEQ ID NO: 18 of the Sequence Listing, and activity to selectively linking L-phenylalanine to an α-ester site of the L-aspartic acid-α,β-diester through a peptide bond, (S) a protein having an amino acid sequence described in SEQ ID NO: 23 of the Sequence Listing, (T) a protein containing a mature protein region, having an amino acid sequence including substitution, deletion, insertion, addition, and/or inversion of one or a plurality of amino acids in the amino acid sequence described in SEQ ID NO: 23 of the Sequence Listing, and activity to selectively linking L-phenylalanine to an α-ester site of the L-aspartic acid-α,β-diester through a peptide bond, (U) a protein having an amino acid sequence described in SEQ ID NO: 25 of the Sequence Listing, (V) a protein containing a mature protein region, having an amino acid sequence including substitution, deletion, insertion, addition, and/or inversion of one or a plurality of amino acids in the amino acid sequence described in SEQ ID NO: 25 of the Sequence Listing, and activity to selectively linking L-phenylalanine to an α-ester site of the L-aspartic acid-α,β-diester through a peptide bond, (W) a protein having an amino acid sequence described in SEQ ID NO: 27 of the Sequence Listing, and (X) a protein containing a mature protein region, having an amino acid sequence in the amino acid sequence described in SEQ ID NO: 27 of the Sequence Listing, and having activity to selectively linking L-phenylalanine to an α-ester site of the L-aspartic acid-α,β-diester through a peptide bond.

[17] The method of producing an α-L-aspartyl-L-phenylalanine-α-methyl ester (i.e., α-L-aspartyl-L-phenylalanine methyl ester), comprising: a reaction step of synthesizing an α-L-aspartyl-L-phenylalanine-β-methyl ester (also named α-L-(β-o-methyl aspartyl)-L-phenylalanine (abbreviation: α-AMP)) by a method of producing an α-L-aspartyl-L-phenylalanine-β-ester according to any one of claims 1 to 16; and a reaction step of converting the α-L-aspartyl-L-phenylalanine-β-methyl ester (i.e., α-L-(β-o-methyl aspartyl)-L-phenylalanine) to α-L-aspartyl-L-phenylalanine-α-methyl ester.

By the present invention, α-L-aspartyl-L-phenylalanine-β-ester can be easily produced. By the method of the present invention, α-L-aspartyl-L-phenylalanine-β-ester can be produced easily and at high yield with reduced use of complicated synthetic methods such as introduction/elimination of protecting groups.

Furthermore, by the present invention, α-L-aspartyl-L-phenylalanine-α-methyl ester can be produced easily, at high yield, and inexpensively.

The other objects, features and advantages of the present invention are specifically set forth in or will become apparent from the following detailed descriptions of the invention when read in conjunction with the accompanying drawing.

BRIEF DESCRIPTION OF THE DRAWING

FIG. 1 is a diagram showing amounts of enzymes that exist in a cytoplasm fraction (Cy) and a periplasm fraction (Pe).

BEST MODE FOR CARRYING OUT THE INVENTION

Hereinafter, the present invention will be described in the order of
<1> Method of producing α-L-aspartyl-L-phenylalanine-β-ester
1. Method of producing α-L-aspartyl-L-phenylalanine-β-ester
2. Microbes used in the present invention
3. Enzymes used in the present invention; and
<2> Method of producing α-L-aspartyl-L-phenylalanine-α-methyl ester.
<1> Method of producing α-L-aspartyl-L-phenylalanine-β-ester
1. Method of producing α-L-aspartyl-L-phenylalanine-β-ester In the method of producing α-L-aspartyl-L-phenylalanine-β-ester of the present invention (hereinafter also called "the production method of a peptide of the present invention"), L-phenylalanine and L-aspartic acid-α,β-diester are allowed to react in the presence of an enzyme having a stated peptide forming activity. That is, in the production method of a peptide of the present invention, an α-L-aspartyl-L-phenylalanine-β-ester is formed from an L-aspartic acid-α,β-diester and L-phenylalanine using an enzyme or enzyme-containing substance capable of selectively linking L-phenylalanine to the α-ester site of L-aspartic acid-α,β-diester through a peptide bond. The enzyme or enzyme-containing substance capable of selectively linking L-phenylalanine to the α-ester site of a L-aspartic acid-α,β-diester refers to an enzyme or enzyme-containing substance having an ability or activity to catalyze a reaction in which substantially, L-phenylalanine is able to perform no nucleophilic attack to a β-ester site of L-aspartic acid-α,β-diester but performs a nucleophilic attack on an α-ester site thereof only. As shown in the reference example hereinbelow, however, an enzyme or enzyme-containing substance has also been obtained that has an ability to catalyze a reaction in which substantially, L-phenylalanine is able to perform no attack on the α-ester site of an L-aspartic acid-α,β-diester but performs nucleophilic attack on the β-ester site thereof only, contrary to the above-mentioned ability, and that produces a β-L-aspartyl-L-phenylalanine-α-ester (also named β-L-(α-o-substituted aspartyl)-L-phenylalanine (abbreviation: β-ARP) from the L-aspartic acid-α,β-diester and L-phenylalanine.

The reaction formula in which L-phenylalanine performs nucleophilic attack on the α-ester site of L-aspartic acid-α,β-diester to produce an α-L-aspartyl-L-phenylalanine-β-ester (α-ARP) is shown in the following formula (I-α) (wherein "Me" represents a methyl group) by citing the case where L-aspartic acid-α,β-dimethyl ester is used as the L-aspartic acid-α,β-diester. As shown in the formula (I-α), in the peptide production method of the present invention, the amino group of L-phenylalanine reacts with the α-methyl ester site of the L-aspartic acid-α,β-dimethyl ester to form a peptide bond. On the other hand, the following formula (I-β) indicates a reaction in which the β-methyl ester site of L-aspartic acid-α,β-dimethyl ester undergoes nucleophilic attack to form β-L-aspartyl-L-phenylalanine-α-methyl ester (also named β-L-(α-o-methyl aspartyl)-L-phenylalanine (abbreviation: β-AMP)). The peptide bond in β-AMP is formed at the β-methyl ester site of the L-aspartic acid-α,β-dimethyl ester. The enzyme or enzyme-containing substance used in the present invention accelerates substantially only a reaction as in the formula (I-α) but causes substantially no reaction as in the formula (I-β). α-APM can be produced from α-AMP through a simple reaction step (formula (II)), but α-APM cannot be produced directly from β-AMP. That is, the method of the present invention is extremely efficient as a method for producing an intermediate of α-APM and is useful for industrial production.

Reaction formula I-α

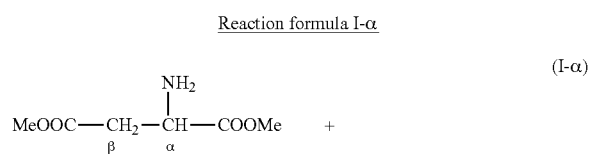

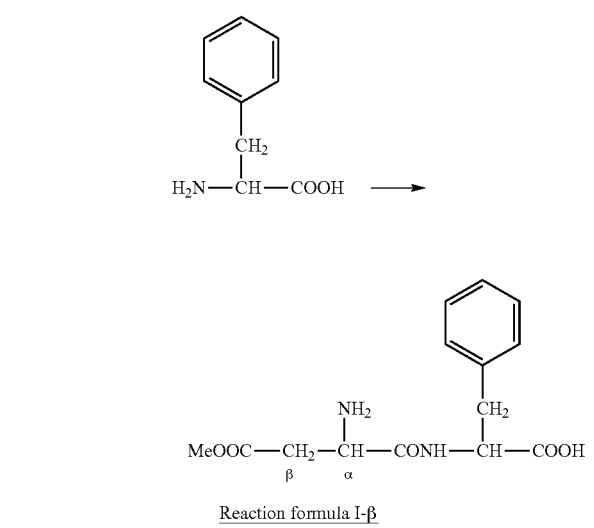

Reaction formula I-β

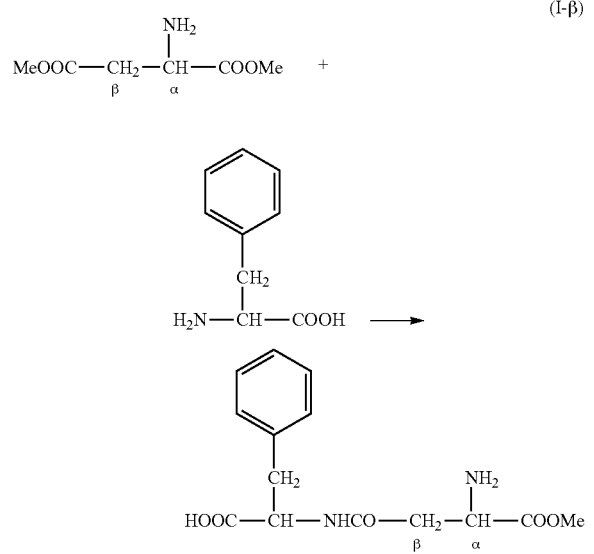

-continued
Reaction formula II

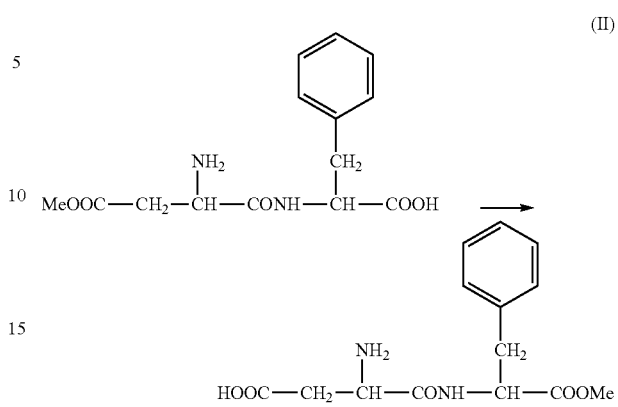

A method for allowing the enzyme or enzyme-containing substance to act on L-aspartic acid-α,β-diester and L-phenylalanine may be performed by mixing the enzyme or enzyme-containing substance with L-aspartic acid-α,β-diester and L-phenylalanine. More specifically, there may be used a method in which the enzyme or enzyme-containing substance is added to a solution containing an L-aspartic acid-diester and L-phenylalanine to effect reaction. When a microbe which produces the enzyme is used as the enzyme-containing substance, either the reaction may be carried out as described above, or a method which includes culturing a microbe that produces the enzyme to produce and accumulate the enzyme in the microbe or a culture liquid in which the microbe has been cultured, and adding an L-aspartic acid-α,β-diester and L-phenylalanine to the culture liquid, or the like method may be used. The thus produced α-L-aspartyl-L-phenylalanine-β-ester is recovered according to the conventional method and it can be purified, if necessary.

The "enzyme-containing substance" may be any substance so far as it contains the enzyme, and specific modes thereof include a culture of a microbe which produces the enzyme, a microbial cell separated from the culture and a treated microbial cell product of the microbe. The culture of microbe means a substance obtained by culturing a microbe, and specifically means a mixture of microbial cell, a medium used for culturing the microbe and a substance produced by the cultured microbe, and so forth. In addition, the microbial cell may be washed to use as a washed microbial cell. Moreover, the treated microbial cell product includes those obtained by subjecting the microbial cell to crushing, lysis, or freeze-drying, and further a crude enzyme recovered by treating the microbial cell and a purified enzyme obtained by further purification. As the purification-treated enzyme, a partially purified enzyme obtained by various purification methods and so forth may be used. In addition, immobilized enzymes which have been immobilized by a covalent bonding method, an adsorption method, an entrapment method, or the like may be used. Further, for some microbes to be used, a portion of the microbial cells may undergo lysis during culturing and in such a case, the supernatant of the culture liquid may be utilized as the enzyme-containing substance as well.

In addition, as the microbe that contains the enzyme, a wild strain may be used or a gene recombinant strain in which the enzyme has been expressed may be used. Such microbe is not limited to an enzyme microbial cell but the treated microbial cell products such as acetone-treated microbial cell and freeze-dried microbial cell may be used. Further, immobilized microbial cells obtained by immobilizing the treated microbial cell product using a covalent bonding method, an adsorption method, an entrapment method, or the like, or an immobilized treated microbial cell product may be used.

Use of a wild strain which is able to produce a peptide forming enzyme having an activity to form an α-L-aspartyl-L-phenylalanine-β-ester is preferred in that peptide production can be performed more readily without going through a step of making a gene recombinant strain. On the other hand, a gene recombinant strain which has been transformed so as to express a peptide forming enzyme having an activity to produce an α-L-aspartyl-L-phenylalanine-β-ester can be modified such that the peptide forming enzyme is produced in a larger amount. Thus, it is possible to synthesize an α-L-aspartyl-L-phenylalanine-β-ester in a larger amount and at a higher rate. Culturing a microbe of wild strain or gene recombinant strain in a medium to accumulate the peptide forming enzyme in the medium and/or microbe, and mixing the thus accumulated product with an L-aspartic acid-α,β-diester and L-phenylalanine can form an α-L-aspartyl-L-phenylalanine-β-ester.

Note that when cultured products, cultured microbial cells, washed microbial cells and treated microbial cell products obtained by subjecting microbial cells to crushing or lysis are used, it is often the case that an enzyme exists that decomposes the formed α-L-aspartyl-L-phenylalanine-β-ester without being involved in the formation of the α-L-aspartyl-L-phenylalanine-β-ester. In such a case, it is preferred in some occasions to add a metal protease inhibitor such as ethylenediaminetetraacetic acid (EDTA). The addition amount is in the range of 0.1 millimolar (mM) to 300 mM, preferably 1 mM to 100 mM.

The amount of enzyme or enzyme-containing substance used may be enough if it is an amount at which the target effect is demonstrated (effective amount). While a person with ordinary skill in the art can easily determine this effective amount through simple, preliminary experimentation, the use amount is, for example, about 0.01 to about 100 units ("U") in the case of using enzyme, and about 0.1 to about 500 g/L in the case of using washed microbial cells. Note that 1 U is defined to be an amount of enzyme which allows production of 1 micromole (μmole) of L-α-aspartyl-L-phenylalanine-β-methyl ester from 100 mM L-aspartic acid-α,β-dimethyl ester and 200 mM L-phenylalanine at 25° C. in one minute.

The L-aspartic acid-α,β-diester to be used in the reaction may be any one that is condensed with L-phenylalanine to produce an α-L-aspartyl-L-phenylalanine-βester. Examples of the L-aspartic acid-α,β-diester include L-aspartic acid-α,β-dimethyl ester and L-aspartic acid-α,β-diethyl ester. When L-aspartic acid-α,β-dimethyl ester and L-phenylalanine are allowed to react, α-L-aspartyl-L-phenylalanine-β-methyl ester (α-AMP) is produced, and when L-aspartic acid-α,β-diethyl ester and L-phenylalanine are reacted, α-L-aspartyl-L-phenylalanine-β-ethyl ester (also named α-L-(β-o-ethyl aspartyl)-L-phenylalanine (abbreviation: α-AEP)) is produced.

While the concentrations of L-aspartic acid-α,β-diester and L-phenylalanine serving as starting materials are each 1 mM to 10 mM, and preferably 0.05 M to 2 M, there may be cases in which it is preferable to add either one of the substrates in an equimolar amount or more with respect to the other substrate, and selection is made as necessary. In addition, in cases where high concentrations of substrates inhibit the reaction, these can be adjusted to concentrations that do not cause inhibition and successively added during the reaction.

The reaction temperature that allows production of α-L-aspartyl-L-phenylalanine-β-ester is 0 to 60° C., and preferably 5 to 40° C. In addition, the reaction pH that allows production of α-L-aspartyl-L-phenylalanine-β-ester is 6.5 to 10.5, and preferably 7.0 to 10.0.

2. Microbes Used in the Present Invention

As the microbes to be used in the present invention, those microbes which have an ability to produce α-L-aspartyl-L-phenylalanine-β-ester from an L-aspartic acid-α,β-diester and L-phenylalanine may be used without particular limitation. The microbes that have an ability to produce α-L-aspartyl-L-phenylalanine-β-ester from an L-aspartic acid-α,β-diester and L-phenylalanine include, for example, microbes belonging to the genera *Aeromonas, Azotobacter, Alcaligenes, Brevibacterium, Corynebacterium, Escherichia, Empedobacter, Flavobacterium, Microbacterium, Propionibacterium, Brevibacillus, Paenibacillus, Pseudomonas, Serratia, Stenotrophomonas, Sphingobacterium, Streptomyces, Xanthomonas, Williopsis, Candida, Geotrichum, Pichia, Saccharomyces, Torulaspora, Cellulophaga, Weeksella, Pedobacter, Persicobacter, Flexithrix, Chitinophaga, Cyclobacterium, Runella, Thermonema, Psychroserpens, Gelidibacter, Dyadobacter, Flammeovirga, Spirosoma, Flectobacillus, Tenacibaculum, Rhodotermus, Zobellia, Muricauda, Salegentibacter, Taxeobacter, Cytophaga, Marinilabilia, Lewinella, Saprospira*, and *Haliscomenobacter*.

Specifically, the following may be exemplified.

*Aeromonas hydrophila* ATCC 13136
*Azotobacter vinelandii* IFO 3741
*Alcaligenes faecalis* FERM P-8460
*Brevibacterium minutiferuna* FERM BP-8277
*Corynebacterium flavescens* ATCC 10340
*Escherichia coli* FERM BP-8276
*Empedobacter brevis* ATCC 14234
*Flavobacterium resinovorum* ATCC 14231
*Microbacterium arborescens* ATCC 4348
*Propionibacterium shermanii* FERM BP-8100
*Brevibacillus parabrevis* ATCC 8185
*Paenibacillus alvei* IFO 14175
*Pseudomonas fragi* IFO 3458
*Serratia grimesii* ATCC 14460
*Stenotrophomonas maltophilia* ATCC 13270
*Sphingobacterium* sp. FERM BP-8124
*Streptomyces griseolus* NRRL B-1305 (*Streptomyces lavendulae*)
*Xanthomonas maltophilia* FERM BP-5568
*Williopsis saturnus* IFO 0895
*Candida magnoliae* IFO 0705
*Geotrichum* fragrance CBS 152.25 (*Geotrichum amycelium*)
*Geotrichum amycelium* IFO 0905
*Pichia ciferrii* IFO 0905
*Saccharomyces unisporus* IFO 0724
*Torulaspora delbrueckii* IFO 0422
*Cellulophaga lytica* NBRC 14961
*Weeksella virosa* NBRC 16016
*Pedobacter heparinus* NBRC 12017
*Persicobacter diffluens* NBRC 15940
*Flexithrix dorotheae* NBRC 15987
*Chitinophaga pinensis* NBRC 15968
*Cyclobacterium marinum* ATCC 25205
*Runella slithyformis* ATCC 29530
*Thermonema lapsum* ATCC 43542
*Psychroserpens burtonensis* ATCC 700359
*Gelidibacter algens* ATCC 700364
*Dyadobacter fermentans* ATCC 700827
*Flammeovirga aprica* NBRC 15941

*Spirosoma linguale* DSMZ 74
*Flectobacillus major* DSMZ 103
*Tenacibaculum maritimum* ATCC 43398
*Rhodotermus marinus* DSMZ 4252
*Zobellia galactanivorans* DSMZ 12802
*Muricauda ruestringensis* DSMZ 13258
*Salegentibacter salegens* DSMZ 5424
*Taxeobacter gelupurpurascens* DSMZ 11116
*Cytophaga hutchinsonii* NBRC 15051
*Marinilabilia salmonicolor* NBRC 15948
*Lewinella cohaerens* ATCC 23123
*Saprospira grandis* ATCC 23119
*Haliscomenobacter hydrossis* ATCC 27775

Among the aforementioned strains of microbes, those microbes described with FERM numbers have been deposited at the independent administrative corporation, National Institute of Advanced Industrial Science and Technology, International Patent Organism Depositary (Chuo Dai-6, 1-1 Higashi 1-Chome, Tsukuba-shi, Ibaraki-ken, Japan), and can be furnished by referring to each number.

Among the aforementioned strains of microbes, those microbes described with ATCC numbers have been deposited at the American Type Culture Collection (P.O. Box 1549, Manassas, Va. 20110, the United States of America), and can be furnished by referring to each number.

Among the aforementioned strains of microbes, those microbes described with IFO numbers have been deposited at the Institute of Fermentation, Osaka (2-17-85 Jusanbon-cho, Yodogawa-ku, Osaka-shi, Japan), and can be furnished by referring to each number.

Among the aforementioned strains of microbes, those microbes described with NBRC numbers have been deposited at the NITE Biological Resource Center of the National Institute of Technology and Evaluation (5-8 Kazusa-Kamaashi 2-Chome, Kisarazu-shi, Chiba-ken, Japan), and can be furnished by referring to each number.

Among the aforementioned strains of microbes, those microbes described with DSMZ numbers have been deposited at the Deutche Sammlung von Mikroorganismen and Zellkulturen GmbH (German Collection of Microbes and Cell Cultures) (Mascheroder Weg 1b, 38124 Braunschweig, Germany), and can be furnished by referring to each number.

Like the aforementioned strains, those microbes described with FERM numbers are microbes that were deposited at the independent administrative corporation, National Institute of Advanced Industrial Science and Technology, International Patent Organism Depositary (Chuo Dai-6, 1-1 Higashi 1-Chome, Tsukuba-shi, Ibaraki-ken, 305-8566 Japan). *Alcaligenes faecalis* FERM P-8460 is a microbe that was deposited on Sep. 30, 1985 and assigned the deposit number FERM P-8460. *Propionibacterium shermanii* FERM P-9737 is a microbe that was originally deposited on Dec. 4, 1987 and control of this organism was subsequently transferred to international deposition under the provisions of the Budapest Treaty on Jul. 1, 2002 and was assigned the deposit number of FERM BP-8100. *Xanthomonas maltophilia* FERM BP-5568 is a microbe that was originally deposited on Jun. 14, 1995 and control of this organism was subsequently transferred to international deposition under the provisions of the Budapest Treaty on Jun. 14, 1996. *Brevibacterium minutiferuna* FERM BP-8277 was internationally deposited under the provisions of Budapest Treaty on Jan. 20, 2002. *Escherichia coli* FERM BP-8276 was deposited at an international depositary institution under the provisions of Budapest Treaty on Jan. 20, 2002.

*Empedobacter brevis* strain ATCC 14234 (strain FERM P-18545, strain FERM BP-8113) was deposited at the International Patent Organism Depositary of the independent administrative corporation, National Institute of Advanced Industrial Science and Technology (Chuo Dai-6, 1-1 Higashi 1-Chome, Tsukuba-shi, Ibaraki-ken, Japan) on Oct. 1, 2001 and assigned the deposit number of FERM P-18545. Control of this organism was subsequently transferred to deposition under the provisions of the Budapest Treaty at the International Patent Organism Depositary of the independent administrative corporation, National Institute of Advanced Industrial Science and Technology on Jul. 8, 2002 and was assigned the deposit number of FERM BP-8113 (indication of microbe: *Empedobacter brevis* strain AJ 13933).

*Sphingobacterium* sp. strain AJ 110003 was deposited at the International Patent Organism Depositary of the independent administrative corporation, National Institute of Advanced Industrial Science and Technology (Address of depositary institution: Chuo Dai-6, 1-1 Higashi 1-Chome, Tsukuba-shi, Ibaraki-ken, Japan) on Jul. 22, 2002, and was assigned the deposit number of FERM BP-8124.

Note that the strain AJ 110003 (FERM BP-8124) was identified to be the aforementioned *Sphingobacterium* sp. by the identification experiment described below. The strain FERM BP-8124 is a Gram-negative rod (0.7 to 0.8×1.5 to 2.0 µm) that forms no spore and is not motile. Its colonies are round with a completely smooth border, contain low protrusions and have a glossy, light yellow color. The organism grows at 30° C. and is catalase positive, oxidase positive and negative for the OF test (glucose), and was identified as a bacterium belonging to the genus *Sphingobacterium* based on these properties. Moreover, because of the properties that it is negative for nitrate reduction, negative for indole production, negative for acid production from glucose, arginine dihydrolase negative, urease positive, esculin hydrolysis positive, gelatin hydrolysis negative, β-galactosidase positive, glucose assimilation positive, L-arabinose assimilation negative, D-mannose assimilation positive, D-mannitol assimilation negative, N-acetyl-D-glucosamine assimilation positive, maltose assimilation positive, potassium gluconate assimilation negative, n-capric acid assimilation negative, adipic acid assimilation negative, dl-malic acid assimilation negative, sodium citrate assimilation negative, phenyl acetate assimilation negative and cytochrome oxidase positive, it was determined to have properties that are similar to those of *Sphingobacterium multivorum* or *Sphingobacterium spiritivorum*. Moreover, although results of analyzing analyses on the homology of the base sequence of the 16S rRNA gene indicate the highest degree of homology was exhibited with *Sphingobacterium multivorum* (98.8%), there were was no strain with which the bacterial strain matched completely. Accordingly, this bacterial strain was therefore identified as *Sphingobacterium* sp.

As these microbes, either wild strains or mutant strains can be used or recombinant strains induced by cell fusion or genetic techniques such as genetic manipulation can be used.

To obtain microbial cells of such microbes, the microbes can be cultured and grown in a suitable medium. There is no particular restriction on the medium used for this purpose so far as it allows the microbes to grow. This medium may be an ordinary medium containing ordinary carbon sources, nitrogen sources, phosphorus sources, sulfur sources, inorganic ions, and organic nutrient sources as necessary.

For example, any carbon source may be used so far as the microbes can utilize it. Specific examples of the carbon source that can be used include sugars such as glucose, fructose, maltose and amylose, alcohols such as sorbitol, ethanol and glycerol, organic acids such as fumaric acid, citric acid, acetic acid and propionic acid and their salts, hydrocarbons such as paraffin as well as mixtures thereof.

Examples of nitrogen sources that can be used include ammonium salts of inorganic acids such as ammonium sulfate and ammonium chloride, ammonium salts of organic acids such as ammonium fumarate ammonium citrate, nitrates such as sodium nitrate and potassium nitrate, organic nitrogen compounds such as peptones, yeast extract, meat extract and corn steep liquor as well as mixtures thereof.

In addition, nutrient sources used in ordinary media, such as inorganic salts, trace metal salts and vitamins, can also be suitably mixed and used.

There is no particular restriction on culturing conditions, and culturing can be carried out, for example, for about 12 to about 48 hours while properly controlling the pH and temperature within a pH range of 5 to 8 and a temperature range of 15 to 40° C., respectively, under aerobic conditions.

3. Enzymes Used in the Present Invention

In the method for producing peptide according to the present invention described above, an enzyme which has an ability to selectively link L-phenylalanine to the α-ester site of an L-aspartic acid-α,β-diester through a peptide bond is used. In the method for producing peptide according to the present invention, the enzyme is not limited by its origination and procuring method so far as it has such an activity. Hereinafter, purification of enzymes used in the present invention and utilization of techniques of genetic engineering will be explained.

(3-1) Microbes Having an Enzyme which can be Used for the Production Method of the Present Invention As microbes which produce an enzyme of the present invention, all the microbes that have an ability to produce an α-L-aspartyl-L-phenylalanine-β-ester from an L-aspartic acid-α,β-diester and L-phenylalanine can be used. The microbes include bacteria and the like that belong to genera selected from the group consisting of *Aeromonas, Azotobacter, Alcaligenes, Brevibacterium, Corynebacterium, Escherichia, Empedobacter, Flavobacterium, Microbacterium, Propionibacterium, Brevibacillus, Paenibacillus, Pseudomonas, Serratia, Stenotrophomonas, Sphingobacterium, Streptomyces, Xanthomonas, Williopsis, Candida, Geotrichum, Pichia, Saccharomyces, Torulaspora, Cellulophaga, Weeksella, Pedobacter, Persicobacter, Flexithrix, Chitinophaga, Cyclobacterium, Runella, Thermonema, Psychroserpens, Gelidibacter, Dyadobacter, Flammeovirga, Spirosoma, Flectobacillus, Tenacibaculum, Rhodotermus, Zobellia, Muricauda, Salegentibacter, Taxeobacter, Cytophaga, Marinilabilia, Lewinella, Saprospira,* and *Haliscomenobacter.* More specifically, the microbes include *Empedobacter brevis* ATCC 14234 (FERM P-18545 strain, FERM BP-8113 strain (Depositary institution: the independent administrative corporation, National Institute of Advanced Industrial Science and Technology, International Patent Organism Depositary, Address of depositary institution: Chuo Dai-6, 1-1 Higashi 1-Chome, Tsukuba-shi, Ibaraki-ken, Japan, International deposit transfer date: Jul. 8, 2002)), *Sphingobacterium* sp. FERM BP-8124 strain (Depositary institution: the independent administrative corporation, National Institute of Advanced Industrial Science and Technology, International Patent Organism Depositary, Address of depositary institution: Chuo Dai-6, 1-1 Higashi 1-Chome, Tsukuba-shi, Ibaraki-ken, Japan, International deposit date: Jul. 22, 2002), *Pedobacter heparinus* IFO 12017 (Depositary institution: the Institute of Fermentation, Osaka; 2-17-85 Jusanbon-cho, Yodogawa-ku, Osaka-shi, Japan), *Taxeobacter gelupurpurascens* DSMZ 11116 (Depositary institution; the Deutche Sammlung von Mikroorganismen and Zellkulturen GmbH (German Collection of Microbes and Cell Cultures, Address of Depositary institution; Mascheroder Weg 1b, 38124 Braunschweig, Germany), *Cyclobacterium marinum* ATCC 25205 (Depositary institution; the American Type Culture Collection, address of depositary institution; P.O. Box 1549, Manassas, Va. 20110, the United States of America), and *Psychroserpens burtonensis* ATCC 700359 (Depositary institution; the American Type Culture Collection, address of depositary institution; P.O. Box 1549, Manassas, Va. 20110, the United States of America) and so forth. *Empedobacter brevis* ATCC 14234 strain (FERM P-18545 strain, FERM BP-8113 strain (Depositary institution: the independent administrative corporation, National Institute of Advanced Industrial Science and Technology, International Patent Organism Depositary, Address of depositary institution: Chuo Dai-6, 1-1 Higashi 1-Chome, Tsukuba-shi, Ibaraki-ken, Japan, International deposit transfer date: Jul. 8, 2002)) and *Sphingobacterium* sp. FERM BP-8124 strain (Depositary institution: the independent administrative corporation, National Institute of Advanced Industrial Science and Technology, International Patent Organism Depositary, Address of depositary institution: Chuo Dai-6, 1-1 Higashi 1-Chome, Tsukuba-shi, Ibaraki-ken, Japan, International deposit date: Jul. 22, 2002), *Pedobacter heparinus* IFO 12017 strain (Depositary institution: the Institute of Fermentation, Osaka; 2-17-85 Jusanbon-cho, Yodogawa-ku, Osaka-shi, Japan), *Taxeobacter gelupurpurascens* DSMZ 11116 strain (Depositary institution; the Deutche Sammlung von Mikroorganismen and Zellkulturen GmbH (German Collection of Microbes and Cell Cultures, Address of Depositary institution; Mascheroder Weg 1b, 38124 Braunschweig, Germany), *Cyclobacterium marinum* ATCC 25205 strain (Depositary institution; the American Type Culture Collection, address of depositary institution; P.O. Box 1549, Manassas, Va. 20110, the United States of America), and *Psycloserpens burtonensis* ATCC 700359 strain (Depositary institution; the American Type Culture Collection, address of depositary institution; P.O. Box 1549, Manassas, Va. 20110, the United States of America) and the like are microbes selected by the present inventors as a result of search of enzyme producing microbes which produce an α-L-aspartyl-L-phenylalanine-β-ester from an L-aspartic acid-α,β-diester and L-phenylalanine at high yield.

(3-2) Purification of Enzyme

As was previously mentioned, the peptide-forming enzyme used in the present invention can be purified from bacteria belonging to, for example, the genus *Empedobacter*. A method for isolating and purifying a peptide-forming enzyme from *Empedobacter brevis* is explained as an example of purification of the enzyme.

First, a microbial cell extract is prepared from microbial cells of *Empedobacter brevis*, for example, the strain FERM BP-8113 (Depositary institution: the independent administrative corporation, National Institute of Advanced Industrial Science and Technology, International Patent Organism Depositary, Address of depositary institution: Chuo Dai-6, 1-1 Higashi 1-Chome, Tsukuba-shi, Ibaraki-ken, Japan, International deposit transfer date: Jul. 8, 2002) by disrupting the cells using a physical method such as ultrasonic crushing or an enzymatic method using a cell wall-dissolving enzyme and removing the insoluble fraction by centrifugal separation and so forth. The peptide-producing enzyme can then be purified by fractionating the cell extract obtained in the above manner by combining ordinary protein purification methods such as anion exchange chromatography, cation exchange chromatography or gel filtration chromatography.

An example of a carrier for use in anion exchange chromatography is Q-Sepharose HP (manufactured by Amersham). The enzyme is recovered in the non-adsorbed fraction under conditions of pH 8.5 when the cell extract containing the enzyme is allowed to pass through a column packed with the carrier.

An example of a carrier for use in cation exchange chromatography is MonoS HR (manufactured by Amersham). After adsorbing the enzyme onto the column by allowing the cell extract containing the enzyme to pass through a column packed with the carrier and then washing the column, the enzyme is eluted with a buffer solution having a high salt concentration. At that time, the salt concentration may be sequentially increased or a concentration gradient may be applied. For example, in the case of using MonoS HR, the enzyme adsorbed onto the column is eluted at an NaCl concentration of about 0.2 to about 0.5 M.

The enzyme purified in the manner described above can then be further uniformly purified by gel filtration chromatography and so forth. An example of the carrier for use in gel filtration chromatography is Sephadex 200pg (manufactured by Amersham).

In the aforementioned purification procedure, the fraction containing the enzyme can be verified by assaying the peptide-forming activity of each fraction according to the method indicated in the examples to be described later. The internal amino acid sequence of the enzyme purified in the manner described above is shown in SEQ ID NO: 1 and SEQ ID NO: 2 of the Sequence Listing.

(3-3) Isolation DNA, Production of Transformant and Purification of Peptide-Forming Enzyme (3-3-1) Isolation of DNA The inventors of the present invention first succeeded in isolating one type of DNA of a peptide-forming enzyme that can be used in the peptide production method of the present invention from *Empedobacter brevis* strain FERM BP-8113 (Depositary institution: the independent administrative corporation, National Institute of Advanced Industrial Science and Technology, International Patent Organism Depositary, Address of depositary institution: Chuo Dai-6, 1-1 Higashi 1-Chome, Tsukuba-shi, Ibaraki-ken, Japan, International deposit transfer date: Jul. 8, 2002).

A DNA having a base sequence consisting of bases numbers 61 to 1908 of the base sequence described in SEQ ID NO: 5, which is a DNA of the present invention, was isolated from *Empedobacter brevis* strain FERM BP-8113 (Depositary institution: the independent administrative corporation, National Institute of Advanced Industrial Science and Technology, International Patent Organism Depositary, Address of depositary institution: Chuo Dai-6, 1-1 Higashi 1-Chome, Tsukuba-shi, Ibaraki-ken, Japan, International deposit transfer date: Jul. 8, 2002). The DNA having the base sequence consisting of bases numbers 61 to 1908 is a code sequence (CDS) portion. In the base sequence consisting of bases numbers 61 to 1908 is contained a signal sequence region and a mature protein region. The signal sequence region is a region that consists of bases numbers 61 to 126, while the mature protein region is a region that consists of bases numbers 127 to 1908. Namely, the present invention provides both a gene for a peptide-forming enzyme protein that contains a signal sequence, and a gene for a peptide-forming enzyme protein in the form of a mature protein. The signal sequence contained in the sequence described in SEQ ID NO: 5 is a kind of leader sequence. The main function of a leader peptide encoded by the leader sequence is presumed to be excretion from inside the cell membrane to outside the cell membrane. The protein encoded by bases numbers 127 to 1908, namely the -ester site excluding the leader peptide, is presumed to be a mature protein and exhibit a high degree of peptide-forming activity.

The DNA consisting of the base sequence that consists of bases numbers 61 to 1917 described in SEQ ID NO: 11, which is also a DNA of the present invention, was isolated from *Sphingobacterium* sp. strain FERM BP-8124 (Depositary institution: the independent administrative corporation, National Institute of Advanced Industrial Science and Technology, International Patent Organism Depositary, Address of depositary institution: Chuo Dai-6, 1-1 Higashi 1-Chome, Tsukuba-shi, Ibaraki-ken, Japan, International deposit date: Jul. 22, 2002). The DNA consisting of the base sequence that consists of bases numbers 61 to 1917 is a code sequence (CDS) portion. In the base sequence consisting of bases numbers 61 to 1917, a signal sequence region and a mature protein region are contained. The signal sequence region is a region that consists of bases numbers 61 to 120, while the mature protein region is a region that consists of bases numbers 121 to 1917. Namely, the present invention provides both a gene for a peptide-forming enzyme protein that contains a signal sequence, and a gene for a peptide-forming enzyme protein in the form of a mature protein. The signal sequence contained in the sequence described in SEQ ID NO: 11 is a kind of leader sequence. The main function of a leader peptide encoded by the leader sequence is presumed to be excretion from inside the cell membrane to outside the cell membrane. The protein encoded by bases numbers 121 to 1917, namely the portion excluding the leader peptide, is presumed to be a mature protein and exhibit a high degree of peptide-forming activity.

The DNA consisting of the base sequence that consists of bases numbers 61 to 1935 described in SEQ ID NO: 17, which is also a DNA of the present invention, was isolated from *Pedobacter heparinus* strain IFO 12017 (Depositary institution: the Institute of Fermentation, Osaka; 2-17-85 Jusanbon-cho, Yodogawa-ku, Osaka-shi, Japan). The DNA consisting of the base sequence that consists of bases numbers 61 to 1935 described in SEQ ID NO:17 is a code sequence (CDS) portion. In the base sequence consisting of bases numbers 61 to 1935, a signal sequence region and a mature protein region are contained. The signal sequence region is a region that consists of bases numbers 61 to 126, while the mature protein region is a region that consists of bases numbers 127 to 1935. Namely, the present invention provides both a gene for a peptide-forming enzyme protein that contains a signal sequence, and a gene for a peptide-forming enzyme protein in the form of a mature protein. The signal sequence contained in the sequence described in SEQ ID NO: 17 is a kind of leader sequence. The main function of a leader peptide encoded by the leader sequence is presumed to be excretion from inside the cell membrane to outside the cell membrane. The protein encoded by bases numbers 127 to 1935, namely the portion excluding the leader peptide, is presumed to be a mature protein and exhibit a high degree of peptide-forming activity.

The DNA consisting of the base sequence that consists of bases numbers 61 to 1995 described in SEQ ID NO: 22, which is also a DNA of the present invention, was isolated from *Taxeobacter gelupurpurascens* DSMZ 11116 (Depositary institution; the Deutche Sammlung von Mikroorganismen and Zellkulturen GmbH (German Collection of Microbes and Cell Cultures, Address of Depositary institution; Mascheroder Weg 1b, 38124 Braunschweig, Germany). The DNA consisting of the base sequence that consists of bases numbers 61 to 1995 described in SEQ ID NO:22 is a code sequence (CDS) portion. In the base sequence consisting of bases numbers 61 to 1995, a signal sequence region and a mature protein region are contained. The signal sequence region is a region that consists of bases numbers 61 to 126, while the mature protein region is a region that consists of bases numbers 127 to 1995. Namely, the present invention provides both a gene for a peptide-forming enzyme protein that contains a signal sequence, and a gene for a peptide-forming enzyme protein in the form of a mature protein. The signal sequence contained in the sequence described in SEQ ID NO: 22 is a kind of leader sequence. The main function of a leader peptide encoded by the leader sequence is presumed to be excretion from inside the cell membrane to outside the cell membrane. The protein encoded by bases numbers 127 to 1995, namely the portion excluding the leader peptide, is presumed to be a mature protein and exhibit a high degree of peptide-forming activity.

The DNA consisting of the base sequence that consists of bases numbers 29 to 1888 described in SEQ ID NO: 24, which is also a DNA of the present invention, was isolated from *Cyclobacterium marinum* ATCC 25205 (Depositary institution; the American Type Culture Collection, address of depositary institution; P.O. Box 1549, Manassas, Va. 20110, the United States of America). The DNA consisting of the base sequence that consists of bases numbers 29 to 1888 described in SEQ ID NO:24 is a code sequence (CDS) portion. In the base sequence consisting of bases numbers 29 to 1888, a signal sequence region and a mature protein region are contained. The signal sequence region is a region that consists of bases numbers 29 to 103, while the mature protein region is a region that consists of bases numbers 104 to 1888. Namely, the present invention provides both a gene for a peptide-forming enzyme protein that contains a signal sequence, and a gene for a peptide-forming enzyme protein in the form of a mature protein. The signal sequence contained in the sequence described in SEQ ID NO: 24 is a kind of leader sequence. The main function of a leader peptide encoded by the leader sequence is presumed to be excretion from inside the cell membrane to outside the cell membrane. The protein encoded by bases numbers 104 to 1888, namely the portion excluding the leader peptide, is presumed to be a mature protein and exhibit a high degree of peptide-forming activity.

The DNA consisting of the base sequence that consists of bases numbers 61 to 1992 described in SEQ ID NO: 26, which is also a DNA of the present invention, was isolated from *Psychroserpens burtonensis* ATCC 700359 (Depositary institution; the American Type Culture Collection, address of depositary institution; P.O. Box 1549, Manassas, Va. 20110, the United States of America). The DNA consisting of the base sequence that consists of bases numbers 61 to 1992 described in SEQ ID NO:26 is a code sequence (CDS) portion. In the base sequence consisting of bases numbers 61 to 1992, a signal sequence region and a mature protein region are contained. The signal sequence region is a region that consists of bases numbers 61 to 111, while the mature protein region is a region that consists of bases numbers 112 to 1992. Namely, the present invention provides both a gene for a peptide-forming enzyme protein that contains a signal sequence, and a gene for a peptide-forming enzyme protein in the form of a mature protein. The signal sequence contained in the sequence described in SEQ ID NO: 26 is a kind of leader sequence. The main function of a leader peptide encoded by the leader sequence is presumed to be excretion from inside the cell membrane to outside the cell membrane. The protein encoded by bases numbers 112 to 1992, namely the portion excluding the leader peptide, is presumed to be a mature protein and exhibit a high degree of peptide-forming activity.

Furthermore, the various gene recombination techniques indicated below can be carried out in accordance with the descriptions in Molecular Cloning, 2nd edition, Cold Spring Harbor Press (1989) and other publications.

A DNA encoding an enzyme that can be used in the present invention can be acquired by polymerase chain reaction (PCR, refer to White, T. J. et al., Trends Genet., 5, 185 (1989)) or hybridization from a chromosomal DNA or a DNA library of *Empedobacter brevis, Sphingobacterium* sp., *Pedobacter heparinus, Taxeobacter gelupurpurascens, Cyclobacterium marinum,* or *Psychroserpens burtonensis*. Primers used in PCR can be designed based on the internal amino acid base sequences determined on the basis of purified peptide-forming enzyme as explained in the previous section (3). In addition, since the base sequences of the peptide-forming enzyme genes (SEQ ID NO: 5, SEQ ID NO: 11, SEQ ID NO:17, SEQ ID NO:22, SEQ ID NO:24, and SEQ ID NO:26) have been identified by the present invention, primers or hybridization probes can be designed on the basis of these base sequences, and the gene can be isolated using the probes. If primers having sequences corresponding to the 5'-nontranslated region and 3'-nontranslated region, respectively, are used as PCR primers, the full-length encoded region of the enzyme can be amplified. Taking as an example the case of amplifying a region containing both the leader sequence and a mature protein encoding region as described in SEQ ID NO: 5, specific examples of primers include a primer having a base sequence of the region upstream of base number 61 in SEQ ID NO: 5 for the 5'-side primer, and a primer having a sequence complementary to the base sequence of the region downstream of base number 1908 for the 3'-side primer.

Primers can be synthesized, for example, according to ordinary methods using the phosphoramidite method (refer to Tetrahedron Letters (1981), 22, 1859) by use of the Model 380B DNA Synthesizer manufactured by Applied Biosystems. The PCR reaction can be carried out, for example, by using the Gene Amp PCR System 9600 (Perkin-Elmer) and the Takara LA PCR In Vitro Cloning Kit (Takara Shuzo) in accordance with the method specified by the supplier such as the manufacturer.

A DNA that encodes an enzyme that can be used in the peptide production method of the present invention, regardless of whether the DNA contains a leader sequence or not, includes a DNA that is substantially identical to the DNA consisting of the CDS described in SEQ ID NO: 5 of the Sequence Listing. Namely, a DNA substantially identical to the DNA of the present invention can be obtained by isolating a DNA that hybridizes a DNA consisting of a base sequence complementary to the CDS described in SEQ ID NO: 5 of the Sequence Listing or with a probe prepared from the base sequence under stringent conditions and encodes a protein having peptide-forming activity from a DNA encoding the mutant enzyme or cells that possess that DNA.

The DNA of the present invention, regardless of whether it contains a leader sequence or not, includes a DNA that is substantially identical to the DNA consisting of the CDS described in SEQ ID NO: 11 of the Sequence Listing. Namely, a DNA substantially identical to the DNA of the present invention can be obtained by isolating a DNA that hybridizes a DNA consisting of a base sequence complementary to the CDS described in SEQ ID NO: 11 of the Sequence Listing or with a probe prepared from the base sequence under stringent conditions and encodes a protein having peptide-forming activity from a DNA encoding the mutant enzyme or cells that possess that DNA.

The DNA of the present invention, regardless of whether it contains a leader sequence or not, includes a DNA that is substantially identical to the DNA consisting of the CDS described in SEQ ID NO: 17 of the Sequence Listing. Namely, a DNA substantially identical to the DNA of the present invention can be obtained by isolating a DNA that hybridizes with a DNA consisting of a base sequence complementary to the CDS described in SEQ ID NO: 17 of the Sequence Listing or with a probe prepared from the base sequence under stringent conditions and encodes a protein having peptide-forming activity from a DNA encoding the mutant enzyme or cells that possess that DNA.

The DNA of the present invention, regardless of whether it contains a leader sequence or not, includes a DNA that is substantially identical to the DNA consisting of the CDS described in SEQ ID NO: 22 of the Sequence Listing. Namely, a DNA substantially identical to the DNA of the present invention can be obtained by isolating a DNA that hybridizes with a DNA consisting of a base sequence complementary to the CDS described in SEQ ID NO: 22 of the Sequence Listing or with a probe prepared from the base sequence under stringent conditions and encodes a protein having peptide-forming activity from a DNA encoding the mutant enzyme or cells that possess that DNA.

The DNA of the present invention, regardless of whether it contains a leader sequence or not, includes a DNA that is substantially identical to the DNA consisting of the CDS described in SEQ ID NO: 24 of the Sequence Listing. Namely, a DNA substantially identical to the DNA of the present invention can be obtained by isolating a DNA that hybridizes with a DNA consisting of a base sequence complementary to the CDS described in SEQ ID NO: 24 of the Sequence Listing or with a probe prepared from the base sequence under stringent conditions and encodes a protein having peptide-forming activity from a DNA encoding the mutant enzyme or cells that possess that DNA.

The DNA of the present invention, regardless of whether it contains a leader sequence or not, includes a DNA that is substantially identical to the DNA consisting of the CDS described in SEQ ID NO: 26 of the Sequence Listing. Namely, a DNA substantially identical to the DNA of the present invention can be obtained by isolating a DNA that hybridizes with a DNA consisting of a base sequence complementary to the CDS described in SEQ ID NO: 26 of the Sequence Listing or with a probe prepared from the base sequence under stringent conditions and encodes a protein having peptide-forming activity from a DNA encoding the mutant enzyme or cells that possess that DNA.

A probe can be produced, for example, in accordance with established methods based on, for example, the base sequence described in SEQ ID NO: 5 of the Sequence Listing. In addition, a method for isolating a target DNA by using a probe to find a DNA that hybridizes with the probe may also be carried out in accordance with established methods. For example, a DNA probe can be produced by amplifying a base sequence cloned in a plasmid or phage vector, cleaving the base sequence desired to be used as a probe with a restriction enzyme and then extracting the desired base sequence. The portion to be cleaved out can be adjusted depending on the target DNA.

The term "under a stringent condition" as used herein refers to a condition under which a so-called specific hybrid is formed but no non-specific hybrid is formed. It is difficult to precisely express this condition in numerical values. For example, mention may be made of a condition under which DNAs having high homologies, for example, 50% or more, preferably 80% or more, more preferably 90% or more, hybridize with each other and DNAs having lower homologies than these do not hybridize with each other, or ordinary conditions for rinse in Southern hybridization under which hybridization is performed at 60° C. in a salt concentration corresponding 1×SSC and 0.1% SDS, preferably 0.1×SSC and 0.1% SDS. Although the genes that hybridize under such conditions include those genes in which stop codons have occurred at certain locations along their sequences or which have lost activity due to a mutation in the active center, these can be easily removed by ligating them to a commercially available expression vector, expressing them in a suitable host, and assaying the enzyme activity of the expression product using a method to be described later.

However, in the case of a base sequence that hybridizes under stringent conditions as described above, it is preferable that the protein encoded by that base sequence retains about a half or more, preferably 80% or more, and more preferably 90% or more, of the enzyme activity of the protein having the amino acid sequence encoded by the original base sequence serving as the base be retained under conditions of 50° C. and pH 8. For example, when explained for on the case of, for example, a base sequence that hybridizes under stringent conditions with a DNA that has a base sequence complementary to the base sequence consisting of bases numbers 127 to 1908 of the base sequence described in SEQ ID NO: 5, it is preferable that the protein encoded by that base sequence retains about a half or more, preferably 80% or more, and more preferably 90% or more, of the enzyme activity of the protein having an amino acid sequence that consists of amino acid residues numbers 23 to 616 of the amino acid sequence described in SEQ ID NO: 6 under conditions of 50° C. and pH 8.

An amino acid sequence encoded by the CDS described in SEQ ID NO: 5 of the Sequence Listing is shown in SEQ ID NO: 6 of the Sequence Listing. An amino acid sequence encoded by the CDS described in SEQ ID NO: 11 of the Sequence Listing is shown in SEQ ID NO: 12 of the Sequence Listing. An amino acid sequence encoded by the CDS described in SEQ ID NO.: 17 of the Sequence Listing is shown in SEQ ID NO: 18 of the Sequence Listing. An amino acid sequence encoded by the CDS described in SEQ ID NO: 22 of the Sequence Listing is shown in SEQ ID NO: 23 of the Sequence Listing. An amino acid sequence encoded by the CDS described in SEQ ID NO: 24 of the Sequence Listing is shown in SEQ ID NO: 25 of the Sequence Listing. An amino acid sequence encoded by the CDS described in SEQ ID NO: 26 of the Sequence Listing is shown in SEQ ID NO: 27 of the Sequence Listing.

The entire amino acid sequence described in SEQ ID NO: 6 contains a leader peptide and a mature protein region, with amino acid residues numbers 1 to 22 constituting the leader peptide, and amino acid residues numbers 23 to 616 constituting the mature protein region.

The entire amino acid sequence described in SEQ ID NO: 11 includes a leader peptide and a mature protein region, with amino acid residues numbers 1 to 20 constituting the leader peptide, and amino acid residues numbers 21 to 619 constituting the mature protein region.

The entire amino acid sequence described in SEQ ID NO: 18 contains a leader peptide and a mature protein region, with amino acid residues numbers 1 to 22 constituting the leader peptide, and amino acid residues numbers 23 to 625 constituting the mature protein region.

The entire amino acid sequence described in SEQ ID NO: 23 contains a leader peptide and a mature protein region, with amino acid residues numbers 1 to 22 constituting the leader peptide, and amino acid residues numbers 23 to 645 constituting the mature protein region.

The entire amino acid sequence described in SEQ ID NO: 25 contains a leader peptide and a mature protein region, with amino acid residues numbers 1 to 25 constituting the leader peptide, and amino acid residues numbers 26 to 620 constituting the mature protein region.

The entire amino acid sequence described in SEQ ID NO: 27 contains a leader peptide and a mature protein region, with amino acid residues numbers 1 to 17 constituting the leader peptide, and amino acid residues numbers 18 to 644 constituting the mature protein region.

The protein encoded by the DNA of the present invention is a protein in which the mature protein has peptide-forming activity, and a DNA that encodes a protein substantially identical to a protein having the amino acid sequence described in SEQ ID NO: 6, SEQ ID NO: 12, SEQ ID NO: 18, SEQ ID NO: 23, SEQ ID NO: 25, or SEQ ID NO: 27 of the Sequence Listing, regardless of whether it contains a leader peptide or not, is also included in the DNA of the present invention. (Note that, base sequences are specified from amino acid sequences in accordance with the codes of the universal codons.) Namely, the present invention provides DNAs that encode proteins indicated in (A) to (X) below:

(A) a protein having an amino acid sequence consisting of amino acid residues numbers 23 to 616 of an amino acid sequence described in SEQ ID NO: 6 of the Sequence Listing, (B) a protein having an amino acid sequence including substitution, deletion, insertion, addition, and/or inversion of one or a plurality of amino acids in the amino acid sequence consisting of amino acid residues numbers 23 to 616 of the amino acid sequence described in SEQ ID NO: 6 of the Sequence Listing, and having activity to selectively linking L-phenylalanine to an α-ester site of the L-aspartic acid-α,β-diester through a peptide bond, (C) a protein having the amino acid sequence consisting of amino acid residue numbers 21 to 619 of an amino acid sequence described in SEQ ID NO: 12 of the Sequence Listing, (D) a protein having an amino acid sequence including substitution, deletion, insertion, addition, and/or inversion of one or a plurality of amino acids in the amino acid sequence consisting of amino acid residue numbers 21 to 619 of the amino acid sequence described in SEQ ID NO: 12 of the Sequence Listing, and having activity to selectively linking L-phenylalanine to an α-ester site of the L-aspartic acid-α,β-diester through a peptide bond, (E) a protein having the amino acid sequence consisting of amino acid residues numbers 23 to 625 of an amino acid sequence described in SEQ ID NO: 18 of the Sequence Listing, (F) a protein having an amino acid sequence including substitution, deletion, insertion, addition, and/or inversion of one or a plurality of amino acids in the amino acid sequence consisting of amino acid residues numbers 23 to 625 of the amino acid sequence described in SEQ ID NO: 18 of the Sequence Listing, and having activity to selectively linking L-phenylalanine to an α-ester site of the L-aspartic acid-α,β-diester through a peptide bond, (G) a protein having an amino acid sequence consisting of amino acid residues numbers 23 to 645 of an amino acid sequence described in SEQ ID NO: 23 of the Sequence Listing, (H) a protein having an amino acid sequence including substitution, deletion, insertion, addition, and/or inversion of one or a plurality of amino acids in the amino acid sequence consisting of amino acid residues numbers 23 to 645 of the amino acid sequence described in SEQ ID NO: 23 of the Sequence Listing, and activity to selectively linking L-phenylalanine to an α-ester site of the L-aspartic acid-α,β-diester through a peptide bond, (I) a protein having an amino acid sequence consisting of amino acid residues numbers 26 to 620 of an amino acid sequence described in SEQ ID NO: 25 of the Sequence Listing, (J) a protein having an amino acid sequence including substitution, deletion, insertion, addition, and/or inversion of one or a plurality of amino acids in the amino acid sequence consisting of amino acid residues numbers 26 to 620 of the amino acid sequence described in SEQ ID NO: 25 of the Sequence Listing, and having activity to selectively linking L-phenylalanine to an α-ester site of the L-aspartic acid-α,β-diester through a peptide bond, (K) a protein having an amino acid sequence consisting of amino acid residues numbers 18 to 644 of an amino acid sequence described in SEQ ID NO: 27 of the Sequence Listing, (L) a protein having an amino acid sequence including substitution, deletion, insertion, addition, and/or inversion of one or a plurality of amino acids in the amino acid sequence consisting of amino acid residues numbers 18 to 644 of the amino acid sequence described in SEQ ID NO: 27 of the Sequence Listing, and having activity to selectively linking L-phenylalanine to an α-ester site of the L-aspartic acid-α,β-diester through a peptide bond, (M) a protein having an amino acid sequence described in SEQ ID NO: 6 of the Sequence Listing, (N) a protein containing a mature protein region, having an amino acid sequence including substitution, deletion, insertion, addition, and/or inversion of one or a plurality of amino acids in the amino acid sequence described in SEQ ID NO: 6 of the Sequence Listing, and activity to selectively linking L-phenylalanine to an α-ester site of the L-aspartic acid-α,β-diester through a peptide bond, (O) a protein having the amino acid sequence described in SEQ ID NO: 12 of the Sequence Listing, (P) a protein containing a mature protein region, having an amino acid sequence including substitution, deletion, insertion, addition, and/or inversion of one or a plurality of amino acids in the amino acid sequence described in SEQ ID NO: 12 of the Sequence Listing, and activity to selectively linking L-phenylalanine to an α-ester site of the L-aspartic acid-α,β-diester through a peptide bond, (Q) a protein having an amino acid sequence described in SEQ ID NO: 18 of the Sequence Listing, (R) a protein containing a mature protein region, having an amino acid sequence including substitution, deletion, insertion, addition, and/or inversion of one or a plurality of amino acids in the amino acid sequence described in SEQ ID NO: 18 of the Sequence Listing, and activity to selectively linking L-phenylalanine to an α-ester site of the L-aspartic acid-α,β-diester through a peptide bond, (S) a protein having an amino acid sequence described in SEQ ID NO: 23 of the Sequence Listing, (T) a protein containing a mature protein region, having an amino acid sequence including substitution, deletion, insertion, addition, and/or inversion of one or a plurality of amino acids in the amino acid sequence described in SEQ ID NO: 23 of the Sequence Listing, and activity to selectively linking L-phenylalanine to an α-ester site of the L-aspartic acid-α,β-diester through a peptide bond, (U) a protein having an amino acid sequence described in SEQ ID NO: 25 of the Sequence Listing, (V) a protein containing a mature protein region, having an amino acid sequence including substitution, deletion, insertion, addition, and/or inversion of one or a plurality of amino acids in the amino acid sequence described in SEQ ID NO: 25 of the Sequence Listing, and activity to selectively linking L-phenylalanine to an α-ester site of the L-aspartic acid-α,β-diester through a peptide bond, (W) a protein having an amino acid sequence described in SEQ ID NO: 27 of the Sequence Listing, and (X) a protein containing a mature protein region, having an amino acid sequence in the amino acid sequence described in SEQ ID NO: 27 of the Sequence Listing, and having activity to selectively linking L-phenylalanine to an α-ester site of the L-aspartic acid-α,β-diester through a peptide bond.

Here, although the meaning of the term "a plurality of" varies depending on the locations and types of the amino acid residues in the three-dimensional structure of the protein, it is within a range that does not significantly impair the three-dimensional structure and activity of the protein of the amino acid residues, and is specifically 2 to 50, preferably 2 to 30, and more preferably 2 to 10. However, in the case of amino acid sequences including substitution, deletion, insertion, addition, and/or inversion of one or a plurality of amino acids in amino acid sequences of the proteins of (B), (D), (F), (H), (J), (L), (N), (P), (R), (T), (V) or (X), it is preferable that the proteins retain about half or more, more preferably 80% or more, and even more preferably 90% or more of the enzyme activity of the proteins in the state where no mutation is included, under conditions of 50° C. and pH 8. For example, explanation will be made in the case of (B); in the case of the amino acid sequence (B) including substitution, deletion, insertion, addition, and/or inversion of one or a plurality of amino acids in an amino acid sequence described in SEQ ID NO: 6 of the Sequence Listing, it is preferable that this protein retains about half or more, more preferably 80% or more, and even more preferably 90% or more of the enzyme activity of the protein having the amino acid sequence described in SEQ ID NO: 6 of the Sequence Listing, under conditions of 50° C. and pH 8.

A mutation of an amino acid like that indicated in the aforementioned (B) and so forth is obtained by modifying the base sequence so that an amino acid of a specific-ester site in the present enzyme gene is substituted, deleted, inserted or added by, for example, -ester site-directed mutagenesis. In addition, a modified DNA like that described above can also be acquired by mutagenesis treatment known in the art. Mutagenesis treatment refers to, for example, a method in which a DNA encoding the present enzyme is treated in vitro with hydroxylamine and so forth, as well as a method in which Escherichia bacteria that possess a DNA encoding the present enzyme are treated by a mutagen normally used in artificial mutagenesis, such as ultraviolet irradiation, N-methyl-N'-nitro-N-nitrosoguanidine (NTG) or nitrous acid.

In addition, naturally-occurring mutations such as differences attributable to a microbe species or strain are also included in the base substitution, deletion, insertion, addition and/or inversion described above. By expressing a DNA having such a mutation in suitable cells and investigating the enzyme activity of the expression product, a DNA can be obtained that encodes a protein substantially identical to the protein described in SEQ ID NO: 6, 12, 18, 23, 25 or 27 of the Sequence Listing.

(3-3-2) Preparation of Transformants and Production of Peptide-Forming Enzymes

Peptide-forming enzymes that can be used in the method of producing a peptide according to the present invention can be produced by introducing the DNA explained in (3-3-1) above into a suitable host and expressing the DNA in that host.

With respect to hosts for expressing a protein specified by the DNA, examples of the hosts that can be used include various prokaryotic cells including *Escherichia* bacteria such as *Escherichia coli*, *Empedobacter* bacteria, *Sphingobacterium* bacteria, *Flavobacterium* bacteria and *Bacillus subtilis*, as well as various eukaryotic cells including *Saccharomyces cerevisiae*, *Pichia stipitis* and *Aspergillus oryzae*.

A recombinant DNA used to introduce a DNA into a host can be prepared by inserting the DNA to be introduced into a vector corresponding to the type of host in which the DNA is to be expressed, in such a form that the protein encoded by that DNA can be expressed. In the case where a promoter unique to a peptide-forming enzyme gene of *Empedobacter brevis* and so forth functions in the host cells, the promoter can be used as a promoter for expressing the DNA of the present invention. In addition, another promoter that acts in the host cells may be ligated to the DNA of the present invention, and the DNA may be expressed under the control of the promoter as necessary.

Examples of transformation methods for introducing a recombinant DNA into host cells include the method of D. M. Morrison (see Methods in Enzymology, 68, 326 (1979)) or the method in which DNA permeability is increased by treating receptor microbial cells with calcium chloride (see Mandel, H. and Higa, A., J. Mol. Biol., 53, 159 (1970)).

In the case of mass production of a protein using recombinant DNA technology, conjugating the protein within a transformant that produces the protein to form an inclusion body of protein is also a preferable mode for carrying out the present invention. Advantages of this expression and production method include protection of the target protein from digestion by proteases present within the microbial cells, and simple and easy purification of the target protein by disrupting the microbial cells followed by centrifugal separation and so forth.

The inclusion body of protein obtained in this manner is solubilized with a protein denaturant and the protein is converted to a properly folded, physiologically active protein through an activity regeneration procedure that consists primarily of removal of the denaturant. There are numerous examples of this, including regeneration of the activity of human interleukin-2 (see Japanese Patent Application Laid-open Publication No. S61-257931).

To obtain an active protein from inclusion bodies of, a series of procedures including solubilization and activity regeneration are required, and the procedure is more complex than in the case of producing the active protein directly. However, in the case of producing a protein that has a detrimental effect on microbial growth in large volumes within microbial cells, that effect can be suppressed by accumulating the proteins in the form of inclusion bodies of inactive protein within the microbial cells.

Examples of mass production methods for producing a target protein in the form of inclusion bodies include a method in which a target protein is expressed independently under the control of a powerful promoter, and a method in which a target protein is expressed in the form of a fused protein with a protein that is known to be expressed in a large volume.

Hereinafter, the present invention will be explained more specifically taking as an example a method for producing transformed *Escherichia coli* and using that transformed microbe to produce a peptide-forming enzyme. Furthermore, in the case of producing peptide-forming enzyme in a microbe such as *Escherichia coli*, a DNA that encodes a precursor protein containing a leader sequence may be incorporated or a DNA that consists only of a mature protein region that does not contain a leader sequence may be incorporated, and the DNA can be suitably selected for the protein encoding sequence depending on the production conditions, form, usage conditions and so forth of the enzyme to be produced.

Promoters normally used in the production of heterogeneous proteins in *Escherichia coli* can be used as a promoter for expressing a DNA encoding a peptide-forming enzyme. Examples of such promoters include T7 promoter, lac promoter, trp promoter, trc promoter, tac promoter, lambda phage PR promoter, PL promoter and other powerful promoters. In addition, examples of vectors that can be used include pUC19, pUC18, pBR322, pHSG299, pHSG298, pHSG399, pHSG398, RSF1010, pMW119, pMW118, pMW219, and pMW218. Besides, vectors of phage DNA can also be used. Moreover, expression vectors that contain promoters and are capable of expressing an inserted DNA sequence can be used.

To produce peptide-forming enzyme in the form of a fused protein inclusion body, a gene that encodes another protein, and preferably a hydrophilic peptide, is ligated upstream or downstream of the peptide-forming enzyme gene to obtain a fused protein gene. The gene that encodes another protein in this manner may be any gene that increases the amount of the fused protein accumulated and enhances the solubility of the fused protein after the denaturation and regeneration steps. Examples of candidates for such genes include T7 gene 10, β-galactosidase gene, dehydrofolate reductase gene, γ-interferon gene, interleukin-2 gene and prochymosin gene.

When these genes are ligated to the genes that encode peptide-forming enzymes, the genes are ligated so that reading frames of codons are consistent. It is recommended that the genes be ligated at a proper restriction enzyme-ester site or a synthetic DNA having a proper sequence be utilized.

Further, to increase a production amount of the peptide-forming enzyme, it is preferable in some cases that a terminator, which is a transcription terminating sequence, be ligated to downstream of the fusion protein gene. The terminator includes, for example, a T7 terminator, an fd phage terminator, a T4 terminator, a tetracycline resistant gene terminator, and an *Escherichia coli* trpA gene terminator.

As the vectors for introducing a gene that encodes a peptide-forming enzyme or a fused protein between the peptide-forming enzyme and another protein in *Escherichia coli* are preferred so-called multi-copy type vectors, examples of which include a plasmid having a replicator derived from ColE1, for example, a pUC-based plasmid, and a pBR322-based plasmid or derivatives thereof. The "derivatives" as used herein refer to those plasmids that are subjected modification by substitution, deletion, insertion, addition and/or inversion of bases. Note that the modification as used herein includes modifications by a mutation treatment with a mutagen or UV irradiation, or modifications by spontaneous mutation.

To screen transformants, it is preferable that the vectors have markers such as an ampicillin resistant gene. As such plasmids are commercially available expression vectors having potent promoters (a pUC-based vector (manufactured by Takara Shuzo, Co., Ltd.), pRROK-based vector (manufactured by Clonetech Laboratories, Inc.), pKK233-2 (manufactured by Clonetech Laboratories, Inc.) and so forth.

A recombinant DNA is obtained by ligating a DNA fragment to a vector DNA. In this case, a promoter, a gene encoding L-amino acid amide hydrolase or a fused protein consisting of an L-amino acid amide hydrolase and another protein, and depending on the case, a terminator are ligated in that order.

When *Escherichia coli* is transformed using the recombinant DNA and the resulting *Escherichia coli* is cultured, a peptide-forming enzyme or a fused protein consisting of the peptide-forming enzyme and another protein is expressed and produced. Although a strain that is normally used in the expression of a heterogeneous gene can be used as a host to be transformed, *Escherichia coli* strain JM109, for example, is preferable. Methods for carrying out transformation and methods for screening out transformants are described in Molecular Cloning, 2nd Edition, Cold Spring Harbor Press (1989) and other publications.

In the case of expressing a peptide-forming enzyme in the form of a fusion protein, the peptide-forming enzyme may be cleaved out using a restriction protease that uses a sequence not present in the peptide-forming enzyme, such as blood coagulation factor Xa or kallikrein, as the recognition sequence.

A medium normally used for culturing *Escherichia coli*, such as M9-casamino acid medium or LB medium, may be used as a production medium. In addition, culturing conditions and production induction conditions are suitably selected according to the marker of the vector used, promoter, type of host microbe and so forth.

The following method can be used to recover the peptide-forming enzyme or fused protein consisting of the peptide-forming enzyme and another protein. If the peptide-forming enzyme or its fused protein has been solubilized within the microbial cells, after recovering the microbial cells, the microbial cells are crushed or lysed so that they can be used as a crude enzyme liquid. Moreover, the peptide-forming enzyme or its fused protein can be purified prior to use by ordinary techniques such as precipitation, filtration or column chromatography as necessary. In this case, a purification method can also be used that uses an antibody of the peptide-forming enzyme or its fused protein.

In the case where protein inclusion bodies are formed, the inclusion bodies are solubilized with a denaturant. They may be solubilized together with the microbial cell protein. However, in consideration of the following purification procedure, the inclusion bodies are preferably taken out and then solubilized. Conventionally known methods may be used to recover the inclusion bodies from the microbial cells. For example, inclusion bodies can be recovered by crushing the microbial cells followed by centrifugal separation. Examples of denaturants capable of solubilizing inclusion bodies include guanidine hydrochloride (for example, 6 M, pH 5 to 8) and urea (for example, 8 M).

A protein having activity is regenerated by removing these denaturants by dialysis. A Tris-HCl buffer solution or a phosphate buffer solution and so forth may be used as the dialysis solution to be used in dialysis, and the concentration may be, for example, 20 mM to 0.5 M, while the pH may be, for example, 5 to 8.

The protein concentration during the regeneration step is preferably held to about 500 μg/ml or less. The dialysis temperature is preferably 5° C. or lower to inhibit the regenerated peptide-forming enzyme from undergoing self-crosslinking. Moreover, in addition to dialysis, dilution or ultrafiltration may be used to remove the denaturants, and it is expected that the activity can be regenerated regardless of whichever denaturant is used.

<2> Method of producing α-L-aspartyl-L-phenylalanine-α-methyl ester

The method of producing α-APM according to the present invention includes a first step of synthesizing α-L-aspartyl-L-phenylalanine-β-methyl ester according to the "<1> Method of producing α-L-aspartyl-L-phenylalanine-β-ester"

and a second step of converting α-L-aspartyl-L-phenylalanine-β-methyl ester to α-L-aspartyl-L-phenylalanine-α-methyl ester.

Preferred conditions in the first step and the like are as described in the "<1> Method of producing α-L-aspartyl-L-phenylalanine-β-ester". In addition, the second step can be carried out according to the known method and reference may be made to the method and preferred conditions described in, for example, Japanese Patent Publication No. H4-41155, etc. By the production method of α-APM according to the present invention, α-APM, which is important as a sweetener and the like, can be inexpensively produced at high yield.

EXAMPLES

Hereinafter, the present invention will be explained by examples. However, the present invention is not limited to these examples. In addition to confirmation by ninhydrin coloring of thin-film chromatograms (qualitative), quantitative determinations were made by the following high-performance liquid chromatography in order to assay products. Column: InertsiL ODS-2 (manufactured by GL Science, Inc.), eluate: aqueous phosphate solution containing 5.0 mM sodium 1-octanesulfonate (pH 2.1): methanol=100:15 to 50, flow rate: 1.0 mL/min, detection: 210 nanometers (nm).

Example 1

Microbes that produce α-L-aspartyl-L-phenylalanine-β-methyl ester 50 milliliters ("mL" or "ml") of a medium (pH 7.0) containing 20 grams ("g") of glycerol, 5 g of ammonium sulfate, 1 g of potassium dihydrogen phosphate, 3 g of dipotassium hydrogen phosphate, 0.5 g of magnesium sulfate, 10 g of yeast extract and 10 g of peptone in 1 liter (L) that was transferred to a 500 mL Sakaguchi flask and sterilized at 115° C. for 15 minutes (medium 1) was used to culture bacteria and actinomycetes shown in Table 1-1. A slant agar medium (pH 7.0) containing 5 g/L of glucose, 10 g/L of yeast extract, 10 g/L of peptone, 5 g/L of NaCl and 20 g/L of agar in the medium 1 was prepared and a microbe shown in Table 1 was cultured on this slant agar medium at 30° C. for 24 hours. Then, one loopful of the microbe was cultured in the medium 1 at 30° C. for 24 hours, followed by shake culturing at 30° C. and 120 strokes/min for 17 hours. After completion of the culturing, the microbial cells were separated from these culture liquids by centrifugation, and suspended in 0.1 M borate buffer (pH 9.0) containing 10 mM EDTA to 100 g/L as wet microbial cells.

To culture yeast shown in Table 1-1, 50 mL of a medium (pH 6.0) containing 10 g of glucose, 10 g of glycerol, 5 g of ammonium sulfate, 1 g of potassium dihydrogen phosphate, 3 g of dipotassium hydrogen phosphate, 0.5 g of magnesium sulfate, 5 g of yeast extract, 5 g of malt extract and 10 g of peptone in 1 L transferred to a 500-mL Sakaguchi flask and sterilized at 115° C. for 15 minutes (medium 2) was used. A slant agar medium (pH 6.0) containing 5 g/L of glucose, 5 g/L of yeast extract, 5 g/L of malt extract, 10 g/L of peptone, 5 g/L of NaCl and 20 g/L agar in the medium 2 was prepared and a yeast shown in Table 1 was cultured on the slant agar medium at 30° C. for 24 hours. Then, one loopful of the yeast was shake cultured at 30° C. for 24 hours in the medium 2 at 25° C. and 120 strokes/min for 17 hours. After completion of the culturing, the microbial cells were separated from these culture liquids by centrifugation, and suspended in 0.1 M borate buffer (pH 9.0) containing 10 mM EDTA to 100 g/L as wet microbial cells.

The microbes shown in Table 1-2 were cultured as follows. An agar solid medium (pH 7.2, sterilized at 120° C. for 15 minutes) containing 1 g of tryptone, 1 g of yeast extract and 15 g of agar in 1 L of Daigo artificial sea water SP was used to culture *Cellulophaga lytica* NBRC 14961 (Depositary institution; the NITE Biological Resource Center of the National Institute of Technology and Evaluation, address of depositary institution; 5-8 Kazusa-Kamaashi 2-Chome, Kisarazu-shi, Chiba-ken, Japan) or *Flexithrix dorotheae* NBRC 15987 (Depositary institution; the NITE Biological Resource Center of the National Institute of Technology and Evaluation, address of depositary institution; 5-8 Kazusa-Kamaashi 2-Chome, Kisarazu-shi, Chiba-ken, Japan). Microbial cells of *Cellulophaga lytica* NBRC 14961 (Depositary institution; the NITE Biological Resource Center of the National Institute of Technology and Evaluation, address of depositary institution; 5-8 Kazusa-Kamaashi 2-Chome, Kisarazu-shi, Chiba-ken, Japan) or *Flexithrix dorotheae* NBRC 15987 (Depositary institution; the NITE Biological Resource Center of the National Institute of Technology and Evaluation, address of depositary institution; 5-8 Kazusa-Kamaashi 2-Chome, Kisarazu-shi, Chiba-ken, Japan) which was seed cultured on this medium at 30° C. for 48 hours were applied on the same medium, followed by main culturing at 30° C. for 48 hours.

A sheep blood agar medium (Nissui Plate, Nissui Pharmaceutical) was used to culture *Weeksella virosa* NBRC 16016 (Depositary institution; the NITE Biological Resource Center of the National Institute of Technology and Evaluation, address of depositary institution; 5-8 Kazusa-Kamaashi 2-Chome, Kisarazu-shi, Chiba-ken, Japan). Microbial cells of *Weeksella virosa* NBRC 16016 (Depositary institution; the NITE Biological Resource Center of the National Institute of Technology and Evaluation, address of depositary institution; 5-8 Kazusa-Kamaashi 2-Chome, Kisarazu-shi, Chiba-ken, Japan) which was seed cultured on this medium at 30° C. for 48 hours were applied on the same medium, followed by main culturing at 30° C. for 48 hours.

An agar solid medium (pH 7.0, sterilized at 120° C. for 15 minutes) containing 10 g of peptone, 2 g of yeast extract, 1 g of $MgSO_4.7H_2O$ and 15 g of agar in 1 L of distilled water was used to culture *Pedobacter heparinus* NBRC 12017 (Depositary institution; the NITE Biological Resource Center of the National Institute of Technology and Evaluation, address of depositary institution; 5-8 Kazusa-Kamaashi 2-Chome, Kisarazu-shi, Chiba-ken, Japan). Microbial cells of *Pedobacter heparinus* NBRC 12017 (Depositary institution; the NITE Biological Resource Center of the National Institute of Technology and Evaluation, address of depositary institution; 5-8 Kazusa-Kamaashi 2-Chome, Kisarazu-shi, Chiba-ken, Japan) which was seed cultured on this medium at 30° C. for 48 hours were applied on the same medium, followed by main culturing at 30° C. for 48 hours.

An agar solid medium (pH 7.0, sterilized at 120° C. for 15 minutes) containing 0.5 g of $KNO_3$, 0.1 g of sodium glycerophosphate, 1 g of trishydroxymethylaminomethane, 5 g of tryptone, 5 g of yeast extract, 15 g of agar and 1 ml of a trace element solution in 1 L of Daigo artificial sea water SP was used to culture *Persicobacter diffluens* NBRC 15940 ((Depositary institution; the NITE Biological Resource Center of the National Institute of Technology and Evaluation, address of depositary institution; 5-8 Kazusa-Kamaashi 2-Chome, Kisarazu-shi, Chiba-ken, Japan) Note that the trace element solution contained 2.85 g of $H_3BO_4$, 1.8 g of $MnCl_2.4H_2O$, 1.36 g of $FeSO_4.7H_2O$, 26.9 mg of $CuCl_2.2H_2O$, 20.8 mg of $ZnCl_2$, 40.4 mg of $CoCl_2.6H_2O$, 25.2 mg of $Na_2MoO_4.2H_2O$, and 1.77 g of sodium tartrate). Microbial cells of *Persicobacter diffluens* NBRC 15940 (Depositary institution; the NITE Biological Resource Center of the National Institute of Technology and Evaluation, address of depositary institution; 5-8 Kazusa-Kamaashi 2-Chome, Kisarazu-shi, Chiba-ken, Japan) which was seed cultured on this medium at 25° C. for 48 hours were applied on the same medium, followed by main culturing at 25° C. for 48 hours.

An agar solid medium (pH 7.0, sterilized at 120° C. for 15 minutes) containing 3 g of bactocasitone, 1 g of yeast extract, 1.36 g of $CaCl_2.2H_2O$ and 15 g of agar in 1 L of distilled water was used to culture *Chitinophaga pinensis* NBRC 15968 (Depositary institution; the NITE Biological Resource Center of the National Institute of Technology and Evaluation, address of depositary institution; 5-8 Kazusa-Kamaashi 2-Chome, Kisarazu-shi, Chiba-ken, Japan). Microbial cells of *Chitinophaga pinensis* NBRC 15968 (Depositary institution; the NITE Biological Resource Center of the National Institute of Technology and Evaluation, address of depositary institution; 5-8 Kazusa-Kamaashi 2-Chome, Kisarazu-shi, Chiba-ken, Japan) which was seed cultured on this medium at 25° C. for 48 hours were applied on the same medium, followed by main culturing at 25° C. for 48 hours.

An agar solid medium (pH 7.0, sterilized at 120° C. for 15 minutes) containing 5 g of peptone, 1 g of yeast extract, 0.2 g of $FeSO_4.7H_2O$ and 15 g of agar in 1 L of Daigo artificial sea water SP was used to culture *Cyclobacterium marinum* ATCC 25205 (Depositary institution; the American Type Culture Collection, address of depositary institution; P.O. Box 1549, Manassas, Va. 20110, the United States of America). Microbial cells of *Cyclobacterium marinum* ATCC 25205 (Depositary institution; the American Type Culture Collection, address of depositary institution; P.O. Box 1549, Manassas, Va. 20110, the United States of America) which was seed cultured on this medium at 25° C. for 48 hours were applied on the same medium, followed by main culturing at 25° C. for 48 hours.

An agar solid medium (pH 7.0, sterilized at 120° C. for 15 minutes) containing 1 g of peptone, 1 g of yeast extract, 1 g of glucose and 15 g of agar in 1 L of distilled water was used to culture *Runella slithyformis* ATCC 29530 (Depositary institution; the American Type Culture Collection, address of depositary institution; P.O. Box 1549, Manassas, Va. 20110, the United States of America). Microbial cells of *Runella slithyformis* ATCC 29530 (Depositary institution; the American Type Culture Collection, address of depositary institution; P.O. Box 1549, Manassas, Va. 20110, the United States of America) which was seed cultured in this medium at 25° C. for 48 hours were applied on the same medium, followed by main culturing at 25° C. for 48 hours.

An agar solid medium (pH 8.2, sterilized at 120° C. for 15 minutes) containing 0.2 g of nitrilotriacetic acid, 2 ml of a 0.03% $FeCl_3$ solution, 0.12 g of $CaSO_4.2H_2O$, 0.2 g of $MgSO_4.7H_2O$, 0.016 g of NaCl, 0.21 g of $KNO_3$, 1.4 g of $NaNO_3$, 0.22 g of $Na_2HPO_4$, 2 ml of trace element solution and 15 g of agar in 1 L of distilled water was used to culture *Thermonema lapsum* ATCC 43542 ((Depositary institution; the American Type Culture Collection, address of depositary institution; P.O. Box 1549, Manassas, Va. 20110, the United States of America) it should be noted that the trace element solution contained 0.5 ml of $H_2SO_4$, 2.2 g of $MnSO_4$, 0.5 g of $ZnSO_4$, 0.5 g of $H_3BO_3$, 0.016 g of $CuSO_4$, 0.025 g of $Na_2MoO_4$ and 0.046 g of $CoCl_2$). Microbial cells of *Thermonema lapsum* ATCC 43542 (Depositary institution; the American Type Culture Collection, address of depositary institution; P.O. Box 1549, Manassas, Va. 20110, the United States of America) which was seed cultured on this medium at 60° C. for 48 hours were applied on the same medium, followed by main culturing at 25° C. for 48 hours.

Marine Agar 2216 (manufactured by Difco) was used to culture *Gelidibacter algens* ATCC 700364 (Depositary institution; the American Type Culture Collection, address of depositary institution; P.O. Box 1549, Manassas, Va. 20110, the United States of America), *Lewinella cohaerens* ATCC 23123 (Depositary institution; the American Type Culture Collection, address of depositary institution; P.O. Box 1549, Manassas, Va. 20110, the United States of America), *Psychroserpens burtonensis* ATCC 700359 (Depositary institution; the American Type Culture Collection, address of depositary institution; P.O. Box 1549, Manassas, Va. 20110, the United States of America), or *Salegentibacter salegens* DSMZ 5424 (Depositary institution; the Deutche Sammlung von Mikroorganismen and Zellkulturen GmbH (German Collection of Microbes and Cell Cultures, Address of Depositary institution; Mascheroder Weg 1b, 38124 Braunschweig, Germany). In the case of *Gelidibacter algens* ATCC 700364 (Depositary institution; the American Type Culture Collection, address of depositary institution; P.O. Box 1549, Manassas, Va. 20110, the United States of America) or *Psychroserpens burtonensis* ATCC 700359 (Depositary institution; the American Type Culture Collection, address of depositary institution; P.O. Box 1549, Manassas, Va. 20110, the United States of America), microbial cells of *Gelidibacter algens* ATCC 700364, or *Psychroserpens burtonensis* ATCC 700359 (Depositary institution; the American Type Culture Collection, address of depositary institution; P.O. Box 1549, Manassas, Va. 20110, the United States of America) which was seed cultured on this medium at 10° C. for 72 hours were applied, followed by main culturing at 10° C. for 72 hours. In the case of *Lewinella cohaerens* ATCC 23123 (Depositary institution; the American Type Culture Collection, address of depositary institution; P.O. Box 1549, Manassas, Va. 20110, the United States of America), microbial cells of *Lewinella cohaerens* ATCC 23123 (Depositary institution; the American Type Culture Collection, address of depositary institution; P.O. Box 1549, Manassas, Va. 20110, the United States of America) which was seed cultured in this medium at 30° C. for 48 hours were applied on the same medium, followed by main culturing at 30° C. for 48 hours. In the case of *Salegentibacter salegens* DSMZ 5424 (Depositary institution; the Deutche Sammlung von Mikroorganismen und Zellkulturen GmbH (German Collection of Microbes and Cell Cultures, Address of Depositary institution; Mascheroder Weg 1b, 38124 Braunschweig, Germany), microbial cells of *Salegentibacter salegens* DSMZ 5424 (Depositary institution; the Deutche Sammlung von Mikroorganismen und Zellkulturen GmbH (German Collection of Microbes and Cell Cultures, Address of Depositary institution; Mascheroder Weg 1b, 38124 Braunschweig, Germany) which was seed cultured in this medium at 25° C. for 48 hours were applied on the same medium, followed by main culturing at 25° C. for 48 hours.

An agar solid medium (pH 7.0, sterilized at 120° C. for 15 minutes) containing 0.8 g of $NH_4Cl$, 0.25 g of $KH_2PO_4$, 0.4 g of $K_2HPO_4$, 0.505 g of $KNO_3$, 15 mg of $CaCl_2.2H_2O$, 20 mg of $MgCl_2.6H_2O$, 7 mg of $FeSO_4.7H_2O$, 5 mg of $Na_2SO_4$, 5 mg of $MnCl_2.4H_2O$, 0.5 mg of $H_3BO_3$, 0.5 mg of $ZnCl_2$, 0.5 mg of $CoCl_2.6H_2O$, 0.5 mg of $NiSO_4.6H_2O$, 0.3 mg of $CuCl_2.2H_2O$, 10 mg of $Na_2MoO_4.2H_2O$, 0.5 g of yeast extract, 0.5 g of peptone, 0.5 g of casamino acid, 0.5 g of dextrose, 0.5 g of soluble starch, 0.5 g of sodium pyruvate, and 15 g of agar in 1 L of distilled water was used to culture *Dyadobacter fermentans* ATCC 700827 (Depositary institution; the American Type Culture Collection, address of depositary institution; P.O. Box 1549, Manassas, Va. 20110, the United States of America). Microbial cells of *Dyadobacter fermentans* ATCC 700827 (Depositary institution; the American Type Culture Collection, address of depositary institution; P.O. Box 1549, Manassas, Va. 20110, the United States of America) which was seed cultured in this medium at 25° C. for 48 hours, followed by main culturing at 25° C. for 48 hours.

An agar solid medium (pH 7.2, sterilized at 120° C. for 15 minutes) containing 2 g of tryptone, 0.5 g of meat extract, 0.5 g of yeast extract, 0.2 g of sodium acetate and 15 g of agar in 1 L of Daigo artificial sea water SP was used to culture *Flammeovirga aprica* NBRC 15941 (Depositary institution; the NITE Biological Resource Center of the National Institute of Technology and Evaluation, address of depositary institution; 5-8 Kazusa-Kamaashi 2-Chome, Kisarazu-shi, Chiba-ken, Japan). Microbial cells of *Flammeovirga aprica* NBRC 15941 (Depositary institution; the NITE Biological Resource Center of the National Institute of Technology and Evaluation, address of depositary institution; 5-8 Kazusa-Kamaashi 2-Chome, Kisarazu-shi, Chiba-ken, Japan) which was seed cultured in this medium at 25° C. for 48 hours were applied on the same medium, followed by main culturing at 25° C. for 48 hours.

An agar solid medium (pH 7.0, sterilized at 120° C. for 15 minutes) containing 1 g of glucose, 1 g of peptone, 1 g of yeast extract, and 15 g of agar in 1 L of distilled water was used to culture *Spirosoma linguale* DSMZ 74 (Depositary institution; the Deutche Sammlung von Mikroorganismen und Zellkulturen GmbH (German Collection of Microbes and Cell Cultures, Address of Depositary institution; Mascheroder Weg 1b, 38124 Braunschweig, Germany) or *Flectobacillus major* DSMZ 103 (Depositary institution; the Deutche Sammlung von Mikroorganismen und Zellkulturen GmbH (German Collection of Microbes and Cell Cultures, Address of Depositary institution; Mascheroder Weg 1b, 38124 Braunschweig, Germany). Microbial cells of *Spirosoma linguale* DSMZ 74 (Depositary institution; the Deutche Sammlung von Mikroorganismen und Zellkulturen GmbH (German Collection of Microbes and Cell Cultures, Address of Depositary institution; Mascheroder Weg 1b, 38124 Braunschweig, Germany) or *Flectobacillus major* DSMZ 103 (Depositary institution; the Deutche Sammlung von Mikroorganismen und Zellkulturen GmbH (German Collection of Microbes and Cell Cultures, Address of Depositary institution; Mascheroder Weg 1b, 38124 Braunschweig, Germany) which was seed cultured on this medium at 25° C. for 48 hours were applied on the same medium, followed by main culturing at 25° C. for 48 hours.

An agar solid medium (pH 7.0, sterilized at 120° C. for 15 minutes) containing 0.5 g of tryptone, 0.5 g of yeast extract, 0.2 g of meat extract, 0.2 g of sodium acetate and 15 g of agar in 300 ml of distilled water and 700 ml of Daigo artificial sea water SP was used to culture *Tenacibaculum maritimum* ATCC 43398 (Depositary institution; the American Type Culture Collection, address of depositary institution; P.O. Box 1549, Manassas, Va. 20110, the United States of America). Microbial cells of *Tenacibaculum maritimum* ATCC 43398 (Depositary institution; the American Type Culture Collection, address of depositary institution; P.O. Box 1549, Manassas, Va. 20110, the United States of America) which was seed cultured in this medium at 25° C. for 48 hours, followed by main culturing at 25° C. for 48 hours.

An agar solid medium (pH 7.2, sterilized at 120° C. for 15 minutes) containing 2.5 g of yeast extract, 2.5 g of tryptone, 100 mg of nitrilotriacetic acid, 40 mg of $CaSO_4.2H_2O$, 200 mg of $MgCl_2.6H_2O$, 0.5 ml of 0.01M Fe citrate, 0.5 ml of a trace element solution, 100 ml of phosphate buffer, 900 ml of distilled water, and 28 g of agar in 1 L was used to culture *Rhodothermus marinus* DSMZ 4252 (Depositary institution; the Deutche Sammlung von Mikroorganismen und Zellkulturen GmbH (German Collection of Microbes and Cell Cultures, Address of Depositary institution; Mascheroder Weg 1b, 38124 Braunschweig, Germany). Note that the trace element solution contained 12.8 g of nitrilotriacetic acid, 1 g of $FeCl_2.4H_2O$, 0.5 g of $MnCl_2.4H_2O$, 0.3 g of $CoCl_2.4H_2O$, 50 mg of $CuCl_2.2H_2O$, 50 mg of $Na_2MoO_4.2H_2O$, 20 mg of $H_3BO_3$ and 20 mg of $NiCl_2.6H_2O$). Microbial cells of *Rhodothermus marinus* DSMZ 4252 (Depositary institution; the Deutche Sammlung von Mikroorganismen und Zellkulturen GmbH (German Collection of Microbes and Cell Cultures, Address of Depositary institution; Mascheroder Weg 1b, 38124 Braunschweig, Germany) which was seed cultured in this medium at 60° C. for 48 hours were applied on the same medium, followed by main culturing at 60° C. for 48 hours.

An agar solid medium (1.5% agar, pH 7.6, sterilized at 120° C. for 15 minutes) containing BACTO MARINE BROTH (DIFCO 2216) was used to culture *Zobellia galactanivorans* DSMZ 12802 (Depositary institution; the Deutche Sammlung von Mikroorganismen und Zellkulturen GmbH (German Collection of Microbes and Cell Cultures, Address of Depositary institution; Mascheroder Weg 1b, 38124 Braunschweig, Germany). This medium was applied with microbial cells of *Zobellia galactanivorans* DSMZ 12802 (Depositary institution; the Deutche Sammlung von Mikroorganismen und Zellkulturen GmbH (German Collection of Microbes and Cell Cultures, Address of Depositary institution; Mascheroder Weg 1b, 38124 Braunschweig, Germany) which was seed cultured in this medium at 30° C. for 48 hours were applied on the same medium, followed by main culturing at 30° C. for 48 hours.

An agar solid medium (pH 7.2, sterilized at 120° C. for 15 minutes) containing 1.5 g of yeast extract, 2.5 g of peptone, 2 g of hexadecane, 17.7 g of NaCl, 0.48 g of KCl, 3.4 g of $MgCl_2.6H_2O$, 4.46 g of $MgSO_4.7H_2O$, 0.98 g of $CaCl_2$ and 15 g of agar in 1 L of distilled water was used to culture *Muricauda ruestringenesis* DSMZ 13258 (Depositary institution; the Deutche Sammlung von Mikroorganismen und Zellkulturen GmbH (German Collection of Microbes and Cell Cultures, Address of Depositary institution; Mascheroder Weg 1b, 38124 Braunschweig, Germany). Microbial cells of *Muricauda ruestringenesis* DSMZ 13258 (Depositary institution; the Deutche Sammlung von Mikroorganismen und Zellkulturen GmbH (German Collection of Microbes and Cell Cultures, Address of Depositary institution; Mascheroder Weg 1b, 38124 Braunschweig, Germany) which was seed cultured in this medium at 30° C. for 48 hours were applied on the same medium, followed by main culturing at 30° C. for 48 hours.

An agar solid medium (pH 7.2, sterilized at 120° C. for 15 minutes) containing 3 g of casitone, 1 g of yeast extract, 1.36 g of $CaCl_2.2H_2O$ and 15 g of agar in 1 L of distilled water was used to culture *Taxeobacter gelupurpurascens* DSMZ 11116 (Depositary institution; the Deutche Sammlung von Mikroorganismen und Zellkulturen GmbH (German Collection of Microbes and Cell Cultures, Address of Depositary institution; Mascheroder Weg 1b, 38124 Braunschweig, Germany). Microbial cells of *Taxeobacter gelupurpurascens* DSMZ 11116 (Depositary institution; the Deutche Sammlung von Mikroorganismen und Zellkulturen GmbH (German Collection of Microbes and Cell Cultures, Address of Depositary institution; Mascheroder Weg 1b, 38124 Braunschweig, Germany) which was seed cultured in this medium at 30° C. for 48 hours were applied on the same medium, followed by main culturing at 30° C. for 48 hours.

An agar solid medium (pH 7.2, sterilized at 120° C. for 15 minutes) containing 3 g of casitone, 1 g of yeast extract, 1.36 g of $CaCl_2.2H_2O$, 5 g of cellobiose and 15 g of agar in 1 L of distilled water was used to culture *Cytophaga hutchinsonii* NBRC 15051 (Depositary institution; the NITE Biological Resource Center of the National Institute of Technology and Evaluation, address of depositary institution; 5-8 Kazusa-Kamaashi 2-Chome, Kisarazu-shi, Chiba-ken, Japan). Microbial cells of *Cytophaga hutchinsonii* NBRC 15051 (Depositary institution; the NITE Biological Resource Center of the National Institute of Technology and Evaluation, address of depositary institution; 5-8 Kazusa-Kamaashi 2-Chome, Kisarazu-shi, Chiba-ken, Japan) which was seed cultured in this medium at 30° C. for 48 hours were applied on the same medium, followed by main culturing at 30° C. for 48 hours.

An agar solid medium (pH 7.2, sterilized at 120° C. for 15 minutes) containing 10 g of peptone, 2 g of yeast extract, 0.5 g of $MgSO_4.7H_2O$, and 15 g of agar in 250 ml of distilled water and 750 ml of Daigo artificial sea water SP was used to culture *Marinilabilia salmonicolor* NBRC 15948 (Depositary institution; the NITE Biological Resource Center of the National Institute of Technology and Evaluation, address of depositary institution; 5-8 Kazusa-Kamaashi 2-Chome, Kisarazu-shi, Chiba-ken, Japan). Microbial cells of *Marinilabilia salmonicolor* NBRC 15948 (Depositary institution; the NITE Biological Resource Center of the National Institute of Technology and Evaluation, address of depositary institution; 5-8 Kazusa-Kamaashi 2-Chome, Kisarazu-shi, Chiba-ken, Japan) which was seed cultured in this medium at 30° C. for 48 hours were applied on the same medium, followed by main culturing at 30° C. for 48 hours.

An agar solid medium (pH 7.0, sterilized at 120° C. for 15 minutes) containing 0.5 g of $KNO_3$, 0.1 g of sodium glycerophosphate, 1 g of trishydroxymethylaminomethane, 2 g of tryptone, 2 g of yeast extract, 15 g of agar and 1 ml of a trace element solution in 1 L of Daigo artificial sea water SP was used to culture *Saprospira grandis* ATCC 23119 ((Depositary institution; the American Type Culture Collection, address of depositary institution; P.O. Box 1549, Manassas, Va. 20110, the United States of America). Note that the trace element solution contained 2.85 g of $H_3BO_4$, 1.8 g of $MnCl_2.4H_2O$, 1.36 g of $FeSO_4.7H_2O$, 26.9 mg of $CuCl_2.2H_2O$, 20.8 mg of $ZnCl_2$, 40.4 mg of $CoCl_2.6H_2O$, 25.2 mg of $Na_2MoO_4.2H_2O$ and 1.77 g of sodium tartrate). Microbial cells of *Saprospira grandis* ATCC 23119 (Depositary institution; the American Type Culture Collection, address of depositary institution; P.O. Box 1549, Manassas, Va. 20110, the United States of America) which was seed cultured in this medium at 30° C. for 48 hours were applied on the same medium, followed by main culturing at 30° C. for 48 hours.

An agar solid medium (pH 7.5, sterilized at 120° C. for 15 minutes) containing 27 mg of $KH_2PO_4$, 40 mg of $K_2HPO_4$, 40 mg of $Na_2HPO_4.2H_2O$, 50 mg of $CaCl_2.2H_2O$, 75 mg of $MgSO_4.7H_2O$, 5 mg of $FeCl_3.6H_2O$, 3 mg of $MnSO_4.H_2O$, 1.31 g of glutamic acid, 2.5 mg of Trypticase Soy Broth without glucose, 0.4 mg of thiamine, 0.01 mg of vitamin B12, 2 g of glucose, and 1 ml of a trace element solution in 1 L of distilled water was used to culture *Haliscomenobacter hydrossis* ATCC 27775 ((Depositary institution; the American Type Culture Collection, address of depositary institution; P.O. Box 1549, Manassas, Va. 20110, the United States of America). Note that the trace element solution contained 0.1 g of $ZnSO_4.7H_2O$, 0.03 g of $MnCl_2.4H_2O$, 0.3 g of $H_3BO_3$, 0.2 g of $CoCl_2.6H_2O$, 0.01 g of $CuCl_2.2H_2O$, 0.02 g of $NiCl_2.6H_2O$ and 0.03 g of $Na_2MoO_4.H_2O$). Microbial cells of *Haliscomenobacter hydrossis* ATCC 27775 (Depositary institution; the American Type Culture Collection, address of depositary institution; P.O. Box 1549, Manassas, Va. 20110, the United States of America) which was seed cultured in this medium at 25° C. for 48 hours were applied on the same medium, followed by main culturing at 25° C. for 48 hours.

The thus obtained microbial cells were each collected from the agar medium, and suspended in 0.1 M borate buffer (pH 9.0) containing 10 mM EDTA to 100 g/L as wet microbial cells.

To 0.1 mL each of the microbial cell suspensions of these microbes was added 0.1 mL of 100 mM borate buffer (pH 9.0) containing 10 mM EDTA, 100 mM L-aspartic acid-α,β-dimethyl ester hydrochloride and 200 mM L-phenylalanine to make the total amount 0.2 mL. Then, reaction was carried out at 20° C. for 3 hours when the microbe shown in Table 1-1 was used or for 1 hour when the microbe shown in Table 1-2 was used. The amount (mM) of α-L-aspartyl-L-phenylalanine-β-methyl ester (α-AMP) produced is shown in Tables 1-1 and 1-2. Note that no (3-AMP was detected in all the cases where the microbes were used.

TABLE 1-1

| Microbe | α-AMP (mM) |
|---|---|
| *Aeromonas hydrophila* ATCC 13136 | 1.55 |
| *Azotobacter vinelandii* IFO 3741 | 0.15 |
| *Alcaligenes faecalis* FERM P-8460 | 0.37 |
| *Brevibacterium minutiferuna* FERM BP-8277 | 0.10 |
| *Corynebacterium flavescens* ATCC 10340 | 0.26 |
| *Escherichia coli* FERM BP-8276 | 3.68 |
| *Empedobacter brevis* ATCC 14234 | 6.31 |
| *Flavobacterium resinovorum* ATCC 14231 | 0.62 |
| *Microbacterium arborescens* ATCC 4348 | 0.08 |
| *Propionibacterium shermanii* BERM BP-8100 | 3.41 |
| *Brevibacillus parabrevis* ATCC 8185 | 0.08 |
| *Paenibacillus alvei* IFO 14175 | 0.09 |
| *Pseudomonas fragi* IFO 3458 | 0.84 |
| *Serratia grimesii* ATCC 14460 | 0.47 |
| *Stenotrophomonas maltophilia* ATCC 13270 | 0.18 |
| *Sphingobacterium* sp. FERM BP-8124 | 5.97 |
| *Streptomyces lavendulae* NRRL B-1305 | 0.89 |
| *Xanthomonas maltophilia* FERM BP-5568 | 0.40 |
| *Williopsis saturnus* IFO 0895 | 0.05 |
| *Candida magnoliae* IFO 0705 | 0.26 |
| *Geotrichum amycelium* CBS 152.25 | 0.19 |
| *Geotrichum amycelium* IFO 0905 | 0.06 |
| *Saccharomyces unisporus* IFO 0724 | 0.07 |
| *Torulaspora delbrueckii* IFO 0422 | 0.04 |
| *Pichia ciferrii* IFO 0905 | 0.06 |

TABLE 1-2

| Microbe | α-AMP (mM) | Microbe | α-AMP (mM) |
|---|---|---|---|
| *Cellulophaga lytica* NBRC 14961 | tr | *Spirosoma linguale* DSMZ 74 | 0.15 |
| *Weeksella virosa* NBRC 16016 | tr | *Flectobacillus major* DSMZ 103 | 0.68 |
| *Pedobacter heparinus* NBRC 12017 | 0.07 | *Tenacibaculum maritimum* ATCC 43398 | tr |
| *Persicobacter diffluens* NBRC 15940 | tr | *Rhodotermus marinus* DSMZ 4252 | 0.06 |
| *Flexithrix dorotheae* NBRC 15987 | 2.47 | *Zobellia galactanivorans* DSMZ 12802 | 0.42 |
| *Chitinophaga pinensis* NBRC 15968 | 0.08 | *Muricauda ruestringensis* DSMZ 13258 | 0.51 |
| *Cyclobacterium marinum* ATCC 25205 | 0.91 | *Salegentibacter salegens* DSMZ 5424 | tr |

TABLE 1-2-continued

| Microbe | α-AMP (mM) | Microbe | α-AMP (mM) |
|---|---|---|---|
| *Runella slithyformis* ATCC 29530 | 0.07 | *Taxeobacter gelupurpurascens* DSMZ 11116 | 0.02 |
| *Thermonema lapsum* ATCC 43542 | tr | *Cytophaga hutchinsonii* NBRC 15051 | tr |
| *Psychroserpens burtonensis* ATCC 700359 | 0.09 | *Marinilabilia salmonicolor* NBRC 15948 | 0.02 |
| *Gelidibacter algens* ATCC 700364 | 0.07 | *Lewinella cohaerens* ATCC 23123 | 0.33 |
| *Dyadobacter fermentans* ATCC 700827 | 0.04 | *Saprospira grandis* ATCC 23119 | 0.03 |
| *Flammeovirga aprica* NBRC 15941 | 0.08 | *Haliscomenobacter hydrossis* ATCC 27775 | tr |

Reference Example 1

Microbe that produces β-L-aspartyl-L-phenyl-alanine-α-methyl ester

Microbes shown in Table 2 were cultured similarly to the procedure in bacteria in Table 1 of Example 1. After completion of the culturing, the microbial cells were separated from these culture broths by centrifugation, and suspended in 0.1 M borate buffer (pH 9.0) containing 10 mM EDTA to 100 g/L as wet microbial cells. To 0.1 mL each of the microbial cell suspensions of these microbes was added 0.1 mL of 100 mM borate buffer (pH 9.0) containing 10 mM EDTA, 100 mM L-aspartic acid-α,β-dimethyl ester hydrochloride and 200 mM L-phenylalanine to make the total amount 0.2 ml, followed by reaction at 30° C. for 2 hours. The amount (mM) of β-L-aspartyl-L-phenylalanine-α-methyl ester (β-AMP) produced in this case is indicated in Table 2. Note that no α-AMP was detected in all the microbes.

TABLE 2

| Microbe | β-AMP (mM) |
|---|---|
| *Hafnia alvei* ATCC 9760 | 0.30 |
| *Klebsiella pneumoniae* ATCC 8308 | 0.26 |

Example 2

Purification of Enzyme from *Empedobacter brevis*

A 50 mL medium (pH 6.2) containing 5 grams (g) of glucose, 5 g of ammonium sulfate, 1 g of monopotassium phosphate, 3 g of dipotassium phosphate, 0.5 g of magnesium sulfate, 10 g of yeast extract and 10 g of peptone in 1 liter (L) was transferred to a 500 mL Sakaguchi flask and sterilized at 115° C. for 15 minutes. This medium was then inoculated with 2 milliliters (ml or mL) of *Empedobacter brevis* strain FERM BP-8113 (Depositary institution: the independent administrative corporation, National Institute of Advanced Industrial Science and Technology, International Patent Organism Depositary, Address of depositary institution: Chuo Dai-6, 1-1 Higashi 1-Chome, Tsukuba-shi, Ibaraki-ken, Japan, International deposit transfer date: Jul. 8, 2002) that had been cultured at 30° C. for 16 hours in the same medium, followed by shake culturing at 30° C. and 120 strokes/min for 16 hours.

Subsequently, the procedure after centrifugal separation was carried out either on ice or at 4° C. The obtained culture broth was centrifuged to collect microbial cells. After washing 16 g of the microbial cells with 50 mM Tris-HCl buffer (pH 8.0), they were suspended in 40 milliliters (ml or mL) of the same buffer and subjected to ultrasonic crushing treatment for 45 minutes at 195 watts. This ultrasonically crushed liquid was then centrifuged (10,000 rpm, 30 minutes) to remove the crushed cell fragments and obtain an ultrasonic crushed liquid supernatant. This ultrasonic crushed liquid supernatant was dialyzed overnight against 50 mM Tris-HCl buffer (pH 8.0) followed by removal of the insoluble fraction by ultracentrifugation (50,000 rpm, 30 minutes) to obtain a soluble fraction in the form of the supernatant liquid. The resulting soluble fraction was applied to a Q-Sepharose HP column (manufactured by Amersham) pre-equilibrated with Tris-HCl buffer (pH 8.0), and the active fraction was collected from the non-adsorbed fraction. This active fraction was dialyzed overnight against 50 mM acetate buffer (pH 4.5) followed by removal of the insoluble fraction by centrifugal separation (10,000 rpm, 30 minutes) to obtain a dialyzed fraction in the form of the supernatant liquid. This dialyzed fraction was then applied to a Mono S column (manufactured by Amersham) pre-equilibrated with 50 mM acetate buffer (pH 4.5) to elute enzyme at a linear concentration gradient of the same buffer containing 0 to 1 M NaCl. The fraction that had the lowest level of contaminating protein among the active fractions was applied to a Superdex 200pg column (manufactured by Amersham) pre-equilibrated with 50 mM acetate buffer (pH 4.5) containing 1 M NaCl, and gel filtration was performed by allowing the same buffer (pH 4.5) containing 1 M NaCl to flow through the column to obtain an active fraction solution. As a result of performing these procedures, the peptide-forming enzyme used in the present invention was confirmed to have been uniformly purified based on the experimental results of electrophoresis. The enzyme recovery rate in the aforementioned purification process was 12.2% and the degree of purification was 707 times.

Example 3

Production of α-L-aspartyl-L-phenylalanine-β-methyl ester using enzyme fraction of *Empedobacter brevis*

10 microliters (μl) of Mono S fraction enzyme (about 20 U/ml) obtained in Example 2 was added to 190 μl of borate buffer (pH 9.0) containing 105.3 mM L-aspartic acid-α,β-dimethyl ester hydrochloride, 210.5 mM L-phenylalanine and 10.51 mM EDTA and reaction was carried out at 20° C. The course of production of α-L-aspartyl-L-phenylalanine-β-methyl ester (α-AMP) is shown in Table 3. Note that almost no formation of α-L-aspartyl-L-phenylalanine-β-methyl ester was confirmed in the enzyme-not-added lot.

Further, 10 μl of Mono S fraction enzyme (about 20 U/ml) obtained in Example 2 was added to 190 μl of borate buffer (pH 9.0) containing each of 105.3 mM L-aspartic acid-α-methyl ester hydrochloride and L-aspartic acid-β-methyl ester hydrochloride, 210.5 mM L-phenylalanine and 10.51 mM EDTA was added and reaction was carried out at 20° C. As a result, no formation of the corresponding peptides was observed.

TABLE 3

| Reaction time (minute) | Produced α-AMP (mM) |
|---|---|
| 30 | 23.0 |
| 60 | 42.1 |
| 120 | 61.7 |

Example 4

Purification of Enzyme from *Sphingobacterium* sp.

*Sphingobacterium* sp. strain FERM BP-8124 (Depositary institution: the independent administrative corporation, National Institute of Advanced Industrial Science and Technology, International Patent Organism Depositary, Address of depositary institution: Chuo Dai-6, 1-1 Higashi 1-Chome, Tsukuba-shi, Ibaraki-ken, Japan, International deposit date: Jul. 22, 2002) was cultured in the same manner as that in Example 2 using the medium shown in Example 2. The following procedure after centrifugal separation was carried out either on ice or at 4° C. The obtained culture broth was centrifuged (10,000 rpm, 15 minutes) to collect microbial cells. After washing 2 g of the microbial cells with 20 mM Tris-HCl buffer (pH 7.6), they were suspended in 8 ml of the same buffer and subjected to ultrasonic crushing treatment for 45 minutes at 195 W. This ultrasonically crushed liquid was then centrifuged (10,000 rpm, 30 minutes) to remove the crushed cell fragments to obtain an ultrasonically crushed liquid supernatant. This ultrasonically crushed liquid supernatant was dialyzed overnight against 20 mM Tris-HCl buffer (pH 7.6) followed by removal of the insoluble fraction by ultracentrifugation (50,000 rpm, 30 minutes) to obtain a soluble fraction in the form of the supernatant liquid. The resulting soluble fraction was applied to a Q-Sepharose HP column (manufactured by Amersham) pre-equilibrated with Tris-HCl buffer (pH 7.6), and the active fraction was collected from the non-adsorbed fraction. This active fraction was dialyzed overnight against 20 mM acetate buffer (pH 5.0) followed by removal of the insoluble fraction by centrifugal separation (10,000 rpm, 30 minutes) to obtain a dialyzed fraction in the form of the supernatant liquid. This dialyzed fraction was then applied to an SP-Sepharose HP column (manufactured by Amersham) pre-equilibrated with 20 mM acetate buffer (pH 5.0) to obtain the active fraction in which enzyme was eluted at a linear concentration gradient of the same buffer containing 0 to 1 M NaCl.

Example 5

Production of α-L-aspartyl-L-phenylalanine-β-methyl ester and α-L-aspartyl-L-phenylalanine-β-ethyl ester using enzyme fraction of *Sphingobacterium* sp.

In the case of production of α-L-aspartyl-L-phenylalanine-β-methyl ester (α-AMP), 15 μl of concentrated solution of SP-Sepharose HP fraction (about 15 U/ml) obtained in Example 4 was added to 185 μl of borate buffer (pH 9.0) containing 108.1 mM L-aspartic acid-α,β-dimethyl ester hydrochloride, 216.2 mM L-phenylalanine and 10.8 mM EDTA and reaction was carried out at 20° C. Similarly, in the case of production of α-L-aspartyl-L-phenylalanine-β-ethyl ester (α-AEP), 10 μl of a concentrated solution of SP-Sepharose HP fraction (about 15 U/ml) obtained in Example 4 was added to 190 μl of borate buffer (pH 9.0) containing 52.6 mM L-aspartic acid-α,β-diethyl ester hydrochloride, 105.2 mM L-phenylalanine and 10.8 mM EDTA and reaction was carried out at 20° C. The course of formation of AMP or AEP is shown in Table 4. Note that almost no formation of AMP or AEP was confirmed in the enzyme-not-added lot. For formation of AEP, numerical values obtained by using a standard product of AMP are described.

TABLE 4

| Reaction time (minute) | Produced α-AMP (mM) | Produced α-AEP (mM) |
|---|---|---|
| 30 | 25.8 | 7.5 |
| 60 | 40.7 | 13.3 |
| 120 | 56.0 | 20.6 |
| 180 | 61.8 | — |

Example 6

Isolation of Peptide-Forming Enzyme Gene Derived from *Empedobacter brevis*

Hereinafter, isolation of a peptide-forming enzyme gene will be explained. *Empedobacter brevis* strain FERM BP-8113 (Depositary institution: the independent administrative corporation, National Institute of Advanced Industrial Science and Technology, International Patent Organism Depositary, Address of depositary institution: Chuo Dai-6, 1-1 Higashi 1-Chome, Tsukuba-shi, Ibaraki-ken, Japan, International deposit transfer date: Jul. 8, 2002) was used as the microbe. In isolating the gene, *Escherichia coli* JM-109 was used as a host while pUC118 was used as a vector.

(1) Production of PCR Primer Based on Determined Internal Amino Acid Sequence

A mixed primer having the base sequences indicated in SEQ ID NO.: 3 and SEQ ID NO: 4, respectively, was produced based on the amino acid sequences (SEQ ID NOs: 1 and 2) determined according to the Edman's decomposition method from the digestion product of lysyl endopeptidase of a peptide-forming enzyme derived from the *Empedobacter brevis* strain FERM BP-8113 (Depositary institution: the independent administrative corporation, National Institute of Advanced Industrial Science and Technology, International Patent Organism Depositary, Address of depositary institution: Chuo Dai-6, 1-1 Higashi 1-Chome, Tsukuba-shi, Ibaraki-ken, Japan, International deposit transfer date: Jul. 8, 2002).

(2) Acquisition of Microbial Cells

*Empedobacter brevis* strain FERM BP-8113 (Depositary institution: the independent administrative corporation, National Institute of Advanced Industrial Science and Technology, International Patent Organism Depositary, Address of depositary institution: Chuo Dai-6, 1-1 Higashi 1-Chome, Tsukuba-shi, Ibaraki-ken, Japan, International deposit transfer date: Jul. 8, 2002) was cultured at 30° C. for 24 hours on a CM2G agar medium (containing glucose at 50 g/l, yeast extract at 10 g/l, peptone at 10 g/l, sodium chloride at 5 g/l, and agar at 20 g/l, pH 7.0). One loopful of the resulting microbial cells was inoculated into a 500 ml Sakaguchi flask containing 50 ml of a CM2G liquid medium (the aforementioned medium excluding agar) followed by shake culturing at 30° C.

(3) Acquisition of Chromosomal DNA from Microbial Cells 50 ml of culture broth was centrifuged (12,000 rpm, 4° C., 15 minutes) to collect the microbial cells. Then, a chromosomal DNA was acquired from the microbial cells using the QIAGEN Genomic-Tip System (Qiagen) based on the procedure described in the manual therefor.

(4) Acquisition of DNA Fragment Containing Part of Peptide-Forming Enzyme Gene by PCR A DNA fragment containing a portion of the peptide-forming enzyme gene derived from *Empedobacter brevis* strain FERM BP-8113 (Depositary institution: the independent administrative corporation, National Institute of Advanced Industrial Science and Technology, International Patent Organism Depositary, Address of depositary institution: Chuo Dai-6, 1-1 Higashi 1-Chome, Tsukuba-shi, Ibaraki-ken, Japan, International deposit transfer date: Jul. 8, 2002) was acquired by the PCR method using LA-Taq (manufactured by Takara Shuzo). A PCR reaction was then carried out on a chromosomal DNA acquired from *Empedobacter brevis* strain FERM BP-8113 (Depositary institution: the independent administrative corporation, National Institute of Advanced Industrial Science and Technology, International Patent Organism Depositary, Address of depositary institution: Chuo Dai-6, 1-1 Higashi 1-Chome, Tsukuba-shi, Ibaraki-ken, Japan, International deposit transfer date: Jul. 8, 2002) using the primers having the base sequences of SEQ ID NOs: 3 and 4.

The PCR reaction was carried out for 30 cycles under the following conditions using the Takara PCR Thermal Cycler PERSONAL (manufactured by Takara Shuzo).

| | |
|---|---|
| 94° C. | 30 seconds |
| 52° C. | 1 minute |
| 72° C. | 1 minute |

After completion of the reaction, 3 µl of the reaction liquid was applied to 0.8% agarose electrophoresis. As a result, it was verified that a DNA fragment of about 1.5 kilobases (kb) was amplified.

(5) Cloning of Peptide-Forming Enzyme Gene from Gene Library

In order to acquire the entire length of peptide-forming enzyme gene in full-length, Southern hybridization was carried out using the DNA fragment amplified in the PCR procedure as a probe. The procedure for Southern hybridization is explained in Molecular Cloning, 2nd edition, Cold Spring Harbor Press (1989).

The approximately 1.5 kb DNA fragment amplified by the PCR procedure was isolated by 0.8% agarose electrophoresis. The target band was then cut out and purified. This The DNA fragment was labeled with probe digoxinigen using DIG High Prime (manufactured by Boehringer-Mannheim) based on the procedure described in the manual therefor using DIG High Prime (manufactured by Boehringer-Mannheim).

After completely digesting the chromosomal DNA of *Empedobacter brevis* acquired in the step (3) of the present Example 6 by reacting at 37° C. for 16 hours with restriction enzyme HindIII, the resultant was electrophoresed with on 0.8% agarose gel. The electrophoresed chromosomal DNA was blotted onto a positively charged Nylon membrane filter (manufactured by Roche Diagnostics) from the agarose gel after the electrophoresis, followed by treatments consisting of alkaline denaturation, neutralization and immobilization. Hybridization was carried out using EASY HYB (manufactured by Boehringer-Mannheim). After pre-hybridizing the filter at 50° C. for 1 hour, the probe labeled with digoxinigen prepared as described above was added and hybridization was carried out at 50° C. for 16 hours. Subsequently, the filter was washed for 20 minutes at room temperature with 2×SSC containing 0.1% SDS. Moreover, the filter was additionally washed twice at 65° C. for 15 minutes with 0.1×SSC containing 0.1% SDS.

Detection of bands that hybridized with the probe was carried out using the DIG Nucleotide Detection Kit (manufactured by Boehringer-Mannheim) based on the procedure described in the manual therefor using the DIG Nucleotide Detection Kit (manufactured by Boehringer-Mannheim). As a result, a roughly 4 kb band was able to be detected that hybridized with the probe.

Then, 5 µg of the chromosomal DNA prepared in the step (3) of the present Example 6 was completely digested with HindIII. A roughly 4 kb of DNA was separated by 0.8% agarose gel electrophoresis, followed by purification of the DNA using the Gene Clean II Kit (manufactured by Funakoshi) and dissolving the DNA in 10 µl of TE. 4 µl of this product was then mixed with pUC118 HindIII/BAP (manufactured by Takara Shuzo) and a ligation reaction was carried out using the DNA Ligation Kit Ver. 2 (manufactured by Takara Shuzo). 5 µl of the ligation reaction mixture and 100 µl of competent cells of *Escherichia coli* JM109 (manufactured by Toyobo) were mixed to transform the *Escherichia coli*. This was then applied to a suitable solid medium to produce a chromosomal DNA library.

To acquire the entire full-length of peptide-forming enzyme gene, the chromosomal DNA library was screened by colony hybridization using the aforementioned probe. The procedure for colony hybridization is explained in Molecular Cloning, 2nd edition, Cold Spring Harbor Press (1989).

The colonies of the chromosomal DNA library were transferred to a Nylon membrane filter (Nylon Membrane for Colony and Plaque Hybridization, (manufactured by Roche Diagnostics) followed by treatments consisting of alkali denaturation, neutralization and immobilization. Hybridization was carried out using EASY HYB (manufactured by Boehringer-Mannheim). After pre-hybridizing the filter at 37° C. for 1 hour, the aforementioned probe labeled with digoxinigen was added, followed by hybridization at 50° C. for 16 hours. Subsequently, the filter was washed for 20 minutes at room temperature with 2×SSC containing 0.1% SDS. Moreover, the filter was additionally washed twice at 65° C. for 15 minutes with 0.1×SSC containing 0.1% SDS.

Detection of colonies that hybridized with the labeled probe was carried out using the DIG Nucleotide Detection Kit (manufactured by Boehringer-Mannheim) based on the explanation described in the manual therefor using the DIG Nucleotide Detection Kit (manufactured by Boehringer-Mannheim). As a result, two strains of colonies were verified to hybridize with the labeled probe.

(6) Base Sequence of Peptide-Forming Enzyme Gene Derived from *Empedobacter brevis*

Plasmids possessed by *Escherichia coli* JM109 were prepared from the aforementioned two strains of microbial cells that were verified to hybridize with the labeled probe using the Wizard Plus Minipreps DNA Purification System (manufactured by Promega) to and the base sequence of a portion where hybridization with the probe occurred and nearby was determined. The sequencing reaction was carried out using the CEQ DTCS-Quick Start Kit (manufactured by Beckman-Coulter) based on the procedure described in the manual therefor. In addition, electrophoresis was carried out using the CEQ 2000-XL (manufactured by Beckman-Coulter).

As a result, it was verified that an open reading frame that encodes a protein containing the internal amino acid sequences of the peptide-forming enzyme (SEQ ID NOs: 1 and 2) did exist, thereby confirming that the open reading frame was a gene encoding the peptide-forming enzyme. The base sequence of the full-length of the peptide-forming enzyme genes along with the corresponding amino acid sequences is shown in SEQ ID NO: 5 of the Sequence Listing. As a result of analysis on the homology of the resulting open reading frame with the BLASTP program, homology was discovered between the two enzymes; it showed with a homology of 34% as at the amino acid sequence level exhibited with the α-amino acid ester hydrolase of *Acetobacter pasteurianus* (see Appl. Environ. Microbiol., 68(1), 211-218 (2002), and a homology of 26% at the amino acid sequence level exhibited with the glutaryl-7ACA acylase of *Brevibacillus laterosporum* (see J. Bacteriol., 173(24), 7848-7855 (1991).

(7) Expression of Peptide-Forming Enzyme Gene Derived from *Empedobacter brevis* in *Escherichia coli*

A target gene region on the promoter region of the trp operon on the chromosomal DNA of *Escherichia coli* W3110 was amplified by carrying out PCR using the oligonucleotides indicated in SEQ ID NOs: 7 and 8 as primers, and the resulting DNA fragments were ligated to a pGEM-Teasy vector (manufactured by Promega). *E. coli* JM109 was then transformed in this ligation solution, and those strains having the target plasmid in which the direction of the inserted trp promoter is inserted in the opposite to the orientation from of the lac promoter were selected from ampicillin-resistant strains. Next, a DNA fragment containing the trp promoter obtained by treating this plasmid with EcoO109I/EcoRI was ligated to an EcoO109I/EcoRI treatment product of pUC19 (manufactured by Takara). *Escherichia coli* JM109 was then transformed with this ligation solution and those strains having the target plasmid were selected from ampicillin-resistant strains. Next, a DNA fragment obtained by treating this plasmid with HindIII/PvuII was ligated with to a DNA fragment containing an rrnB terminator obtained by treating pKK223-3 (manufactured by Amersham Pharmacia) with HindIII/HincII. *E. coli* JM109 was then transformed with this ligation solution, strains having the target plasmid were selected from ampicillin-resistant strains, and the plasmid was designated as pTrpT.

The target gene was amplified by PCR using the chromosomal DNA of *Empedobacter brevis* strain FERM BP-8113 (Depositary institution: the independent administrative corporation, National Institute of Advanced Industrial Science and Technology, International Patent Organism Depositary, Address of depositary institution: Chuo Dai-6, 1-1 Higashi 1-Chome, Tsukuba-shi, Ibaraki-ken, Japan, International deposit transfer date: Jul. 8, 2002) as a template and the oligonucleotides indicated in SEQ ID NO: 9 and 10 as primers. This DNA fragment was then treated with NdeI/PstI, and the resulting DNA fragment was ligated with the NdeI/PstI treatment product of pTrpT. *Escherichia coli* JM109 was then transformed with this ligation solution, those strains having the target plasmid were selected from ampicillin-resistant strains, and this plasmid was designated as pTrpT_Gtg2.

*Escherichia coli* JM109 having pTrpT_Gtg2 was seed cultured at 30° C. for 24 hours in LB medium containing 100 mg/l of ampicillin. 1 ml of the resulting culture broth was seeded in a 500 ml Sakaguchi flask containing 50 ml of a medium (D glucose at 2 g/l, yeast extract at 10 g/l, casamino acids at 10 g/l, ammonium sulfate at 5 g/l, potassium dihydrogen phosphate at 3 g/l, dipotassium hydrogen phosphate at 1 g/l, magnesium sulfate heptahydrate at 0.5 g/l, and ampicillin at 100 mg/l), followed by culturing at 25° C. for 24 hours. The culture broth had an α-L-aspartyl-phenylalanine-β-methyl ester forming activity of 0.11 U per 1 ml of culture broth and it was verified that the cloned gene was expressed by *E. coli*. Furthermore, no activity was detected for a transformant in which only pTrpT had been introduced as a control.

Prediction of Signal Sequence

When the amino acid sequence of SEQ ID NO: 6 described in the Sequence Listing was analyzed with the Signal P v 1.1 program (see Protein Engineering, Vol. 12, No. 1, pp. 3-9, 1999), it was predicted that amino acids numbers 1 to 22 function as a signal that is secreted into the periplasm, while the mature protein was estimated to be downstream of amino acid number 23.

Verification of Secretion

*Escherichia coli* JM109, having pTrpT_Gtg2, was seed cultured at 30° C. for 24 hours in LB medium containing 100 mg/l of ampicillin. 1 ml of the resulting culture broth was seeded into a 500 ml Sakaguchi flask containing 50 ml of medium (glucose at 2 g/l, yeast extract at 10 g/l, casamino acids at 10 g/l, ammonium sulfate at 5 g/l, potassium dihydrogen phosphate at 3 g/l, dipotassium hydrogen phosphate at 1 g/l, magnesium sulfate heptahydrate at 0.5 g/l, and ampicillin at 100 mg/l), followed by final culturing at 25° C. for 24 hours to obtain cultured microbial cells.

The cultured microbial cells were fractionated into a periplasm fraction and a cytoplasm fraction by an osmotic pressure shock method using a 20 grams/deciliter (g/dl) sucrose solution. The microbial cells immersed in the 20 g/dl sucrose solution were immersed in a 5 mM aqueous $MgSO_4$ solution. The centrifuged supernatant was named a periplasm fraction ("Pe"). In addition, the centrifuged sediment was, re-suspended and subjected to ultrasonic crushing. The resultant was named a cytoplasm fraction ("Cy"). The activity of glucose 6-phosphate dehydrogenase, which is known to be present in the cytoplasm, was used as an indicator to verify that the cytoplasm had been separated. This measurement was carried out by adding a suitable amount of enzyme to a reaction solution at 30° C. containing 1 mM glucose 6-phosphate, 0.4 mM NADP, 10 mM $MgSO_4$, and 50 mM Tris-Cl (pH 8), followed by measurement of absorbance at 340 nm to measure production of NADPH.

The amounts of enzymes of in the periplasm fraction and the cytoplasm fraction when the activity of a separately prepared cell-free extract was assigned a value of 100% are shown in FIG. 1. That glucose 6-phosphate dehydrogenase activity did not mix in the periplasm fraction indicates that the periplasm fraction did not mix in the cytoplasm fraction. About 60% of the α-L-aspartyl-L-phenylalanine-β-methyl ester (α-AMP) forming activity was recovered in the periplasm fraction, and it was verified that the Ala-Gln-forming enzyme was secreted into the periplasm as predicted from the amino acid sequence using the Signal P v 1.1 program.

Example 7

Isolation of Peptide-forming Enzyme Gene Derived from *Sphingobacterium* sp.

Hereinafter, isolation of a peptide-forming enzyme gene is described. The microbe used was *Sphingobacterium* sp. strain FERM BP-8124 (Depositary institution: the independent administrative corporation, National Institute of Advanced Industrial Science and Technology, International Patent Organism Depositary, Address of depositary institution: Chuo Dai-6, 1-1 Higashi 1-Chome, Tsukuba-shi, Ibaraki-ken, Japan, International deposit date: Jul. 22, 2002). For the isolation of the gene, *Escherichia coli* DH5α was used as a host, and pUC118 was used as a vector.

(1) Acquisition of Microbial Cells

*Sphingobacterium* sp. strain FERM BP-8124 (Depositary institution: the independent administrative corporation, National Institute of Advanced Industrial Science and Technology, International Patent Organism Depositary, Address of depositary institution: Chuo Dai-6, 1-1 Higashi 1-Chome, Tsukuba-shi, Ibaraki-ken, Japan, International deposit date: Jul. 22, 2002) was cultured for 24 hours at 25° C. on a CM2G agar medium (containing glucose at 50 g/l, yeast extract at 10 g/l, peptone at 10 g/l, sodium chloride at 5 g/l, and agar at 20 g/l, pH 7.0). One loopful of the resulting microbial cells was inoculated into a 500 ml Sakaguchi flask containing 50 ml of CM2G liquid medium (the aforementioned medium excluding agar) followed by shake culturing at 25° C.

(2) Acquisition of Chromosomal DNA from Microbial Cells 50 ml of culture broth was centrifuged (12,000 rpm, 4° C., 15 minutes) to collect the microbial cells. A chromosomal DNA was then acquired from the microbial cells using the Qiagen Genomic-Tip System (Qiagen) based on the procedure described in the manual therefor.

(3) Acquisition of Probe DNA Fragment by PCR

A DNA fragment containing a portion of the peptide-forming enzyme gene derived from *Empedobacter brevis* strain FERM BP-8113 (Depositary institution: the independent administrative corporation, National Institute of Advanced Industrial Science and Technology, International Patent Organism Depositary, Address of depositary institution: Chuo Dai-6, 1-1 Higashi 1-Chome, Tsukuba-shi, Ibaraki-ken, Japan, International deposit transfer date: Jul. 8, 2002) was acquired by the PCR method using LA-Taq (manufactured by Takara Shuzo). A PCR reaction was then carried out on the chromosomal DNA acquired from *Empedobacter brevis* strain FERM BP-8113 (Depositary institution: the independent administrative corporation, National Institute of Advanced Industrial Science and Technology, International Patent Organism Depositary, Address of depositary institution: Chuo Dai-6, 1-1 Higashi 1-Chome, Tsukuba-shi, Ibaraki-ken, Japan, International deposit transfer date: Jul. 8, 2002) using primers having the base sequences of SEQ ID NOs: 3' and 4.

The PCR reaction was carried out using the Takara PCR Thermal Cycler—PERSONAL (Takara Shuzo) for 30 cycles under the following conditions.

| | |
|---|---|
| 94° C. | 30 seconds |
| 52° C. | 1 minute |
| 72° C. | 1 minute |

After completion of the reaction, 3 µl of reaction liquid was applied to 0.8% agarose electrophoresis. As a result, it was verified that a DNA fragment of about 1.5 kb was amplified.

(4) Cloning of Peptide-forming Enzyme Gene from Gene Library

In order to acquire the full-length peptide-forming enzyme gene, Southern hybridization was carried out using the DNA fragment amplified in the aforementioned PCR procedure as a probe. The operations of Southern hybridization are explained in Molecular Cloning, 2nd edition, Cold Spring Harbor Press (1989).

The approximately 1.5 kb DNA fragment amplified by the aforementioned PCR procedure was separated by 0.8% agarose electrophoresis. The target band was then cut out and purified. This DNA fragment was labeled with probe digoxinigen using DIG High Prime (manufactured by Boehringer-Mannheim) based on the procedure described in the manual therefor.

After allowing the chromosomal DNA of *Sphingobacterium* sp. acquired in the step (2) of the present Example 7 to react with restriction enzyme SacI at 37° C. for 16 hours to completely digest the DNA, the resultant was electrophoresed on 0.8% agarose gel. From the agarose gel after the electrophoresis, the electrophoresed chromosomal DNA was blotted onto a positively charged Nylon membrane filter (manufactured by Roche Diagnostics), followed by treatments consisting of alkali denaturation, neutralization, and immobilization. Hybridization was carried out using EASY HYB (manufactured by Boehringer-Mannheim). After pre-hybridizing the filter at 37° C. for 1 hour, the digoxinigen-labeled probe prepared as described above was added and hybridization was carried out at 37° C. for 16 hours. Subsequently, the filter was washed twice at 60° C. with 1×SSC containing 0.1% SDS.

Detection of bands that hybridized with the probe was carried out using the DIG Nucleotide Detection Kit (Boehringer-Mannheim) based on the procedure described in the manual therefor. As a result, a roughly 3 kb band was successfully detected that hybridized with the probe.

5 µg of the chromosomal DNA prepared in the step (2) of the present Example 7 was completely digested with SacI. About 3 kb of a DNA was separated by 0.8% agarose gel electrophoresis, the DNA was purified using the Gene Clean II Kit (manufactured by Funakoshi), and dissolved in 10 µl of TE. 4 µl of the resulting solution and pUC118 treated with alkaline phosphatase (*E. coli* C75) at 37° C. for 30 minutes and at 50° C. for 30 minutes, after reaction with SacI at 37° C. for 16 hours to completely digest, were mixed and a ligation reaction was carried out using the DNA Ligation Kit Ver. 2 (manufactured by Takara Shuzo). 5 µl of this ligation reaction liquid and 100 µl of competent cells of *Escherichia coli* DH5α (manufactured by Takara Shuzo) were mixed to transform the *Escherichia coli*. This was then applied to a suitable solid medium to produce a chromosomal DNA library.

To acquire full-length peptide-forming enzyme gene, the chromosomal DNA library was screened by colony hybridization using the aforementioned probe. The procedure for colony hybridization is explained in Molecular Cloning, 2nd edition, Cold Spring Harbor Press (1989).

The colonies of the chromosomal DNA library were transferred to a Nylon membrane filter (Nylon Membrane for Colony and Plaque Hybridization, manufactured by Roche Diagnostics), followed by treatments of alkali denaturation, neutralization, and immobilization. Hybridization was carried out using EASY HYB (manufactured by Boehringer-Mannheim). After pre-hybridizing the filter at 37° C. for 1 hour, the aforementioned digoxinigen-labeled probe was added, followed by hybridization at 37° C. for 16 hours. Subsequently, the filter was washed twice at 60° C. with 1×SSC containing 0.1% SDS.

Detection of colonies that hybridized with the labeled probe was carried out using the DIG Nucleotide Detection Kit (manufactured by Boehringer-Mannheim) based on the explanation described in the manual therefor. As a result, six strains of colonies were verified to have hybridized with the labeled probe.

(5) Base Sequence of Peptide-forming Enzyme Gene Derived from *Sphingobacterium* sp.

Plasmids possessed by *Escherichia coli* DH5α were prepared from the six strains of microbial cells that were verified to have hybridized with the labeled probe using the Wizard Plus Minipreps DNA Purification System (manufactured by Promega) to determine the base sequence of a portion where hybridization with the probe occurred and nearby was determined. The sequencing reaction was carried out using the CEQ DTCS-Quick Start Kit (manufactured by Beckman-Coulter) based on the procedure described in the manual therefor. In addition, electrophoresis was carried out using the CEQ 2000-XL (manufactured by Beckman-Coulter).

As a result, it revealed that an open reading frame that encodes peptide-forming enzyme did exist. The full-length base sequence of the peptide-forming enzyme gene derived from *Sphingobacterium* sp. along with the corresponding amino acid sequence is shown in SEQ ID NO: 11. Peptide-forming enzyme derived from *Sphingobacterium* sp. exhibited a homology of 63.5% at the amino acid sequence level to the peptide-forming enzyme derived from *Empedobacter brevis* (as determined using the BLASTP program).

(6) Expression of Peptide-forming Enzyme Gene Derived from *Sphingobacterium* sp. in *Escherichia coli*

The target gene was amplified by PCR using the chromosomal DNA of *Sphingobacterium* sp. FERM BP-8124 (Depositary institution: the independent administrative corporation, National Institute of Advanced Industrial Science and Technology, International Patent Organism Depositary, Address of depositary institution: Chuo Dai-6, 1-1 Higashi 1-Chome, Tsukuba-shi, Ibaraki-ken, Japan, International deposit date: Jul. 22, 2002) as a template and the oligonucleotides shown in SEQ ID NOs: 13 and 14 as primers. This DNA fragment was treated with NdeI/XbaI, and the resulting DNA fragment and an NdeI/XbaI treatment product of pTrpT were ligated. *Escherichia coli* JM109 was then transformed with this ligation solution, and strains having the target plasmid were selected from ampicillin-resistant strains. The plasmid was designated as pTrpT_Sm_aet.

*Escherichia coli* JM109 having pTrpT_Sm_aet was cultured at 25° C. for 20 hours by inoculating one loopful thereof into an ordinary test tube containing 3 ml of a medium (glucose at 2 g/l, yeast extract at 10 g/l, casamino acids at 10 g/l, ammonium sulfate at 5 g/l, potassium dihydrogen phosphate at 3 g/l, dipotassium hydrogen phosphate at 1 g/l, magnesium sulfate heptahydrate at 0.5 g/l and ampicillin at 100 mg/l). It was verified that a cloned gene having an α-AMP production activity of 0.53 U per ml of culture broth was expressed by *Escherichia coli*. Furthermore, no activity was detected for a transformant containing only pTrpT used as a control.

Prediction of Signal Sequence

When the amino acid sequence of SEQ ID NO: 12 described in the Sequence Listing was analyzed with the Signal P v 1.1 program (Protein Engineering, Vol. 12, No. 1, pp. 3-9, 1999), it was predicted that amino acids numbers 1 to 20 function as a signal that is secreted into the periplasm, while the mature protein was estimated to be downstream of amino acid number 21.

Confirmation of Signal Sequence

One loopful of *Escherichia coli* JM109, having pTrpT_Sm_aet, was inoculated into ordinary test tubes containing 50 ml of a medium (glucose at 2 g/l, yeast extract at 10 g/l, casamino acids at 10 g/l, ammonium sulfate at 5 g/l, potassium dihydrogen phosphate at 3 g/l, dipotassium hydrogen phosphate at 1 g/l, magnesium sulfate heptahydrate at 0.5 g/l and ampicillin at 100 mg/l) and main culturing was performed at 25° C. for 20 hours.

Hereinafter, procedures after centrifugal separation were carried out either on ice or at 4° C. After completion of the culturing, the microbial cells were separated from the culture broth by centrifugation, washed with 100 mM phosphate buffer (pH 7), and then suspended in the same buffer. The microbial cells were then subjected to ultrasonic crushing treatment for 20 minutes at 195 W, the ultrasonic crushed liquid was centrifuged (12,000 rpm, 30 minutes) to remove the crushed cell fragments and obtain a soluble fraction. The resulting soluble fraction was applied to a CHT-II column manufactured by Biorad) pre-equilibrated with 100 mM phosphate buffer (pH 7), and enzyme was eluted at a linear concentration gradient with 500 mM phosphate buffer. A solution obtained by mixing the active fraction with 5 time volumes of 2 M ammonium sulfate and 100 mM phosphate buffer was applied to a Resource-PHE column (manufactured by Amersham) pre-equilibrated with 2 M ammonium sulfate and 100 mM phosphate buffer, and an enzyme was eluted at a linear concentration gradient by 2 to 0 M ammonium sulfate to obtain an active fraction solution. As a result of these procedures, it was verified that the peptide-forming enzyme was electrophoretically uniformly purified.

When the amino acid sequence of the aforementioned peptide-forming enzyme was determined by Edman's decomposition method, the amino acid sequence of SEQ ID NO: 15 was acquired, and the mature protein was verified to be downstream of amino acid number 21 as was predicted by the Signal P v 1.1 program.

Example 8

Isolation of Peptide-forming Enzyme Gene Derived from *Pedobacter heparinus* IFO 12017

Hereinafter, isolation of a peptide-forming enzyme gene is described. The microbe used is *Pedobacter heparinus* IFO 12017 (Depositary institution; the Institute of Fermentation, Osaka, address of the depositary institution; 2-17-85 Jusanbon-cho, Yodogawa-ku, Osaka-shi, Japan). For the isolation of the gene, *Escherichia coli* JM109 was used as a host, and pUC118 was used as a vector.

(1) Acquisition of Microbial Cells

*Pedobacter heparinus* IFO 12017 (Depositary institution: the Institute of Fermentation, Osaka; 2-17-85 Jusanbon-cho, Yodogawa-ku, Osaka-shi, Japan) was cultured for 24 hours at 25° C. on a CM2G agar medium (containing glucose at 50 g/l, yeast extract at 10 g/l, peptone at 10 g/l, sodium chloride at 5 g/l, and agar at 20 g/l, pH 7.0). One loopful of the resulting microbial cells was inoculated into a 500 ml Sakaguchi flask containing 50 ml of CM2G liquid medium (the aforementioned medium excluding agar) followed by shake culturing at 25° C.

(2) Acquisition of Chromosomal DNA from Microbial Cells 50 ml of the culture broth was centrifuged (12,000 rpm, 4° C., 15 minutes) to collect the microbial cells. A chromosomal DNA was then acquired from the microbial cells using the Qiagen Genomic-Tip System (Qiagen) based on the procedure described in the manual therefor.

(3) Acquisition of Probe DNA Fragment by PCR

A DNA fragment containing a portion of the peptide-forming enzyme gene derived from *Pedobacter heparinus* IFO 12017 (Depositary institution: the Institute of Fermentation, Osaka; 2-17-85 Jusanbon-cho, Yodogawa-ku, Osaka-shi, Japan) was acquired by the PCR method using LA-Taq (manufactured by Takara Shuzo). A PCR reaction was then carried out on the chromosomal DNA acquired from *Pedobacter heparinus* IFO 12017 (Depositary institution: the Institute of Fermentation, Osaka; 2-17-85 Jusanbon-cho, Yodogawa-ku, Osaka-shi, Japan) using primers having the base sequences of SEQ ID NOs: 15 and 16. The approximately 1 kb DNA fragment amplified by the PCR procedure was isolated by 0.8% agarose electrophoresis. The target band was then cut out and purified. The DNA fragment was labeled with probe digoxinigen using DIG High Prime (manufactured by Boehringer-Mannheim) based on the procedure described in the manual therefor.

(4) Cloning of Peptide-forming Enzyme Gene from Gene Library

To acquire the full-length peptide-forming enzyme gene, Southern hybridization was carried out using the DNA fragment amplified in the aforementioned PCR procedure as a probe. The operations of Southern hybridization are explained in Molecular Cloning, 2nd edition, Cold Spring Harbor Press (1989).

After allowing the chromosomal DNA of *Pedobacter heparinus* IFO 12017 (Depositary institution: the Institute of Fermentation, Osaka; 2-17-85 Jusanbon-cho, Yodogawa-ku, Osaka-shi, Japan) to react with restriction enzyme HindIII at 37° C. for 16 hours to completely digest the DNA, the resultant was electrophoresed on 0.8% agarose gel. From the agarose gel after the electrophoresis, the electrophoresed chromosomal DNA was blotted onto a positively charged Nylon membrane filter (manufactured by Roche Diagnostics), followed by treatments consisting of alkali denaturation, neutralization, and immobilization. Hybridization was carried out using EASY HYB (manufactured by Boehringer-Mannheim). After pre-hybridizing the filter at 50° C. for 1 hour, the digoxinigen-labeled probe prepared as described above was added and hybridization was carried out at 50° C. for 16 hours. Subsequently, the filter was washed twice at 60° C. with 1×SSC containing 0.1% SDS.

Detection of bands that hybridized with the probe was carried out using the DIG Nucleotide Detection Kit (Boehringer-Mannheim) based on the procedure described in the manual therefor. As a result, a roughly 5 kb band was successfully detected that hybridized with the probe.

5 μg of the chromosomal DNA of *Pedobacter heparinus* IFO 12017 was completely digested with HindIII. About 5 kb of a DNA was separated by 0.8% agarose gel electrophoresis, the DNA was purified using the Gene Clean II Kit (manufactured by Funakoshi), and dissolved in 10 μl of TE. 4 μl of the resulting solution and pUC118 HindIII/BAP were mixed were mixed and a ligation reaction was carried out using the DNA Ligation Kit Ver. 2 (manufactured by Takara Shuzo). 5 μl of this ligation reaction liquid and 100 μl of competent cells of *Escherichia coli* JM109 (manufactured by Takara Shuzo) were mixed to transform the *Escherichia coli*. This was then applied on a suitable solid medium to produce a chromosomal DNA library.

To acquire a full-length peptide-forming enzyme gene, the chromosomal DNA library was screened by colony hybridization using the aforementioned probe. The procedure for colony hybridization is explained in Molecular Cloning, 2nd edition, Cold Spring Harbor Press (1989).

The colonies of the chromosomal DNA library were transferred to a Nylon membrane filter, Nylon Membrane for Colony and Plaque Hybridization (manufactured by Roche Diagnostics), followed by treatments of alkali denaturation, neutralization, and immobilization. Hybridization was carried out using EASY HYB (manufactured by Boehringer-Mannheim). After pre-hybridizing the filter at 37° C. for 1 hour, the aforementioned digoxinigen-labeled probe was added, followed by hybridization at 37° C. for 16 hours. Subsequently, the filter was washed twice at 60° C. with 1×SSC containing 0.1% SDS.

Detection of colonies that hybridized with the labeled probe was carried out using the DIG Nucleotide Detection Kit (manufactured by Boehringer-Mannheim) based on the explanation described in the manual therefor. As a result, one strain whose colony hybridized with the labeled probe was observed.

(5) Base Sequence of Peptide-forming Enzyme Gene Derived from *Pedobacter heparinus* IFO 12017

Plasmids possessed by *Escherichia coli* JM109 were prepared from the strain that was verified to have hybridized with the labeled probe and the base sequence of a portion where hybridization with the probe occurred and nearby was determined. The sequencing reaction was carried out using the CEQ DTCS-Quick Start Kit (manufactured by Beckman-Coulter) based on the procedure described in the manual therefor. In addition, electrophoresis was carried out using the CEQ 2000-XL (manufactured by Beckman-Coulter).

As a result, it revealed that an open reading frame that encodes peptide-forming enzyme did exist. The full-length base sequence of the peptide-forming enzyme gene derived from *Pedobacter heparinus* IFO 12017 (Depositary institution: the Institute of Fermentation, Osaka; 2-17-85 Jusanbon-cho, Yodogawa-ku, Osaka-shi, Japan) along with the corresponding amino acid sequence is shown in SEQ ID NO: 17.

Example 9

Expression of Peptide-forming Enzyme Gene Derived from *Pedobacter heparinus* IFO 12017 in *Escherichia coli*

The target gene was amplified by PCR using the chromosomal DNA of *Pedobacter heparinus* IFO 12017 (Depositary institution: the Institute of Fermentation, Osaka; 2-17-85 Jusanbon-cho, Yodogawa-ku, Osaka-shi, Japan) as a template and the oligonucleotides shown in SEQ ID NOs: 19 and 20 as primers. This DNA fragment was treated with NdeI/HindIII, and the resulting DNA fragment and an NdeI/HindIII treatment product of pTrpT were ligated. *Escherichia coli* JM109 was then transformed with this ligation solution, and strains having the target plasmid were selected from ampicillin-resistant strains. The plasmid was designated as pTrpT_Ph_aet.

One loopful of *Escherichia coli* JM109 having pTrpT_Ph_aet was inoculated in an ordinary test tube containing 3 ml of a medium (glucose at 2 g/l, yeast extract at 10 g/l, casamino acids at 10 g/l, ammonium sulfate at 5 g/l, potassium dihydrogen phosphate at 3 g/l, dipotassium hydrogen phosphate at 1 g/l, magnesium sulfate heptahydrate at 0.5 g/l and ampicillin at 100 mg/l) and main culturing was performed at 25° C. for 20 hours. It was verified that the cultured broth had an α-AMP production activity of 0.01 U per ml of culture broth so that it was verified that the cloned gene was expressed in *Escherichia coli*. Furthermore, no activity was detected in the transformant containing only pTrpT used as a control.

Example 10

Isolation of Peptide-forming Enzyme Gene Derived from *Taxeobacter gelupurpurascens* DSMZ 11116

Hereinafter, isolation of a peptide-forming enzyme gene is described. The microbe used is *Taxeobacter gelupurpurascens* DSMZ 11116 (Depositary institution; the Deutche Sammlung von Mikroorganismen und Zellkulturen GmbH (German Collection of Microbes and Cell Cultures); address of the depositary institution; Mascheroder Weg 1b, 38124 Braunschweig, Germany). For the isolation of the gene, *Escherichia coli* JM109 was used as a host, and pUC118 was used as a vector.

(1) Acquisition of Microbial Cells

*Taxeobacter gelupurpurascens* DSMZ 11116 (Depositary institution; the Deutche Sammlung von Mikroorganismen und Zellkulturen GmbH (German Collection of Microbes and Cell Cultures, Address of Depositary institution; Mascheroder Weg 1b, 38124 Braunschweig, Germany) was cultured for 24 hours at 25° C. on a CM2G agar medium (containing glucose at 50 g/l, yeast extract at 10 g/l, peptone at 10 g/l, sodium chloride at 5 g/l, and agar at 20 g/l, pH 7.0). One loopful of the resulting microbial cells was inoculated into a 500 ml Sakaguchi flask containing 50 ml of CM2G liquid medium (the aforementioned medium excluding agar) followed by shake culturing at 25° C.

(2) Acquisition of Chromosomal DNA from Microbial Cells 50 ml of the culture broth was centrifuged (12,000 rpm, 4° C., 15 minutes) to collect the microbial cells. A chromosomal DNA was then acquired from the microbial cells using the Qiagen Genomic-Tip System (Qiagen) based on the procedure described in the manual therefor.

(3) Acquisition of Probe DNA Fragment by PCR

A DNA fragment containing a portion of the peptide-forming enzyme gene derived from *Taxeobacter gelupurpurascens* DSMZ 11116 (Depositary institution; the Deutche Sammlung von Mikroorganismen und Zellkulturen GmbH (German Collection of Microbes and Cell Cultures, Address of Depositary institution; Mascheroder Weg 1b, 38124 Braunschweig, Germany) was acquired by the PCR method using LA-Taq (manufactured by Takara Shuzo). A PCR reaction was then carried out on the chromosomal DNA acquired from *Taxeobacter gelupurpurascens* DSMZ 11116 (Depositary institution; the Deutche Sammlung von Mikroorganismen und Zellkulturen GmbH (German Collection of Microbes and Cell Cultures, Address of Depositary institution; Mascheroder Weg 1b, 38124 Braunschweig, Germany) using primers having the base sequences of SEQ ID NOs: 21 and 16. The approximately 1 kb DNA fragment amplified by the PCR procedure was isolated by 0.8% agarose electrophoresis. The target band was then cut out and purified. The DNA fragment was labeled with probe digoxinigen using DIG High Prime (manufactured by Boehringer-Mannheim) based on the procedure described in the manual therefor.

(4) Cloning of Peptide-Forming Enzyme Gene from Gene Library

To acquire the full-length peptide-forming enzyme gene, Southern hybridization was carried out using the DNA fragment amplified in the aforementioned PCR procedure as a probe. The operations of Southern hybridization are explained in Molecular Cloning, 2nd edition, Cold Spring Harbor Press (1989).

After allowing the chromosomal DNA of *Taxeobacter gelupurpurascens* DSMZ 11116 (Depositary institution; the Deutche Sammlung von Mikroorganismen und Zellkulturen GmbH (German Collection of Microbes and Cell Cultures, Address of Depositary institution; Mascheroder Weg 1b, 38124 Braunschweig, Germany) to react with restriction enzyme PstI at 37° C. for 16 hours to completely digest the DNA, the resultant was electrophoresed on 0.8% agarose gel. From the agarose gel after the electrophoresis, the electrophoresed chromosomal DNA was blotted onto a positively charged Nylon membrane filter (manufactured by Roche Diagnostics), followed by treatments consisting of alkali denaturation, neutralization, and immobilization. Hybridization was carried out using EASY HYB (manufactured by Boehringer-Mannheim). After pre-hybridizing the filter at 50° C. for 1 hour, the digoxinigen-labeled probe prepared as described above was added and hybridization was carried out at 50° C. for 16 hours. Subsequently, the filter was washed twice at 60° C. with 1×SSC containing 0.1% SDS.

Detection of bands that hybridized with the probe was carried out using the DIG Nucleotide Detection Kit (Boehringer-Mannheim) based on the procedure described in the manual therefor. As a result, a roughly 5 kb band was successfully detected that hybridized with the probe.

5 μg of the chromosomal DNA of *Taxeobacter gelupurpurascens* DSMZ 11116 (Depositary institution; the Deutche Sammlung von Mikroorganismen and Zellkulturen GmbH (German Collection of Microbes and Cell Cultures, Address of Depositary institution; Mascheroder Weg 1b, 38124 Braunschweig, Germany) was completely digested with PstI. About 5 kb of a DNA was separated by 0.8% agarose gel electrophoresis, the DNA was purified using the Gene Clean II Kit (manufactured by Funakoshi), and dissolved in 10 μl of TE. 4 μl of the resulting solution and pUC118 PstI/BAP (manufactured by Takara Shuzo) were mixed were mixed and a ligation reaction was carried out using the DNA Ligation Kit Ver. 2 (manufactured by Takara Shuzo). 5 μl of this ligation reaction liquid and 100 μl of competent cells of *Escherichia coli* JM109 (manufactured by Takara Shuzo) were mixed to transform the *Escherichia coli*. This was then applied on a suitable solid medium to produce a chromosomal DNA library.

To acquire a full-length peptide-forming enzyme gene, the chromosomal DNA library was screened by colony hybridization using the aforementioned probe. The procedure for colony hybridization is explained in Molecular Cloning, 2nd edition, Cold Spring Harbor Press (1989).

The colonies of the chromosomal DNA library were transferred to a Nylon membrane filter, Nylon Membrane for Colony and Plaque Hybridization (manufactured by Roche Diagnostics), followed by treatments of alkali denaturation, neutralization, and immobilization. Hybridization was carried out using EASY HYB (manufactured by Boehringer-Mannheim). After pre-hybridizing the filter at 37° C. for 1 hour, the aforementioned digoxinigen-labeled probe was added, followed by hybridization at 37° C. for 16 hours. Subsequently, the filter was washed twice at 60° C. with 1×SSC containing 0.1% SDS.

Detection of colonies that hybridized with the labeled probe was carried out using the DIG Nucleotide Detection Kit (manufactured by Boehringer-Mannheim) based on the explanation described in the manual therefor. As a result, one strain whose colony hybridized with the labeled probe was observed.

(5) Base Sequence of Peptide-Forming Enzyme Gene Derived from *Taxeobacter gelupurpurascens* DSMZ 11116

Plasmids possessed by *Escherichia coli* JM109 were prepared from the strain that was verified to have hybridized with the labeled probe and the base sequence of a portion where hybridization with the probe occurred nearby was determined. The sequencing reaction was carried out using the CEQ DTCS-Quick Start Kit (manufactured by Beckman-Coulter) based on the procedure described in the manual therefor. In addition, electrophoresis was carried out using the CEQ 2000-XL (manufactured by Beckman-Coulter).

As a result, it revealed that an open reading frame that encodes peptide-forming enzyme did exist. The full-length base sequence of the peptide-forming enzyme gene derived from *Taxeobacter gelupurpurascens* DSMZ 11116 along with the corresponding amino acid sequence is shown in SEQ ID NO: 22.

Example 11

Isolation of Peptide-Forming Enzyme Gene Derived from *Cyclobacterium marinum* ATCC 25205

Hereinafter, isolation of a peptide-forming enzyme gene is described. The microbe used is *Cyclobacterium marinum* ATCC 25205 (Depositary institution; the American Type Culture Collection, address of depositary institution; P.O. Box 1549, Manassas, Va. 20110, the United States of America). For the isolation of the gene, *Escherichia coli* JM109 was used as a host, and pUC118 was used as a vector.

(1) Acquisition of Microbial Cells

*Cyclobacterium marinum* ATCC 25205 (Depositary institution; the American Type Culture Collection, address of depositary institution; P.O. Box 1549, Manassas, Va. 20110, the United States of America) was cultured for 24 hours at 25° C. on a CM2G agar medium (containing glucose at 50 g/l, yeast extract at 10 g/l, peptone at 10 g/l, sodium chloride at 5 g/l, and agar at 20 g/l, pH 7.0). One loopful of the resulting microbial cells was inoculated into a 500 ml Sakaguchi flask containing 50 ml of CM2G liquid medium (the aforementioned medium excluding agar) followed by shake culturing at 25° C.

(2) Acquisition of Chromosomal DNA from Microbial Cells 50 ml of the culture broth was centrifuged (12,000 rpm, 4° C., 15 minutes) to collect the microbial cells. A chromosomal DNA was then acquired from the microbial cells using the Qiagen Genomic-Tip System (Qiagen) based on the procedure described in the manual therefor.

(3) Acquisition of Probe DNA Fragment by PCR

A DNA fragment containing a portion of the peptide-forming enzyme gene derived from *Cyclobacterium marinum* ATCC 25205 was acquired by the PCR method using LA-Taq (manufactured by Takara Shuzo). A PCR reaction was then carried out on the chromosomal DNA acquired from *Cyclobacterium marinum* ATCC 25205 (Depositary institution; the American Type Culture Collection, address of depositary institution; P.O. Box 1549, Manassas, Va. 20110, the United States of America) using primers having the base sequences of SEQ ID NOs: 15 and 16. The approximately 1 kb DNA fragment amplified by the PCR procedure was isolated by 0.8% agarose electrophoresis. The target band was then cut out and purified. The DNA fragment was labeled with probe digoxinigen using DIG High Prime (manufactured by Boehringer-Mannheim) based on the procedure described in the manual therefor.

(4) Cloning of Peptide-Forming Enzyme Gene from Gene Library

To acquire the full-length peptide-forming enzyme gene, Southern hybridization was carried out using the DNA fragment amplified in the aforementioned PCR procedure as a probe. The operations of Southern hybridization are explained in Molecular Cloning, 2nd edition, Cold Spring Harbor Press (1989).

After allowing the chromosomal DNA of *Cyclobacterium marinum* ATCC 25205 (Depositary institution; the American Type Culture Collection, address of depositary institution; P.O. Box 1549, Manassas, Va. 20110, the United States of America) to react with restriction enzyme PstI or HincII at 37° C. for 16 hours to completely digest the DNA, the resultant was electrophoresed on 0.8% agarose gel. From the agarose gel after the electrophoresis, the electrophoresed chromosomal DNA was blotted onto a positively charged Nylon membrane filter (manufactured by Roche Diagnostics), followed by treatments consisting of alkali denaturation, neutralization, and immobilization. Hybridization was carried out using EASY HYB (manufactured by Boehringer-Mannheim). After pre-hybridizing the filter at 50° C. for 1 hour, the digoxinigen-labeled probe prepared as described above was added and hybridization was carried out at 50° C. for 16 hours. Subsequently, the filter was washed twice at 60° C. with 1×SSC containing 0.1% SDS.

Detection of bands that hybridized with the probe was carried out using the DIG Nucleotide Detection Kit (Boehringer-Mannheim) based on the procedure described in the manual therefor. As a result, a 7 kb band that hybridized with the probe was successfully detected for the PstI-digested product and a 2 kb band that hybridized with the probe was successfully detected for the HincII-digested product.

5 μg of the chromosomal DNA of *Cyclobacterium marinum* ATCC 25205 (Depositary institution; the American Type Culture Collection, address of depositary institution; P.O. Box 1549, Manassas, Va. 20110, the United States of America) was completely digested with PstI or HincII. About 7 kb or 2 kb DNA was separated by 0.8% agarose gel electrophoresis. The DNA was purified using the Gene Clean II Kit (manufactured by Funakoshi) and dissolved in 10 μl of TE. 4 μl of the resulting solution and pUC118 PstI/BAP (manufactured by Takara Shuzo) or pUC118 HincII/BAP (manufactured by Takara Shuzo) were mixed and a ligation reaction was carried out using the DNA Ligation Kit Ver. 2 (manufactured by Takara Shuzo). 5 μl of this ligation reaction liquid and 100 μl of competent cells of *Escherichia coli* JM109 (manufactured by Takara Shuzo) were mixed to transform the *Escherichia coli*. This was then applied on a suitable solid medium to produce a chromosomal DNA library.

To acquire a full-length peptide-forming enzyme gene, the chromosomal DNA library was screened by colony hybridization using the aforementioned probe. The procedure for colony hybridization is explained in Molecular Cloning, 2nd edition, Cold Spring Harbor Press (1989).

The colonies of the chromosomal DNA library were transferred to a Nylon membrane filter, Nylon Membrane for Colony and Plaque Hybridization (manufactured by Roche Diagnostics), followed by treatments of alkali denaturation, neutralization, and immobilization. Hybridization was carried out using EASY HYB (manufactured by Boehringer-Mannheim). After pre-hybridizing the filter at 37° C. for 1 hour, the aforementioned digoxinigen-labeled probe was added, followed by hybridization at 37° C. for 16 hours. Subsequently, the filter was washed twice at 60° C. with 1×SSC containing 0.1% SDS.

Detection of colonies that hybridized with the labeled probe was carried out using the DIG Nucleotide Detection Kit (manufactured by Boehringer-Mannheim) based on the explanation described in the manual therefor. As a result, one strain each whose colony hybridized with the labeled probe was observed.

(5) Base Sequence of Peptide-Forming Enzyme Gene Derived from *Cyclobacterium marinum* ATCC 25205

Plasmids possessed by *Escherichia coli* JM109 were prepared from each strain that was verified to have hybridized with the labeled probe and the base sequence of a portion where hybridization with the probe occurred and nearby was determined. The sequencing reaction was carried out using the CEQ DTCS-Quick Start Kit (manufactured by Beckman-Coulter) based on the procedure described in the manual therefor. In addition, electrophoresis was carried out using the CEQ 2000-XL (manufactured by Beckman-Coulter).

As a result, it revealed that an open reading frame that encodes peptide-forming enzyme did exist. The full-length base sequence of the peptide-forming enzyme gene derived from *Cyclobacterium marinum* ATCC 25205 (Depositary institution; the American Type Culture Collection, address of depositary institution; P.O. Box 1549, Manassas, Va. 20110, the United States of America) along with the corresponding amino acid sequence is shown in SEQ ID NO: 24.

Example 12

Isolation of Peptide-Forming Enzyme Gene Derived from *Psychroserpens burtonensis* ATCC 700359

Hereinafter, isolation of a peptide-forming enzyme gene is described. The microbe used is *Psychroserpens burtonensis* ATCC 700359 (Depositary institution; the American Type Culture Collection, address of depositary institution; P.O. Box 1549, Manassas, Va. 20110, the United States of America). For the isolation of the gene, *Escherichia coli* JM109 was used as a host, and pUC118 was used as a vector.

(1) Acquisition of Microbial Cells

*Psychroserpens burtonensis* ATCC 700359 (Depositary institution; the American Type Culture Collection, address of depositary institution; P.O. Box 1549, Manassas, Va. 20110, the United States of America) was cultured for 24 hours at 25°

C. on a CM2G agar medium (containing glucose at 50 g/l, yeast extract at 10 g/l, peptone at 10 g/l, sodium chloride at 5 g/l, and agar at 20 g/l, pH 7.0). One loopful of the resulting microbial cells was inoculated into a 500 ml Sakaguchi flask containing 50 ml of CM2G liquid medium (the aforementioned medium excluding agar) followed by shake culturing at 10° C.

(2) Acquisition of Chromosomal DNA from Microbial Cells 50 ml of the culture broth was centrifuged (12,000 rpm, 4° C., 15 minutes) to collect the microbial cells. A chromosomal DNA was then acquired from the microbial cells using the Qiagen Genomic-Tip System (Qiagen) based on the procedure described in the manual therefor.

(3) Acquisition of Probe DNA Fragment by PCR

A DNA fragment containing a portion of the peptide-forming enzyme gene derived from *Psychroserpens burtonensis* ATCC 700359 (Depositary institution; the American Type Culture Collection, address of depositary institution; P.O. Box 1549, Manassas, Va. 20110, the United States of America) was acquired by the PCR method using LA-Taq (manufactured by Takara Shuzo). A PCR reaction was then carried out on the chromosomal DNA acquired from *Psychroserpens burtonensis* ATCC 700359 (Depositary institution; the American Type Culture Collection, address of depositary institution; P.O. Box 1549, Manassas, Va. 20110, the United States of America) using primers having the base sequences of SEQ ID NOs: 15 and 16. The approximately 1 kb. DNA fragment amplified by the PCR procedure was isolated by 0.8% agarose electrophoresis. The target band was then cut out and purified. The DNA fragment was labeled with probe digoxinigen using DIG High Prime (manufactured by Boehringer-Mannheim) based on the procedure described in the manual therefor.

(4) Cloning of Peptide-Forming Enzyme Gene from Gene Library

To acquire the full-length peptide-forming enzyme gene, Southern hybridization was carried out using the DNA fragment amplified in the aforementioned PCR procedure as a probe. The operations of Southern hybridization are explained in Molecular Cloning, 2nd edition, Cold Spring Harbor Press (1989).

After allowing the chromosomal DNA of *Psychroserpens burtonensis* ATCC 700359 to react with restriction enzyme EcoRI at 37° C. for 16 hours to completely digest the DNA, the resultant was electrophoresed on 0.8% agarose gel. From the agarose gel after the electrophoresis, the electrophoresed chromosomal DNA was blotted onto a positively charged Nylon membrane filter (manufactured by Roche Diagnostics), followed by treatments consisting of alkali denaturation, neutralization, and immobilization. Hybridization was carried out using EASY HYB (manufactured by Boehringer-Mannheim). After pre-hybridizing the filter at 50° C. for 1 hour, the digoxinigen-labeled probe prepared as described above was added and hybridization was carried out at 50° C. for 16 hours. Subsequently, the filter was washed twice at 60° C. with 1×SSC containing 0.1% SDS.

Detection of bands that hybridized with the probe was carried out using the DIG Nucleotide Detection Kit (Boehringer-Mannheim) based on the procedure described in the manual therefor. As a result, a roughly 7 kb band was successfully detected that hybridized with the probe.

5 μg of the chromosomal DNA of *Psychroserpens burtonensis* ATCC 700359 was completely digested with EcoRI. About 7 kb of a DNA was separated by 0.8% agarose gel electrophoresis, the DNA was purified using the Gene Clean II Kit (manufactured by Funakoshi), and dissolved in 10 μl of TE. 4 μl of the resulting solution and pUC118 EcoRI/BAP (manufactured by Takara Shuzo) were mixed were mixed and a ligation reaction was carried out using the DNA Ligation Kit Ver. 2 (manufactured by Takara Shuzo). 5 μl of this ligation reaction liquid and 100 μl of competent cells of *Escherichia coli* JM109 (manufactured by Takara Shuzo) were mixed to transform the *Escherichia coli*. This was then applied on a suitable solid medium to produce a chromosomal DNA library.

To acquire a full-length peptide-forming enzyme gene, the chromosomal DNA library was screened by colony hybridization using the aforementioned probe. The procedure for colony hybridization is explained in Molecular Cloning, 2nd edition, Cold Spring Harbor Press (1989).

The colonies of the chromosomal DNA library were transferred to a Nylon membrane filter, Nylon Membrane for Colony and Plaque Hybridization (manufactured by Roche Diagnostics), followed by treatments of alkali denaturation, neutralization, and immobilization. Hybridization was carried out using EASY HYB (manufactured by Boehringer-Mannheim). After pre-hybridizing the filter at 37° C. for 1 hour, the aforementioned digoxinigen-labeled probe was added, followed by hybridization at 37° C. for 16 hours. Subsequently, the filter was washed twice at 60° C. with 1×SSC containing 0.1% SDS.

Detection of colonies that hybridized with the labeled probe was carried out using the DIG Nucleotide Detection Kit (manufactured by Boehringer-Mannheim) based on the explanation described in the manual therefor. As a result, one strain whose colony hybridized with the labeled probe was observed.

(5) Base Sequence of Peptide-Forming Enzyme Gene Derived from *Psychroserpens burtonensis* ATCC 700359

Plasmids possessed by *Escherichia coli* JM109 were prepared from the strain that was verified to have hybridized with the labeled probe and the base sequence of a portion where hybridization with the probe occurred and nearby was determined. The sequencing reaction was carried out using the CEQ DTCS-Quick Start Kit (manufactured by Beckman-Coulter) based on the procedure described in the manual therefor. In addition, electrophoresis was carried out using the CEQ 2000-XL (manufactured by Beckman-Coulter).

As a result, it revealed that an open reading frame that encodes peptide-forming enzyme did exist. The full-length base sequence of the peptide-forming enzyme gene derived from *Psychroserpens burtonensis* ATCC 700359 (Depositary institution; the American Type Culture Collection, address of depositary institution; P.O. Box 1549, Manassas, Va. 20110, the United States of America) along with the corresponding amino acid sequence is shown in SEQ ID NO: 26.

Although the invention has been described with respect to a specific embodiment for a complete and clear disclosure, the appended claims are not to be thus limited but are to be construed as embodying all modifications and alternative constructions that may occur to one skilled in the art which fairly fall within the basic teaching herein set forth.

SEQUENCE LISTING FREE TEXT
SEQ ID NO: 3: Synthetic primer 1
SEQ ID NO: 4: Synthetic primer 2
SEQ ID NO: 5: Gene encoding a peptide-forming enzyme
SEQ ID NO: 7: Synthetic primer for preparing pTrpT
SEQ ID NO: 6: Synthetic primer for preparing pTrpT
SEQ ID NO: 9: Synthetic primer for preparing pTrpT_Gtg2
SEQ ID NO: 10: Synthetic primer for preparing pTrpT_Gtg2
SEQ ID NO: 11: Gene encoding a peptide-forming enzyme
SEQ ID NO: 13: Synthetic primer for preparing pTrpT_Sm_aet
SEQ ID NO: 14: Synthetic primer for preparing pTrpT_Sm_aet
SEQ ID NO: 15: Mix primer 1 for Aet
SEQ ID NO: 16: Mix primer 2 for Aet
SEQ ID NO: 19: Primer 1 for constructing aet expression vectors derived from *Pedobacter*
SEQ ID NO: 20: Primer 2 for constructing aet expression vectors derived from *Pedobacter*
SEQ ID NO: 21: Mix primer 3 for Aet

What we claim is:

1. A method of producing an α-L-aspartyl-L-phenylalanine-β-ester, comprising forming the α-L-aspartyl-L-phenylalanine-β-ester from L-aspartic acid-α,β-diester and L-phenylalanine using an enzyme or enzyme-containing substance that has an ability to selectively link L-phenylalanine to an α-ester site of the L-aspartic acid-α,β-diester through a peptide bond, wherein said enzyme or an enzyme in said enzyme-containing substance is selected from the group consisting of:
   a protein having the amino acid sequence consisting of amino acid residue 18 to 644 of SEQ ID NO:27,
   a protein having an amino acid sequence including substitution, deletion, insertion, and/or addition of one to thirty amino acids in the amino acid sequence consisting of amino acid residues 18 to 644 of SEQ ID NO:27, and having activity to selectively link L-phenylalanine to an α-ester site of the L-aspartic acid-α,β-diester through a peptide bond,
   a protein having the amino acid sequence of SEQ ID NO:27, and
   a protein containing a mature protein region, having an amino acid sequence including substitution, deletion, insertion, and/or addition of one to thirty amino acids in the amino acid sequence of SEQ ID NO:27, and having activity to selectively link L-phenylalanine to an α-ester site of the L-aspartic acid-α,β-diester through a peptide bond.

2. The method for producing an α-L-aspartyl-L-phenylalanine-β-ester according to claim 1, wherein the enzyme or enzyme-containing substance is one type or two or more types selected from the group consisting of a culture of a microbe that has an ability to selectively link L-phenylalanine to an α-ester site of the L-aspartic acid-α,β-diester through a peptide bond, a microbial cell separated from the culture and a treated microbial cell product of the microbe.

3. The method for producing an α-L-aspartyl-L-phenylalanine-β-ester according to claim 2, wherein the microbe is a microbe belonging to a genus selected from the group consisting of *Aeromonas, Azotobacter, Alcaligenes, Brevibacterium, Corynebacterium, Escherichia, Empedobacter, Flavobacterium, Microbacterium, Propionibacterium, Brevibacillus, Paenibacillus, Pseudomonas, Serratia, Stenotrophomonas, Sphingobacterium, Streptomyces, Xanthomonas, Williopsis, Candida, Geotrichum, Pichia, Saccharomyces, Torulaspora, Cellulophaga, Weeksella, Pedobacter, Persicobacter, Flexithrix, Chitinophaga, Cyclobacterium, Runella, Thermonema, Psychroserpens, Gelidibacter, Dyadobacter, Flammeovirga, Spirosoma, Flectobacillus, Tenacibaculum, Rhodotermus, Zobellia, Muricauda, Salegentibacter, Taxeobacter, Cytophaga, Marinilabilia, Lewinella, Saprospira,* and *Haliscomenobacter.*

4. A method of producing an α-L-aspartyl-L-phenylalanine-α-methyl ester, comprising: synthesizing an α-L-aspartyl-L-phenylalanine-β-methyl ester by producing an α-L-aspartyl-L-phenylalanine-β-ester according to the method of claim 3; and converting the α-L-aspartyl-L-phenylalanine-β-methyl ester to α-L-aspartyl-L-phenylalanine-α-methyl ester.

5. The method for producing an α-L-aspartyl-L-phenylalanine-β-ester according to claim 2, wherein the microbe is a transformed microbe that is capable of expressing a protein having an amino acid sequence consisting of amino acid residues 18 to 644 of SEQ ID NO:27.

6. The method for producing an α-L-aspartyl-L-phenylalanine-β-ester according to claim 2, wherein the microbe is a transformed microbe that is capable of expressing a protein having an amino acid sequence including substitution, deletion, insertion, and/or addition to thirty amino acids in the amino acid sequence consisting of amino acid residues 18 to 644 of SEQ ID NO:27, and having activity to selectively link L-phenylalanine to an α-ester site of the L-aspartic acid-α,β-diester through a peptide bond.

7. The method for producing an α-L-aspartyl-L-phenylalanine-β-ester according to claim 2, wherein the microbe is a transformed microbe that is capable of expressing a protein having the amino acid sequence of SEQ ID NO:27.

8. The method for producing an α-L-aspartyl-L-phenylalanine-β-ester according to claim 2, wherein the microbe is a transformed microbe that is capable of expressing a protein containing a mature protein region, having an amino acid sequence including substitution, deletion, insertion, and/or addition of one to thirty amino acids in the amino acid sequence of SEQ ID NO:27, and having activity to selectively link L-phenylalanine to an α-ester site of the L-aspartic acid-α,β-diester through a peptide bond.

9. A method of producing an α-L-aspartyl-L-phenylalanine-α-methyl ester, comprising: synthesizing an α-L-aspartyl-L-phenylalanine-β-methyl ester by producing an α-L-aspartyl-L-phenylalanine-β-ester according to the method of claim 2; and converting the α-L-aspartyl-L-phenylalanine-β-methyl ester to α-L-aspartyl-L-phenylalanine-α-methyl ester.

10. A method of producing an α-L-aspartyl-L-phenylalanine-α-methyl ester, comprising: synthesizing an α-L-aspartyl-L-phenylalanine-β-methyl ester by producing an α-L-aspartyl-L-phenylalanine-β-ester according to the method of claim 1; and converting the α-L-aspartyl-L-phenylalanine-β-methyl ester to α-L-aspartyl-L-phenylalanine-α-methyl ester.

11. A method of producing an α-L-aspartyl-L-phenylalanine-β-ester, comprising forming the α-L-aspartyl-L-phenylalanine-β-ester from L-aspartic acid-α,β-diester and L-phenylalanine using an enzyme or enzyme-containing substance that has an ability to selectively link L-phenylalanine to an α-ester site of the L-aspartic acid-α,β-diester through a peptide bond, wherein said enzyme or an enzyme in said enzyme-containing substance is selected from the group consisting of:
a protein encoded by a nucleotide sequence consisting of nucleotides 61 to 1992 of SEQ ID SEQ ID NO:26, and
a protein encoded by a nucleotide sequence consisting of nucleotides 112 to 1992 of SEQ ID NO:26.

12. The method for producing an α-L-aspartyl-L-phenylalanine-β-ester according to claim 11, wherein the enzyme or enzyme-containing substance is one type or two or more types selected from the group consisting of a culture of a microbe that has an ability to selectively link L-phenylalanine to an α-ester site of the L-aspartic acid-α,β-diester through a peptide bond, a microbial cell separated from the culture and a treated microbial cell product of the microbe.

13. The method for producing an α-L-aspartyl-L-phenylalanine-β-ester according to claim 12, wherein the microbe is a microbe belonging to a genus selected from the group consisting of *Aeromonas, Azotobacter, Alcaligenes, Brevibacterium, Corynebacterium, Escherichia, Empedobacter, Flavobacterium, Microbacterium, Propionibacterium, Brevibacillus, Paenibacillus, Pseudomonas, Serratia, Stenotrophomonas, Sphingobacterium, Streptomyces, Xanthomonas, Williopsis, Candida, Geotrichum, Pichia, Saccharomyces, Torulaspora, Cellulophaga, Weeksella, Pedobacter, Persicobacter, Flexithrix, Chitinophaga, Cyclobacterium, Runella, Thermonema, Psychroserpens, Gelidibacter, Dyadobacter, Flammeovirga, Spirosoma, Flectobacillus, Tenacibaculum, Rhodotermus, Zobellia, Muricauda, Salegentibacter, Taxeobacter, Cytophaga, Marinilabilia, Lewinella, Saprospira,* and *Haliscomenobacter.*

14. A method of producing an α-L-aspartyl-L-phenylalanine-α-methyl ester, comprising: synthesizing an α-L-aspartyl-L-phenylalanine-β-methyl ester by producing an α-L-aspartyl-L-phenylalanine-β-ester according to the method of claim 13; and converting the α-L-aspartyl-L-phenylalanine-β-methyl ester to α-L-aspartyl-L-phenylalanine-α-methyl ester.

15. The method for producing an α-L-aspartyl-L-phenylalanine-β-ester according to claim 12, wherein the microbe is a transformed microbe that is capable of expressing a protein encoded by a nucleotide sequence consisting of nucleotides 61 to 1992 of SEQ ID SEQ ID NO:26.

16. The method for producing an α-L-aspartyl-L-phenylalanine-β-ester according to claim 12, wherein the microbe is a transformed microbe that is capable of expressing a protein encoded by a nucleotide sequence consisting of nucleotides 112 to 1992 of SEQ ID NO:26.

17. A method of producing an α-L-aspartyl-L-phenylalanine-α-methyl ester, comprising: synthesizing an α-L-aspartyl-L-phenylalanine-β-methyl ester by producing an α-L-aspartyl-L-phenylalanine-β-ester according to the method of claim 12; and converting the α-L-aspartyl-L-phenylalanine-β-methyl ester to α-L-aspartyl-L-phenylalanine-α-methyl ester.

18. A method of producing an α-L-aspartyl-L-phenylalanine-α-methyl ester, comprising: synthesizing an α-L-aspartyl-L-phenylalanine-β-methyl ester by producing an α-L-aspartyl-L-phenylalanine-β-ester according to the method of claim 11; and converting the α-L-aspartyl-L-phenylalanine-β-methyl ester to α-L-aspartyl-L-phenylalanine-α-methyl ester.

* * * * *